US011000514B2

(12) United States Patent
Covel et al.

(10) Patent No.: US 11,000,514 B2
(45) Date of Patent: *May 11, 2021

(54) ANTIFUNGAL COMPOUNDS

(71) Applicant: Duke University, Durham, NC (US)

(72) Inventors: Jonathan A. Covel, San Diego, CA (US); Mitchell Mutz, San Diego, CA (US); Peter J. Webb, San Diego, CA (US); Robert Remme Webb, II, San Diego, CA (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/796,609

(22) Filed: Feb. 20, 2020

(65) Prior Publication Data

US 2020/0188364 A1    Jun. 18, 2020

Related U.S. Application Data

(63) Continuation of application No. 15/968,692, filed on May 1, 2018, now Pat. No. 10,568,872, which is a continuation of application No. 15/207,384, filed on Jul. 11, 2016, now Pat. No. 9,956,207, which is a continuation of application No. PCT/US2015/011247, filed on Jan. 13, 2015.

(60) Provisional application No. 61/926,413, filed on Jan. 13, 2014.

(51) Int. Cl.
| | |
|---|---|
| *A61K 31/436* | (2006.01) |
| *A61K 31/01* | (2006.01) |
| *A61K 31/131* | (2006.01) |
| *A61K 31/407* | (2006.01) |
| *A61K 31/4164* | (2006.01) |
| *A61K 31/4192* | (2006.01) |
| *A61K 31/4196* | (2006.01) |
| *A61K 31/425* | (2006.01) |
| *A61K 31/437* | (2006.01) |
| *A61K 31/497* | (2006.01) |
| *A61K 31/5377* | (2006.01) |
| *A61K 31/685* | (2006.01) |
| *A61K 31/695* | (2006.01) |
| *A61K 45/06* | (2006.01) |

(52) U.S. Cl.
CPC ............ *A61K 31/436* (2013.01); *A61K 31/01* (2013.01); *A61K 31/131* (2013.01); *A61K 31/407* (2013.01); *A61K 31/4164* (2013.01); *A61K 31/4192* (2013.01); *A61K 31/4196* (2013.01); *A61K 31/425* (2013.01); *A61K 31/437* (2013.01); *A61K 31/497* (2013.01); *A61K 31/5377* (2013.01); *A61K 31/685* (2013.01); *A61K 31/695* (2013.01); *A61K 45/06* (2013.01)

(58) Field of Classification Search
CPC ... A61K 31/695; A61K 31/436; A61K 31/685
See application file for complete search history.

(56) References Cited

U.S. PATENT DOCUMENTS

| | | | |
|---|---|---|---|
| 4,929,611 A * | 5/1990 | Okuhara | ............... C12P 17/188 514/183 |
| 5,378,836 A | 1/1995 | Kao et al. | |
| 5,457,111 A | 10/1995 | Luly et al. | |
| 2003/0144315 A1 | 7/2003 | Chu et al. | |
| 2006/0035918 A1 | 2/2006 | Hirayama et al. | |
| 2012/0108529 A1 | 5/2012 | Webb et al. | |

FOREIGN PATENT DOCUMENTS

| | | |
|---|---|---|
| EP | 0184162 | 6/1986 |
| WO | WO 2012047762 | 4/2012 |

OTHER PUBLICATIONS

Bourre, et al. Neuroscience Letters 336 (2003) 180-184 (Year: 2003).
Brizuela et al., "Antifungal Properties of the Immunosuppressant FK-506: Identification of an FK-506-Responsive Yeast Gene Distinct from FKBJ" Molecular and Cellular Biology, 1991; 11(9): 4616-4626.
Written opinion for PCT/US15/11247.
Yura et al., "Synthesis and pharmacokinetics of a novel macromolecular prodrug of Tacrolimus (FK506), fk506-dextran conjugate" Journal of Controlled Release, 1999; 57: 87-100.

* cited by examiner

*Primary Examiner* — San Ming R Hui
(74) *Attorney, Agent, or Firm* — Casimir Jones, SC; Robert A. Goetz

(57) ABSTRACT

The technical field of the invention is in pharmaceutical compounds and methods. In an aspect, the disclosure provides macrolide compounds suitable for use as antifungal agents, as well as methods for their use and compositions containing the same.

3 Claims, No Drawings

ANTIFUNGAL COMPOUNDS

This application is a continuation of U.S. patent application Ser. No. 15/968,692, filed May 1, 2018, allowed as U.S. Pat. No. 10,568,872, which is a continuation of U.S. patent application Ser. No. 15/207,384, filed Jul. 11, 2016, allowed as U.S. Pat. No. 9,956,207, which is a 371 National Entry of PCT/US2015/011247, filed Jan. 13, 2015, which claims priority to U.S. Provisional Patent Application No. 61/926,413, filed Jan. 13, 2014, the contents of which are incorporated by reference in their entireties.

BACKGROUND

Tacrolimus (also referred to as FK-506) is a compound known to have immunosuppressive activity. As an immunosuppressive, it is used in a variety of situations such as organ transplantations and eczema treatment. The structure of tacrolimus includes a macrocyclic lactone, and various structurally related macrolide compounds are known.

Relevant art: US 2006/0035918; U.S. Pat. No. 5,457,111.

SUMMARY OF THE INVENTION

In an aspect is a method for treating a patient suffering from a fungal infection, the method comprising administering to the patient an effective amount of a composition comprising a compound of formula (I)

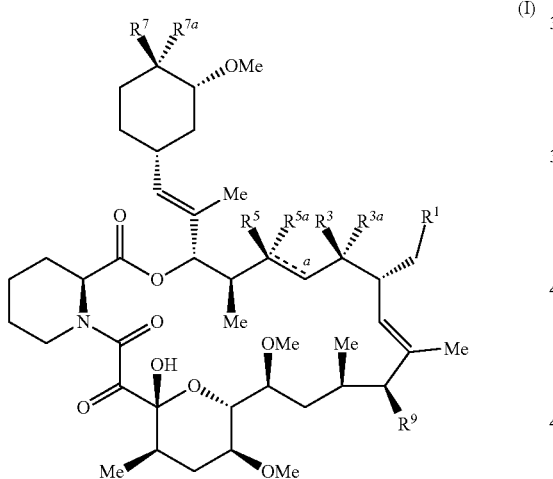

(I)

In formula (I), "a" is a double bond optionally present (provided that $R^5$ or $R^{5a}$ is not present); $R^1$ is selected from alkyl, alkenyl, or is taken together with $R^3$ or $R^{3a}$ to form a cycle; $R^3$ and $R^{3a}$ are independently selected from —H and —OH, or $R^3$ and $R^{3a}$ together form =X, where X is selected from O, C, and N such that =X and the carbon atom to which it is attached forms a carbonyl, oxime, substituted oxime, imine, substituted imine, hydrazone, substituted hydrazone, terminal olefin, or substituted olefin functional group, or wherein one of $R^3$ and $R^{3a}$ is taken together with $R^1$ or $R^5$ or $R^{5a}$ to form a cycle (and the other is H); $R^5$ and $R^{5a}$ are independently selected from —H, —OH, or -OTBS, or $R^5$ and $R^{5a}$ together form =O, or one of $R^5$ and $R^{5a}$ is —H and the other is taken together with $R^3$ or $R^{3a}$ to form a cycle; $R^7$ and $R^{7a}$ are independently selected from —H, —OH, —NH$_2$, alkoxy, alkylcarboxy, alkenylcarboxy, and substituted versions thereof, or $R^7$ and $R^{7a}$ together form =Y, where Y is selected from O, and N such that =Y and the carbon atom to which it is attached forms a carbonyl or oxime functional group; and R9 is selected from —H and —OH.

In embodiments:
the compound has the structure of formula (IA-a), (IA-b), or (IA-c)

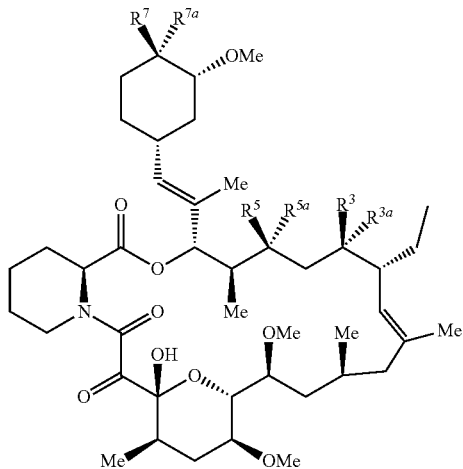

(IA-a)

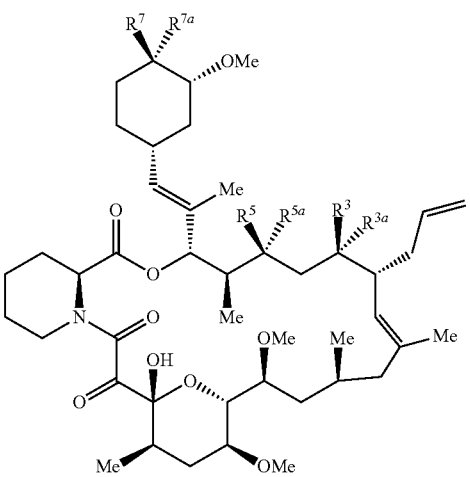

(IA-b)

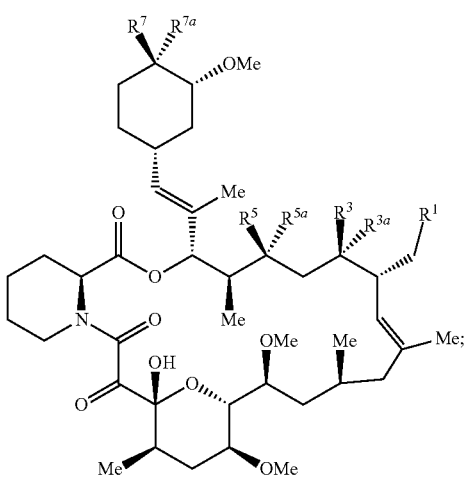

(IA-c)

the compound has the structure of formula (IB-a), (IB-b), (IB-c), or (IB-d)

(IB-a)
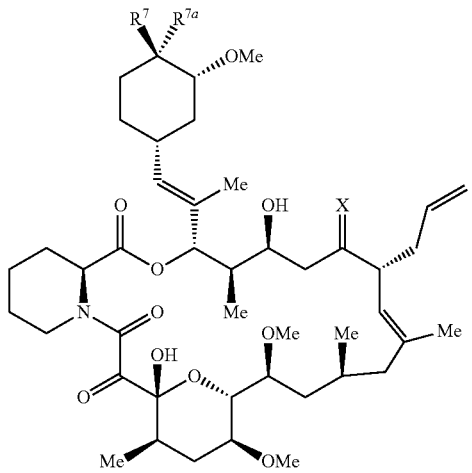

(IB-b)
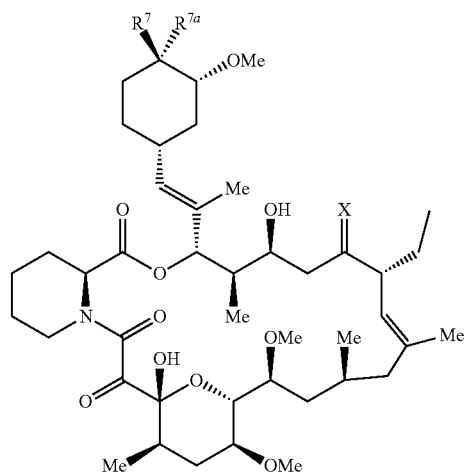

(IB-c)
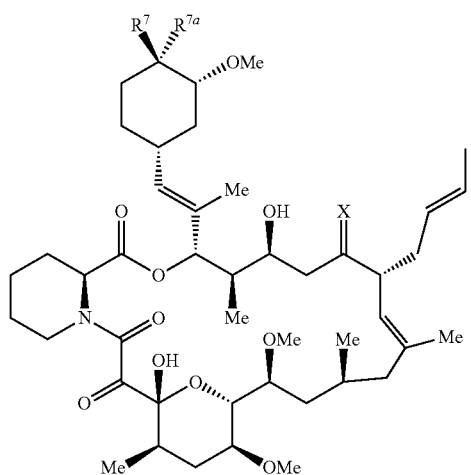

(IB-d)
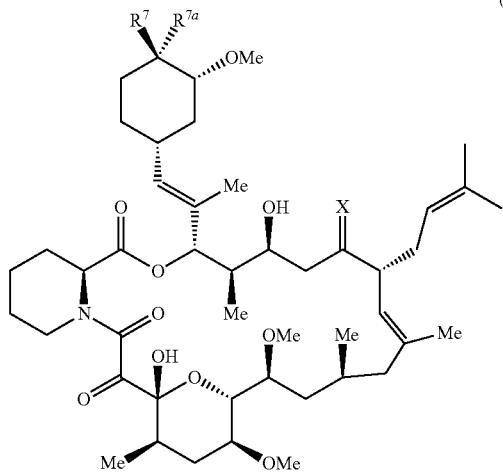

wherein =X is selected from =C($R^{3b}$)($R^{3c}$), =N—$OR^{3d}$, =N—NH($R^{3c}$), and =N—N=C(CH$_3$)$_2$, $R^{3b}$ and $R^{3c}$ are independently selected from —H, —CN, and unsubstituted alkyl, $R^{3d}$ is selected from H, alkyl, aralkyl, and a function group, and $R^{3e}$ is alkyl;

the compound has the structure of formula (IC-a), (IC-b), (IC-c), or (IC-d)

(IC-a)
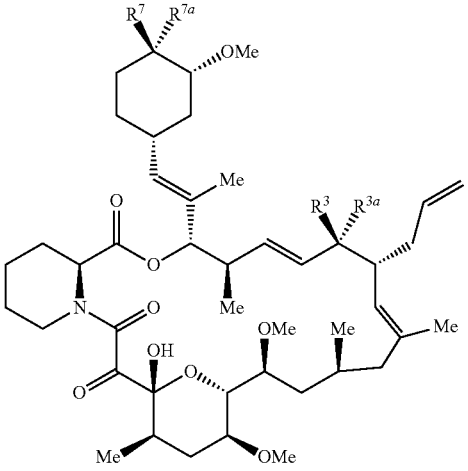

(IC-b)
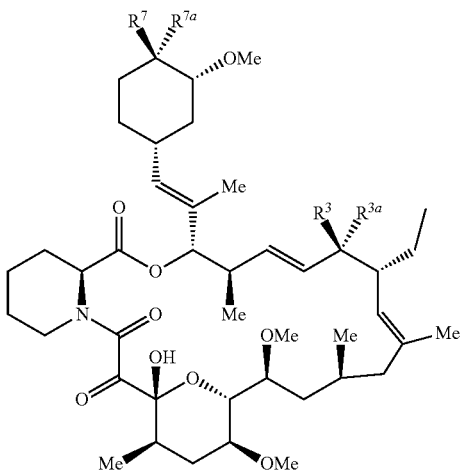

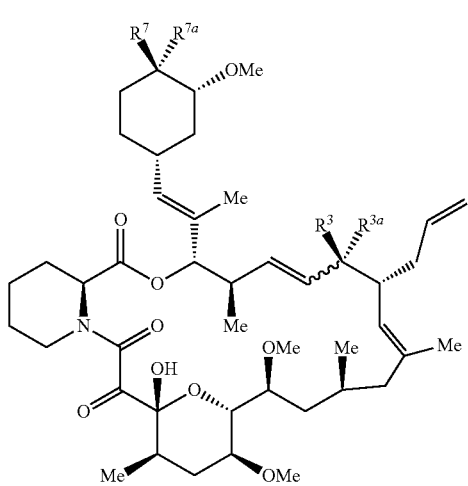
(IC-c)
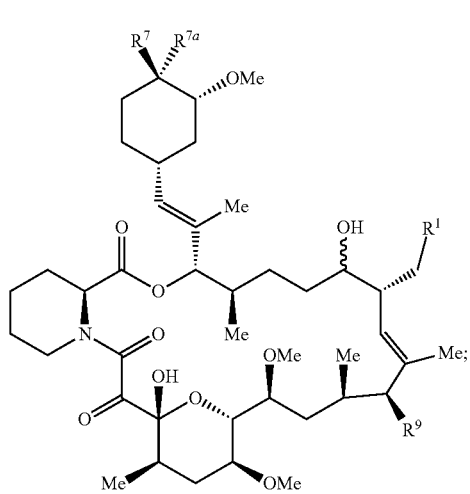
(IE)
and
the compound has the structure of formula (IF), (IG), or (IH)
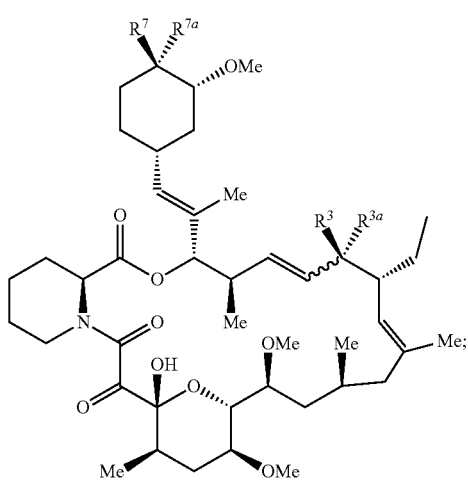
(IC-d)
the compound has the structure of formula (ID) or (IE)
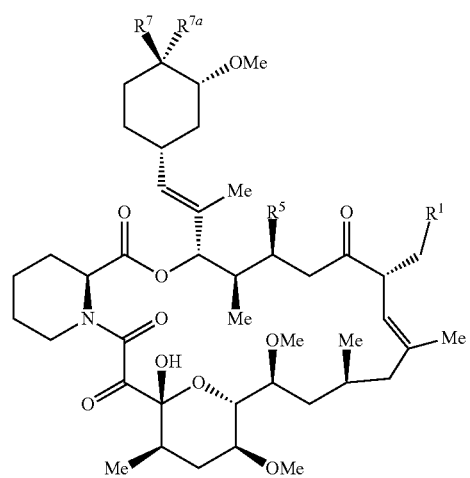
(IF)
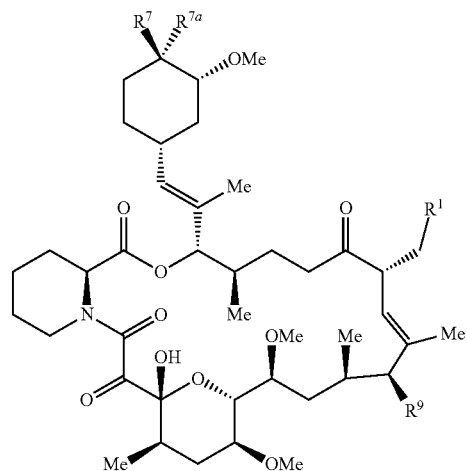
(ID)
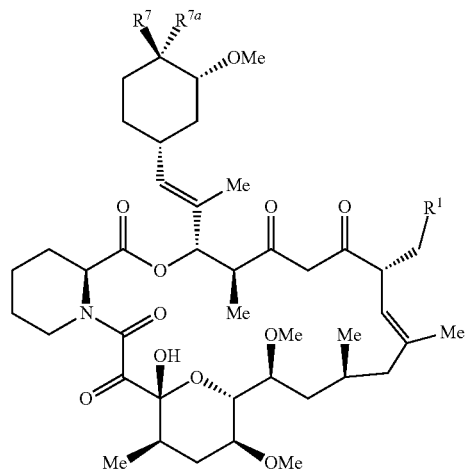
(IG)

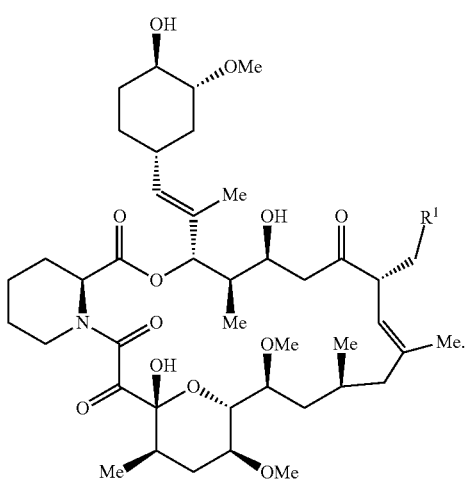

(IH)

In an aspect is an anti-fungal formulation comprising an effective amount of a compound having the structure of formula (I) as described above, and further comprising a second antifungal agent.

In an embodiment, the second antifungal agent is selected from compounds according to formula (I), polyenes, imidazoles, triazoles, thiazoles, allylamines, and echinochandins.

In an embodiment, there is provided a compound according to any of the structures described herein.

These and other aspects of the invention will be apparent to the skilled artisan based on the disclosure herein. The technical field of the invention is in pharmaceutical compounds and methods.

DETAILED DESCRIPTION OF PARTICULAR EMBODIMENTS

The term "alkyl" as used herein refers to a branched, unbranched or cyclic saturated hydrocarbon group of 1 to about 50 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein may contain 1 to about 36, more typically 1 to 10, carbon atoms. The alkyl groups described herein may be unsubstituted or they may be substituted with one or more substituents including functional groups (e.g., amine, hydroxyl, an olefinic group such as a vinyl or an allyl group), or the like. "Substituted alkyl" refers to alkyl substituted with one or more substituent groups, and this includes instances wherein two hydrogen atoms from the same carbon atom in an alkyl are replaced, such as in a carbonyl group (i.e., a substituted alkyl group may include a —C(=O)-moiety). Other substituents include halogen, ether, hydroxyl, amine functional groups, etc. as defined in more detail below (see "functional groups"). The terms "heteroatom-containing alkyl" and "heteroalkyl" refer to an alkyl substituent in which at least one carbon atom is replaced with a heteroatom, such as o, S, P, or N, as described in further detail infra. If not otherwise indicated, the term "alkyl" includes linear, branched, cyclic, unsubstituted, substituted, heteroatom-containing, and substituted heteroatom-containing alkyl.

The term "alkylene" as used herein refers to a difunctional saturated branched or unbranched hydrocarbon chain containing from 1 to 50 carbon atoms, more typically from 1 to 12 carbon atoms, and includes, for example, methylene (—CH$_2$—), ethylene (—CH$_2$CH$_2$—), propylene (—CH$_2$CH$_2$CH$_2$—), 2-methylpropylene (—CH$_2$—CH (CH$_3$)—CH$_2$—), hexylene (—(CH$_2$)$_6$—) and the like. Similarly, the terms "alkenylene," "alkynylene," "arylene," "alkarylene," and "aralkylene" refer to difunctional (i.e., linking) alkenyl, alkynyl, aryl, alkaryl, and aralkyl groups, respectively.

The term "alkenyl" as used herein refers to a linear, branched or cyclic hydrocarbon group of 2 to about 50 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 36 carbon atoms, and for example may contain 2 to 12 carbon atoms, or more typically 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, heteroatom-containing, and substituted heteroatom containing alkenyl.

The term "alkynyl" as used herein refers to a linear or branched hydrocarbon group of 2 to 50 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms, or more typically 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the term "alkynyl" includes linear, branched, unsubstituted, substituted, and/or heteroatom-containing alkynyl.

The term "aryl" as used herein refers to an aromatic species having 1 to 3 rings, but typically intends a monocyclic or bicyclic moiety, e.g., phenyl or 1- or 2-naphthyl groups. Optionally, these groups are substituted with 1 to 4, more preferably 1 to 2, substituents such as those described herein, including alkyl, alkoxy, hydroxyl, amino, and/or nitro. Aryl groups may, for example, contain 6 to 50 carbon atoms, and as a further example, aryl groups may contain 6 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom. If not otherwise indicated, the term "aryl" includes unsubstituted, substituted, heteroatom-containing, and substituted heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 50 carbon atoms. Aralkyl and alkaryl groups may, for example, contain 6 to 20 carbon atoms, and as a further example, such groups may contain 6 to 12 carbon atoms. Unless specified otherwise, the terms "alkaryl" and "aralkyl" include substituted, heteroatom-containing, and substituted heteroatom-containing versions thereof.

The term "amino" intends an amino group —NR$_2$ where R is hydrogen or an alternative substituent, typically alkyl. The term "amino" is thus intended to include primary amino (i.e., NH$_2$), "alkylamino" (i.e., a secondary amino group containing a single alkyl substituent), and "dialkylamino" (i.e., tertiary amino group containing two alkyl substituents).

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Halo" or "halogen" refers to fluoro, chloro, bromo or iodo, and usually relates to halo substitution for a hydrogen atom in an organic compound.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: C$_1$-C$_{24}$ alkyl (including C$_1$-C$_{18}$ alkyl, further including C$_1$-C$_{12}$ alkyl, and further including C$_1$-C$_6$ alkyl), C$_2$-C$_{24}$ alkenyl (including C$_2$-C$_{18}$ alkenyl, further including C$_2$-C$_{12}$ alkenyl, and further including C$_2$-C$_6$ alkenyl), C$_2$-C$_{24}$ alkynyl (including C$_2$-C$_{18}$ alkynyl, further including C$_2$-C$_{12}$ alkynyl, and further including C$_2$-C$_6$ alkynyl), C$_5$-C$_{30}$ aryl (including C$_5$-C$_{20}$ aryl, and further including C$_5$-C$_{12}$ aryl), C$_6$-C$_{30}$ aralkyl (including C$_6$-C$_{20}$ aralkyl, and further including C$_6$-C$_{12}$ aralkyl), C$_6$-C$_{30}$ alkaryl (including C$_6$-C$_{20}$ alkaryl, and further including C$_6$-C$_{12}$ alkaryl), and functional groups such as halo, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{20}$ arylcarbonato (—O—(CO)—O-aryl), C$_2$-C$_{24}$ alkylcarbonyloxy (—O—(CO)-alkyl), C$_6$-C$_{24}$ arylcarbonyloxy (—O—(CO)-aryl), carboxy (—COOH), carboxylato (—COO—), carbamoyl (—(CO)—NH$_2$), mono-substituted C$_1$-C$_{24}$ alkylcarbamoyl (—(CO)—NH(C$_1$-C$_{24}$ alkyl)), di-substituted alkylcarbamoyl (—(CO)—N(C$_1$-C$_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N≡C—), isothiocyanato (—S—C≡N), azido (—N=N+=N—), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_5$-C$_{20}$ arylamido (—NH—(CO)-aryl), imino (—CR=NH where R=hydrogen, C$_1$-C$_{24}$ alkyl, C$_5$-C$_{20}$ aryl, C$_6$-C$_{20}$ alkaryl, C$_6$-C$_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), phosphino (—PH$_2$), mono- and di-(C$_1$-C$_{24}$ alkyl)-substituted phosphino, and mono- and di-(C$_5$-C$_{20}$ aryl)-substituted phosphino. In addition, the aforementioned functional groups may, if a particular group permits, be further substituted with one or more additional functional groups or with one or more hydrocarbon moieties (alkyl, aryl, etc.). Analogously, the above-mentioned hydrocarbon moieties may be further substituted with one or more functional groups or additional hydrocarbon moieties such as those specifically enumerated. It will be appreciated that functional groups may be attached via a heteroatom or, where appropriate, via a carbon atom, to the remainder of the compound.

In an aspect is a compound having the structure of formula (I)

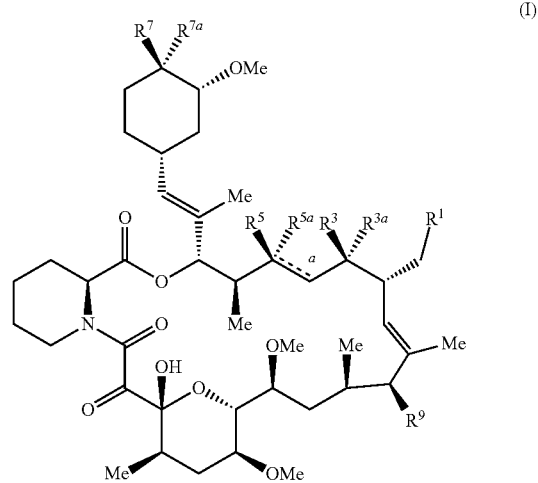

In formula (I), "a" is a double bond optionally present (provided that R$^5$ or R$^{5a}$ is not present); R$^1$ is selected from alkyl, alkenyl, or is taken together with R$^3$ or R$^{3a}$ to form a cycle; R$^3$ and R$^{3a}$ are independently selected from —H and —OH, or R$^3$ and R$^{3a}$ together form =X, where X is selected from O, C, and N such that =X and the carbon atom to which it is attached forms a carbonyl, oxime, substituted oxime, imine, substituted imine, hydrazone, substituted hydrazone, terminal olefin, or substituted olefin functional group, or wherein one of R$^3$ and R$^{3a}$ is taken together with R$^1$ or R$^5$ or R$^{5a}$ to form a cycle (and the other is H); R$^5$ and R$^{5a}$ are independently selected from —H, —OH, or -OTBS, or R$^5$ and R$^{5a}$ together form =O, or one of R$^5$ and R$^{5a}$ is —H and the other is taken together with R$^3$ or R$^{3a}$ to form a cycle; R$^7$ and R$^{7a}$ are independently selected from —H, —OH, —NH$_2$, alkoxy, alkylcarboxy, alkenylcarboxy, and substituted versions thereof, or R$^7$ and R$^{7a}$ together form =Y, where Y is selected from O, and N such that =Y and the carbon atom to which it is attached forms a carbonyl or oxime functional group; and R9 is selected from —H and —OH.

In formula (I), $R^1$ is selected from alkyl and alkenyl, or $R^1$ may be taken together with $R^3$ or $R^{3a}$ to form a cycle. Examples of alkyl groups include methyl and substituted methyl (e.g., —C(=O)-Me, —C(=O)—OH, and —C(=O)—OMe), while examples of alkenyl groups include —CH=CR$^{1c}$R$^{1d}$. Where $R^1$ is —CH=CR$^{1c}$R$^{1d}$, the double bond may be in the E- or Z-configuration, and the formulation may comprise a single isomer or a mixture of isomers. In embodiments, $R^1$ is unsubstituted alkyl or unsubstituted alkenyl.

$R^{1c}$ and $R^{1d}$ are independently selected from: H, alkyl, aryl, alkaryl, aralkyl, and a functional group. Examples include —(CH$_2$)$_n$CH$_3$ where n is an integer (e.g., an integer in the range 0-20, or an integer selected from 0, 1, 2, 3, 4, 5, etc.), cyclohexyl, substituted alkyl (substituents such as aryl and functional groups), phenyl, substituted phenyl (substituents such as alkyl, alkenyl, functional groups, etc.), alkoxycarbonyl (e.g., C(=O)O-alkyl and C(=O)O-aryl), alkylsulfonyl (e.g., —SO$_2$-Me or —SO$_2$-Et), etc.

In embodiments, $R^1$ is alkyl including branched alkyl, such as methyl, ethyl, i-propyl, butyl, t-butyl, etc.

In any of the embodiments of formula (I) described herein where $R^1$ is not part of a cycle, $R^1$ may be selected from —Me and —CH=CH$_2$.

In embodiments, $R^1$ is taken together with $R^3$ or $R^{3a}$ to form substituted or unsubstituted pyridazine.

In embodiments of formula (I), $R^3$ and $R^{3a}$ are independently selected from —H or —OH, or $R^3$ and $R^{3a}$ are taken together to form =X, where X is O, N, or C such that X and the carbon atom to which it is attached form carbonyl, oxime, substituted oxime, imine, substituted imine, hydrazone, or substituted hydrazone, or X is C to form an olefin (terminal or internal). In embodiments, =X is selected from =O, =C(R$^{3b}$)(R$^{3c}$), =N—OR$^{3d}$, =N—N=C(CH$_3$)$_2$, and =N—NH—R$^{3e}$, or wherein $R^3$ or $R^{3a}$ is taken together with $R^1$ or $R^5$ or $R^{5a}$ to form a cycle. In embodiments, $R^3$ and $R^{3a}$ together are =O; =C(R$^{3b}$)(R$^{3c}$); or =N—OR$^{3d}$. In embodiments, $R^3$ and $R^{3a}$ together are =O or =C(R$^{3b}$)(R$^{3c}$). In embodiments, $R^3$ and $R^{3a}$ together are =N—OR$^{3d}$, with two isomers present for the possible orientations of the —OR$^{3d}$ group. The compound may be racemic (with both isomers) or may be a single oxime isomer in the formulations described herein.

In embodiments, $R^3$ and $R^{3a}$ are both H.

In embodiments, $R^{3b}$ and $R^{3c}$ are independently selected from H and unsubstituted alkyl. In embodiments $R^{3b}$ and $R^{3c}$ are both H. In embodiments exactly one of $R^{3b}$ and $R^{3c}$ is H and the other is unsubstituted alkyl. In embodiments both $R^{3b}$ and $R^{3c}$ are unsubstituted alkyl. Examples of alkyl include methyl, ethyl, propyl (n-propyl or i-propyl), butyl (n-butyl, i-butyl, t-butyl), pentyl, and hexyl. In other embodiments, one of $R^{3b}$ and $R^{3c}$ is H, and the other is —CN.

$R^{3d}$ is selected from H, alkyl, aralkyl, and a function group. Examples of alkyl include methyl, ethyl, propyl (i.e., n- and i-propyl), butyl (i.e., n-, i-, and t-butyl), —(CH$_2$)$_n$—CH$_3$ (wherein n is in the range 1-5 or 1-3, or is 1, 2, 3, 4, or 5), —CH$_2$—COOH, and —(CH$_2$)$_n$—OH (wherein n is in the range 1-5 or 2-4, or is 1, 2, 3, 4, or 5). Examples of aralkyl include —CH$_2$—C$_6$H$_4$—NO$_2$ and —CH$_2$-C$_6$H$_3$Cl$_2$. Examples of functional groups include —S(=O)$_2$—OH.

$R^{3e}$ is alkyl. Examples of alkyl include methyl, ethyl, propyl (i.e., n- and i-propyl), butyl (i.e., n-, i-, and t-butyl), —(CH$_2$)$_n$—CH$_3$ (wherein n is in the range 1-5 or 1-3, or is 1, 2, 3, 4, or 5), —(CH$_2$)$_n$—OH (wherein n is in the range 1-5 or 2-4, or is 1, 2, 3, 4, or 5), etc.

In formula (I), in embodiments, bond "a" is present and $R^{5a}$ is not present. In other embodiments, bond "a" is not present and $R^{5a}$ is present. In some such embodiments, $R^{5a}$ is H.

In formula (I), one of $R^5$ and $R^{5a}$ is —OH or -OTBS and the other is H, or $R^5$ and $R^{5a}$ taken together form =O, or $R^5$ is taken together with $R^3$ to form a cycle. In embodiments, $R^3$ or $R^{3a}$ and $R^5$ or $R^{5a}$ are taken together to form a cycle such as a ketal or acetal (e.g., a dimethylacetonide).

In formula (I), one of $R^7$ and $R^{7a}$ is selected from —OH, —NH$_2$, alkylcarboxy (e.g., —O—CO—CH$_2$—COOH), alkenylcarboxy (e.g., —O—CO—CH$_2$CH$_2$CH=CH$_2$, —O—CO—CH$_2$CH$_2$CH=CH—COOH, etc.), and thiocarbonato (e.g., —O—C(=S)—O—R where R is alkyl or aryl). Alternatively, $R^7$ and $R^{7a}$ together form =Y, where =Y is N or O to form an oxime or carbonyl group.

In embodiments, $R^7$ and $R^{7a}$ are both —H.

In embodiments, the compounds have the structure of formula (IA-a), (IA-b), or (IA-c)

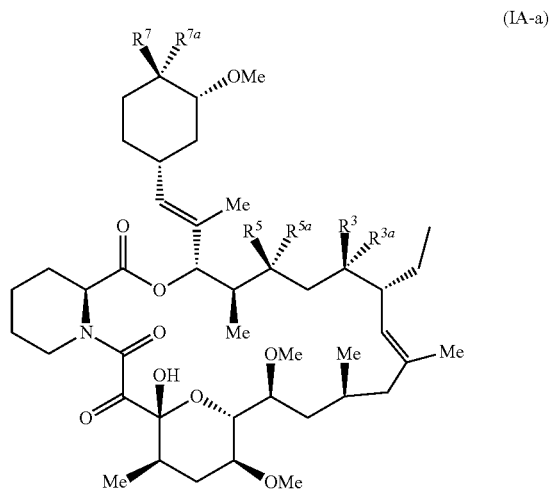

(IA-a)

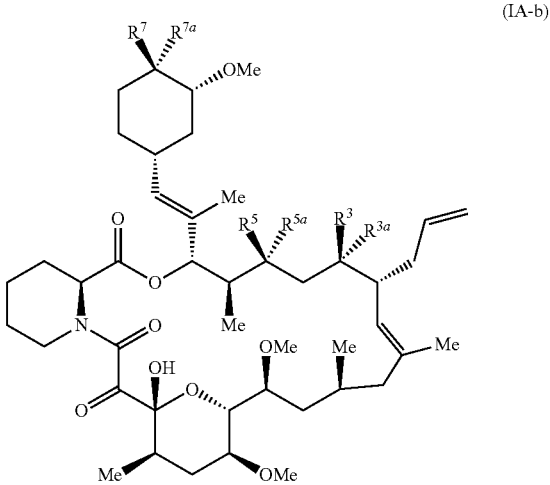

(IA-b)

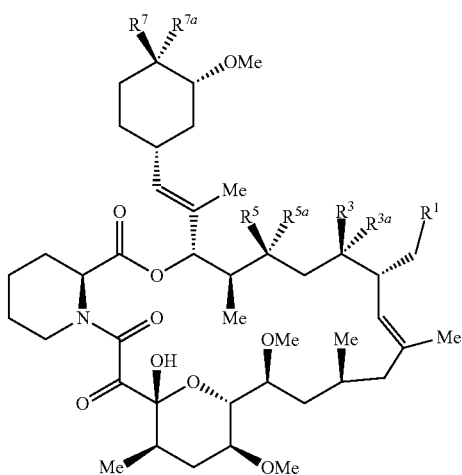
(IA-c)

In formula (IA-a), (IA-b), and (IA-c), one of $R^3$ and $R^{3a}$ is H and the other is taken with $R^1$ (formula IA-c) or with $R^5$ or $R^{5a}$ to form a cycle; and $R^7$, and $R^{7a}$ are as defined for formula (I).

For example, in formula (IA-a) and (IA-b), $R^7$ and $R^{7a}$ are OH and H, respectively, $R^3$ and $R^{5a}$ are —H, and $R^{3a}$ and $R^5$ are taken together to form a cycle. An example cycle is an acetonide group. Alternatively, $R^3$ and $R^5$ are H, and $R^{3a}$ and $R^{5a}$ are taken together to form an acetonide or other cycle. Alternatively, $R^{3a}$ and $R^5$ are H, and $R^3$ and $R^{5a}$ are taken together to form an acetonide or other cycle. Alternatively, $R^{3a}$ and $R^{5a}$ are H, and $R^3$ and $R^5$ are taken together to form an acetonide or benzylidene acetal (i.e. —O—C(H)(Ph)—O— where the oxygen atoms are connected at C22 and C24). In such compounds, $R^7$ and $R^{7a}$ may alternatively both be —H, or may together form =O.

For example, in formula (IA-c), $R^7$ and $R^{7a}$ are OH and H, respectively, $R^5$ and $R^{5a}$ are OH and H, respectively, and $R^3$ or $R^{3a}$ is taken together with $R^1$ to form a substituted or unsubstituted pyridazine cycle (the other of $R^3$ and $R^{3a}$ being H). Example substituents are alkyl.

In embodiments, the compounds have the structure of formula (IB-a) or (IB-b) or (IB-c) or (IB-d):

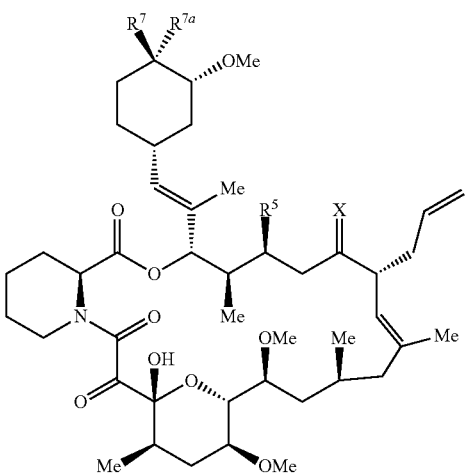
(IB-a)

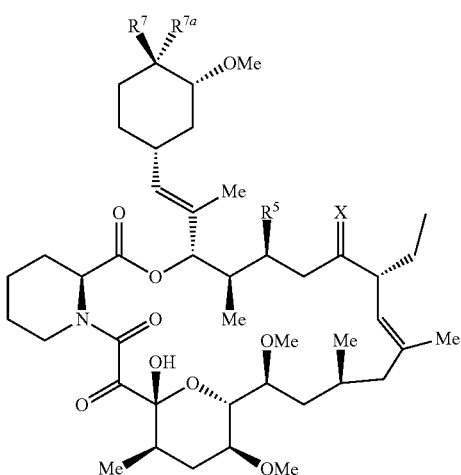
(IB-b)

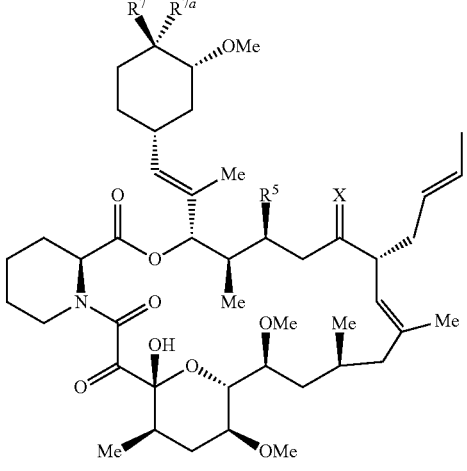
(IB-c)

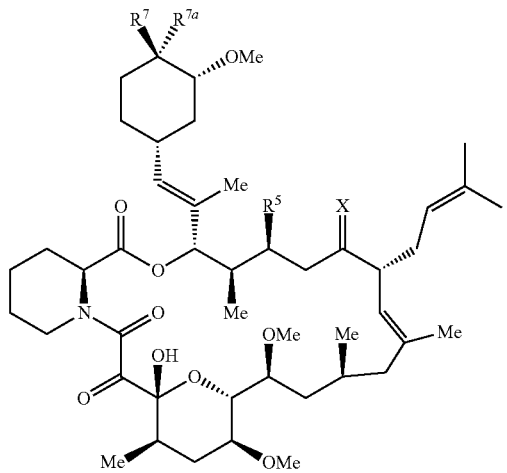
(IB-d)

In embodiments of formula (IB-a), (IB-b), (IB-c), and (IB-d), =X is selected from =C($R^{3b}$)($R^{3c}$), =N—O$R^{3d}$, =N—NH($R^{3e}$), and =N—N=C(CH$_3$)$_2$, $R^{3b}$, $R^{3c}$, $R^{3d}$, $R^{3e}$, $R^5$, $R^7$, and $R^{7a}$ are as defined previously for formula (I).

For example, in formula (IB-a), (IB-b), (IB-c), and (IB-d), $R^5$ is —OH, $R^7$ and $R^{7a}$ are OH and H, respectively, and X is =CH$_2$.

For example, in formula (IB-a), (IB-b), (IB-c), and (IB-d), $R^5$ is —OH, $R^7$ and $R^{7a}$ are OH and H, respectively, and X is =N—OH.

For example, in formula (IB-a), (IB-b), (IB-c), and (IB-d), $R^5$ is —OH, $R^7$ and $R^{7a}$ are OH and H, respectively, and X is =N—O—$R^{3d}$. For example, $R^5$ is —OH, $R^7$ and $R^{7a}$ are OH and H, respectively, and X is selected from =N—O—CH$_3$, =N—O—(CH$_2$)$_n$—CH$_3$ (n=1, 2, or 3), =N—O—CH(CH$_3$)$_2$, =N—O—C(CH$_3$)$_3$, =N—O—(CH$_2$)$_n$—OH (n=1, 2, or 3), and =N—O—(CH$_2$)$_n$—COOH (n is 1, 2, or 3). Or for example, $R^5$ is —OH, $R^7$ and $R^{7a}$ are OH and H, respectively, and X is =N—O—CH$_2$-aryl, where aryl is phenyl, nitrophenyl (e.g., 4-nitrophenyl), or halophenyl (e.g., chlorophenyl such as 4-chlorophenyl, dichlorophenyl such as 2,4-dichlorophenyl, and trichlorophenyl such as 2,4,6-trichlorophenyl).

For example, in formula (IB-a), (IB-b), (IB-c), and (IB-d), $R^5$ is —H or —OH, $R^7$ and $R^{7a}$ are OH and H, respectively, and X is =C(H)(CN). Also for example, X is =C(Me)(Et).

For example, in formula (IB-a), (IB-b), (IB-c), and (IB-d), $R^5$ is —H or —OH, $R^7$ and $R^{7a}$ are OH and H, respectively, X is =N—NH—$R^{3e}$, and $R^{3e}$ is selected from methyl, ethyl, i-propyl, n-propyl, and —(CH$_2$)$_n$—OH (n is 0, 1, 2, or 3).

For example, in formula (IB-a), (IB-b), (IB-c), and (IB-d), $R^5$ is —H or —OH, $R^7$ and $R^{7a}$ are OH and H, respectively, X is =N—N=C(CH$_3$)$_2$.

For example, in formula (IB-a), (IB-b), (IB-c), and (IB-d), $R^5$ is —H or —OH, $R^7$ and $R^{7a}$ are OH and H, respectively, X is =N—O—SO$_2$—H or =N—O—SO$_2$—R where R is alkyl such as Me.

For example, in formula (IB-a), (IB-b), (IB-c), and (IB-d), $R^5$ is —H or —OH, $R^7$ and $R^{7a}$ are taken together to form =N—OH, and X is =N—OH.

For example, in formula (IB-a), (IB-b), (IB-c), and (IB-d), one of $R^7$ and $R^{7a}$ is —H and the other is —OH, $R^5$ is —H, —OH, or -OTBS, and X is =N—OH, =N—OR$^{3j}$, or =N—NHMe, where $R^{3j}$ is alkyl such as methyl, ethyl, propyl, butyl, etc.

In embodiments of formula (IB-a), (IB-b), (IB-c), and (IB-d), $R^7$ and $R^{7a}$ are —H, $R^5$ is —H or —OH, and X is =N—OH, =N—OR$^{3j}$, or =N—NHMe, where $R^{3j}$ is alkyl such as methyl, ethyl, propyl, butyl, etc.

In embodiments of formula (IB-a), (IB-b), (IB-c), and (IB-d), $R^5$ is —H or —OH, X is =CH$_2$ or =O, and $R^7$ and $R^{7a}$ together form =O.

In embodiments of formula (IB-a), (IB-b), (IB-c), and (IB-d), $R^7$ and $R^{7a}$ are —OH and —H, respectively (or, they are both —H), $R^5$ is —H or —OH, and X is =C($R^{3b}$)($R^{3c}$), where $R^{3b}$ and $R^{3c}$ are independently selected from —H, —CN, and alkyl.

In each of the above oxime and alkene compounds for formula (IB-a), (IB-b), (IB-c), and (IB-d), the oxime/alkene may exist as a racemic mixture of two isomers, or may be present as a single isomer. Isolation of single isomers is generally within the skill in the art.

In embodiments of formula (IB-a), (IB-b), (IB-c), and (IB-d), $R^5$ is —OH or —H, X is =O and $R^7$ and $R^{7a}$ are both H.

In any of the foregoing embodiments of formula (IB-a), (IB-b), (IB-c), and (IB-d), $R^7$ and $R^{7a}$ may alternatively together form =O, or may alternatively both be —H.

In embodiments, the compounds have the structure of formula (IC-a), (IC-b), (IC-c), or (IC-d)

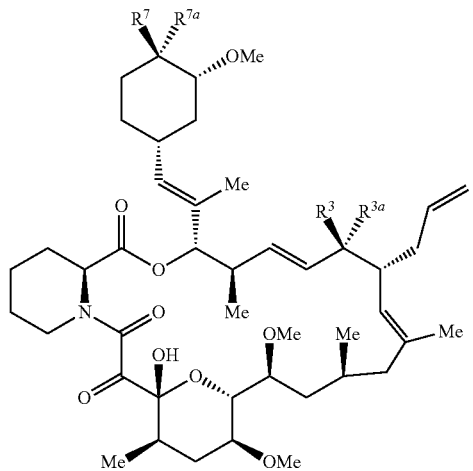

(IC-a)

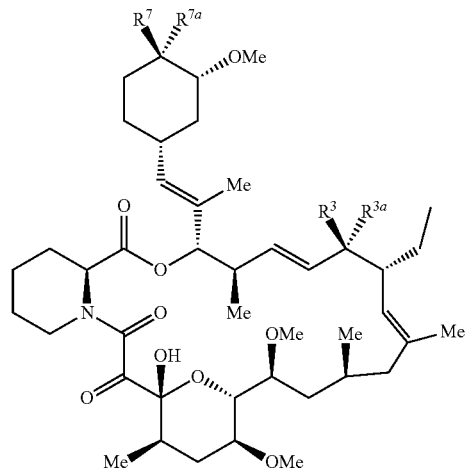

(IC-b)

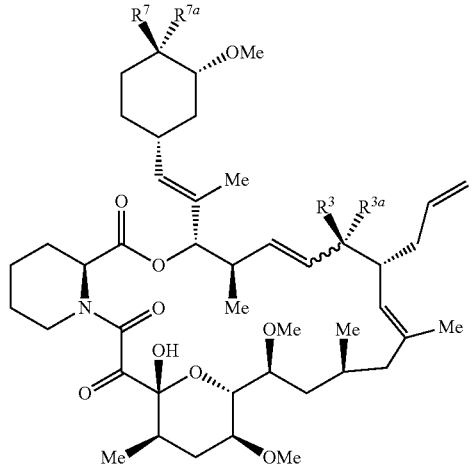

(IC-c)

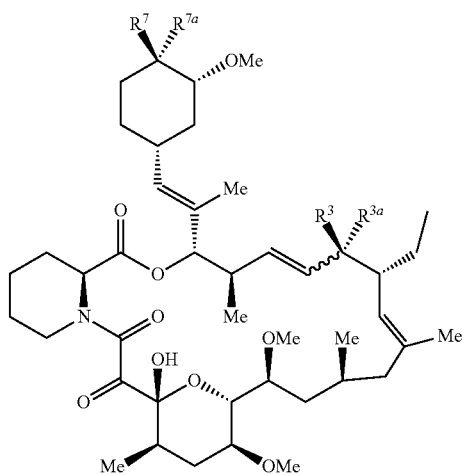

(IC-d)

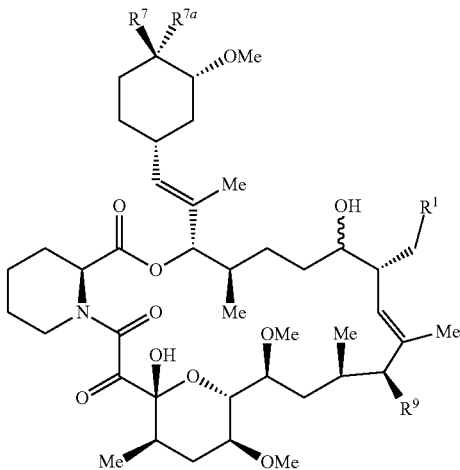

(IE)

In Formula (IC-a), (IC-b), (IC-c), and (IC-d), $R^3$, $R^{3a}$, $R^7$, and $R^{7a}$ are as defined in Formula (I). In embodiments, $R^3$ and $R^{3a}$ together form =O, one of $R^7$ and $R^{7a}$ is —H, and the other is selected from —OH, alkoxy, alkylcarboxy, alkenylcarboxy, and substituted versions thereof.

For example, in formula (IC-a), (IC-b), (IC-c), and (IC-d), $R^3$ and $R^{3a}$ together form =O, $R^{7a}$ is —H, and $R^7$ is —OH or —O—C(=O)—$R^{7c}$, where $R^{7c}$ is —(CH$_2$)$_n$—COOH or —(CH$_2$)$_n$—CH=CHR$^{7d}$ (n is 1, 2, or 3), and $R^{7d}$ is —H, alkyl (e.g., methyl, ethyl, etc), or —COOH.

For example, in formula (IC-a), (IC-b), (IC-c), and (IC-d), $R^{7a}$ is —H, $R^7$ is —OH and $R^3$ and $R^{3a}$ together form =N—NH—$R^{7e}$, =N—OH, or =N—OR$^{7e}$, where $R^{7e}$ is alkyl (e.g., methyl or ethyl, etc.).

In embodiments, the compounds have the structure of formula (ID) or (IE)

In formula (ID) and (IE), $R^1$, $R^7$, $R^{7a}$, and $R^9$ are as defined in formula (I). The wavy line indicates that the hydroxyl substituent can be either isomer, and both isomers are intended to be included.

In embodiments of formula (ID) and (IE), $R^1$ is alkyl or alkenyl, $R^{7a}$ and $R^9$ are —H, and $R^7$ is selected from alkoxy, alkylcarboxy, alkenylcarboxy, and substituted versions thereof. For example, $R^1$ is methyl, $R^{7a}$ and $R^9$ are —H, and $R^7$ is —OC(=O)—(CH$_2$)$_n$—COOH (n is 1, 2, or 3). For example, $R^1$ is —CH=CH$_2$, $R^{7a}$ and $R^9$ are —H, and $R^7$ is —OC(=O)—(CH$_2$)$_n$—COOH (n is 1, 2, or 3). For example, $R^1$ is methyl, $R^{7a}$ and $R^9$ are —H, and $R^7$ is —OH. For example, $R^1$ is —CH=CH$_2$, $R^{7a}$ and $R^9$ are —H, and $R^7$ is —OH.

In embodiments of formula (ID) and (IE), $R^1$ is alkyl or alkenyl, $R^{7a}$ is —H, and $R^7$ and $R^9$ are both hydroxyl. For example, $R^1$ is methyl. For example, $R^1$ is —CH=CH$_2$.

In embodiments the compounds have the structure of formula (IF-a) or (IF-b)

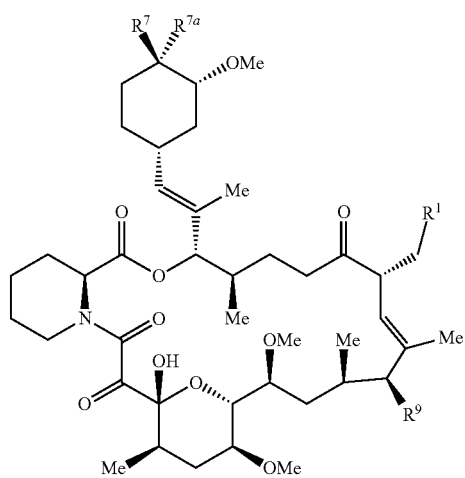

(ID)

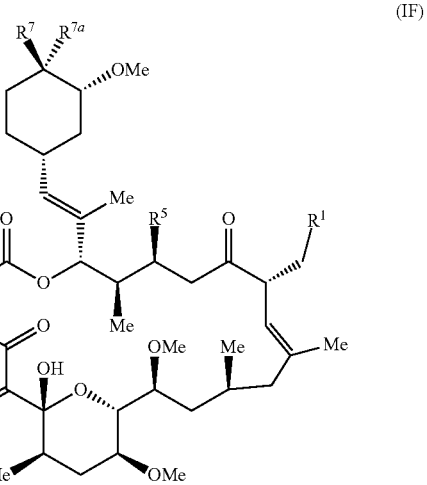

(IF)

In formula (IF), $R^1$, $R^5$, $R^7$, and $R^{7a}$ are as defined in formula (I).

In embodiments of formula (IF), $R^1$ is alkyl or alkenyl, $R^5$ is —OH, $R^7$ is H, and $R^{7a}$ is amine. For example, $R^1$ is methyl, $R^5$ is —OH, $R^7$ is H, and $R^{7a}$ is —NH$_2$. For example, $R^1$ is —CH=CH$_2$, $R^5$ is —OH, $R^7$ is H, and $R^{7a}$ is —NH$_2$. For example, $R^1$ is methyl or —CH=CH$_2$, $R^5$ is —OH, $R^{7a}$ is H, and $R^7$ is —NH$_2$.

In embodiments of formula (IF), $R^1$ is alkyl or alkenyl, $R^5$ is -OTBS, $R^7$ is H, and $R^{7a}$ is amine. For example, $R^1$ is methyl, $R^5$ is -OTBS, $R^7$ is H, and $R^{7a}$ is —NH$_2$. For example, $R^1$ is —CH=CH$_2$, $R^5$ is -OTBS, $R^7$ is H, and $R^{7a}$ is —NH$_2$. For example, $R^1$ is methyl or —CH=CH$_2$, $R^5$ is-OTBS, $R^{7a}$ is H, and $R^7$ is —NH$_2$. Also for example, $R^1$ is methyl or —CH=CH$_2$, $R^5$ is -OTBS, $R^{7a}$ is H, and $R^7$ is —H.

In embodiments of formula (IF), $R^1$ is alkyl or alkenyl, $R^5$ is —OH, and $R^7$ and $R^{7a}$ are —H. For example, $R^1$ is methyl or —CH=CH$_2$, $R^5$ is —OH, and $R^7$ and $R^{7a}$ are —H.

In embodiments of formula (IF), $R^1$ is alkyl or alkenyl, $R^5$ is —OH, and $R^7$ and $R^{7a}$ are thiocarbonato and —H, respectively. For example, $R^1$ is methyl or —CH=CH$_2$, $R^5$ is —OH, $R^{7a}$ is H, and $R^7$ is —O—C(=S)—O-alkyl or —O—C(=S)—O-aryl. For example, $R^7$ is —O—C(=S)—O-methyl or —O—C(=S)—O-Ph.

In embodiments of formula (IF), $R^5$ is —OH, and $R^7$ and $R^{7a}$ together form =O, and $R^1$ is selected from alkenyl. For example, $R^5$ is —OH, and $R^7$ and $R^{7a}$ together form =O, and $R^1$ is —CH=CH—(CH$_2$)$_n$—$R^{7f}$, where n is 1, 2, 3, 4, 5, or greater than 5, and $R^{7f}$ is methyl, —OH, alkoxy, or aryloxy. For example, $R^5$ is —OH, and $R^7$ and $R^{7a}$ together form =O, and $R^1$ is selected from —CH=CH—(CH$_2$)$_n$—O—$R^{7g}$, where n is 1, 2, 3, or 4, and $R^{7g}$ is methyl, —OH, —OMe, or —OPh.

In embodiments of formula (IF), $R^5$ is —OH, and $R^7$ and $R^{7a}$ are —OH and —H, respectively, and $R^1$ is selected from alkyl and alkenyl. For example, $R^1$ is methyl or —CH=CH$_2$.

In embodiments, the compounds have the structure of formula (IG)

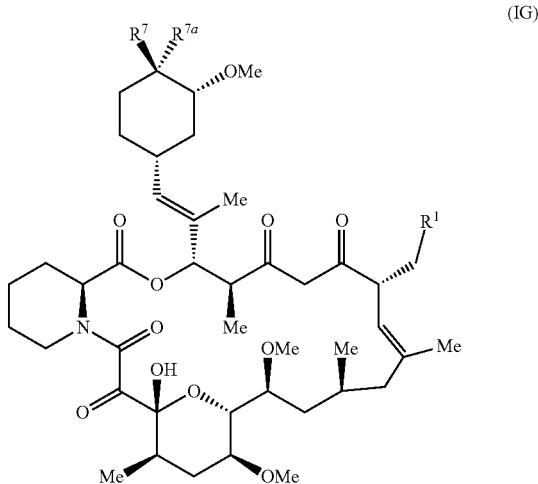

(IG)

In formula (IG), $R^1$, $R^7$, and $R^{7a}$ are as defined in formula (I).

For example, $R^1$ is selected from alkyl and alkenyl, one of $R^7$ and $R^{7a}$ is —H, and the other is selected from —H and —OH. For example, $R^7$ is —OH, $R^{7a}$ is —H, and $R^1$ is methyl, or —CH=CH$_2$. Also for example, $R^7$ and $R^{7a}$ together form =O, and $R^1$ is selected from alkyl and alkenyl (e.g., -Me, —CH=CH$_2$, etc.). Also for example, both $R^7$ an $R^{7a}$ are —H.

In embodiments, the compounds have the structure of formula (IH)

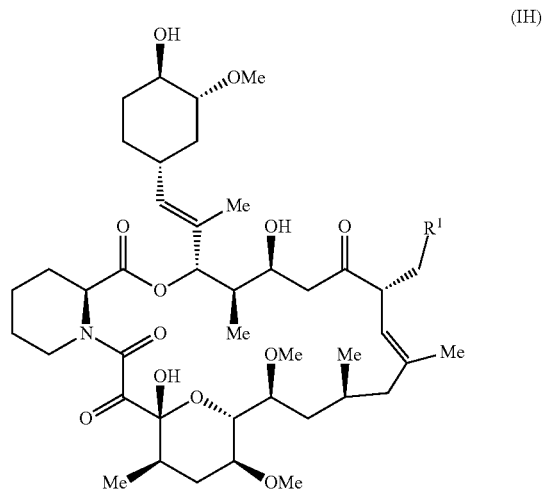

(IH)

In formula (IH), $R^1$ is as defined in formula (I).

For example, $R^1$ is alkyl, including substituted methyl. For example, $R^1$ is methyl, —C(=O)-Me, —C(=O)—OH or —CHR$^{1a}$R$^{1b}$, wherein one of $R^{1a}$ and $R^{1b}$ is —H and the other is selected from —H, carboxylic acid, and alkylcarbonyl such as —C(=O)Me or —C(=O)Et.

For example, R1 is alkenyl, including substituted alkenyl. Examples include —CH=CH$_2$, —CH=CH(CH$_3$) (E and Z configuration), —CH=C(CH$_3$)$_2$, and —CH=CH(R$^{1e}$) wherein $R^{1e}$ is alkyl. Examples of $R^{1e}$ include —(CH$_2$)$_n$—R$^{1f}$ (where n is in the range 1-20, or 1-10, and $R^{1f}$ is Me or —OH), acetals, alkyl groups substituted with sufone and sulfonyloxy groups, alkyl groups substituted with ester or carbonyloxy groups, cyclic alkyl groups including heterocyclic alkyl groups, aryl groups including heterocyclic aryl groups, heteroatoms substituted with alkyl groups, ketone groups, amide groups, bicyclic groups including bicyclic aromatic and bicyclic heteroatom-containing groups, and the like.

Unless otherwise specified, reference to "formula (I)" includes all sub-formulae of formula (I) (i.e., IA-a, IA-b, IA-c, IB-a, IB-b, etc.).

Included are salts (e.g., pharmaceutically acceptable salts) of the compounds of formula (I). Examples of salts are halo salts (e.g., chloride, fluoride, bromide, or iodide salts), fluorinated salts such as perfluoroacetic acid (CF$_3$COOH) salt, acetic acid salt, and the like.

Examples of specific compounds according to formula (I) are given in Table 1.

In an aspect, the compounds are useful in treating a fungal infection in a patient. Patients include human patients as well as non-human patients (e.g., domesticated animals and the like).

In an aspect, a patient suffering from a fungal infection is treated with a formulation containing at least one compound according to a formula herein.

Examples of fungal infections suitable for treatment by formulations described herein include Candida, Aspergillus, Microsporum, Trichophyton, Cryptococcus, and Epidermophyton.

The compounds disclosed herein may be used as a pharmaceutically active compound to prepare a pharmaceutically active formulation. Such formulation may further comprise additives such as pharmaceutically acceptable carriers, colorants, flavorants, binders, etc., and may further comprise coatings (if in solid dosage form), solvents (if in liquid oral, spray, or injectable form), and the like.

The total daily dose of the described compounds administered to a patient may range from about 0.001 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

In embodiments, the formulation comprises a second antifungal agent. The second antifungal agent may be another compound according to the formulae herein. In embodiments, the second antifungal agent is a known antifungal and not a compound according to the formulae herein, such as a polyene, imidazole, triazole, thiazole, allylamine, echinocandin, among others. Examples include Amphotericin B, Candicidin, Filipin, Hamycin, Natamycin, Nystatin, Rimocidin, Bifonazole, Butoconazole, Clotrimazole, econazole, fenticonazole, isoconazole, kentoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, polygodial, tolnaftate, undecylenic acid, and crystal violet, among others.

TABLE 1

Antifungal Compounds

2

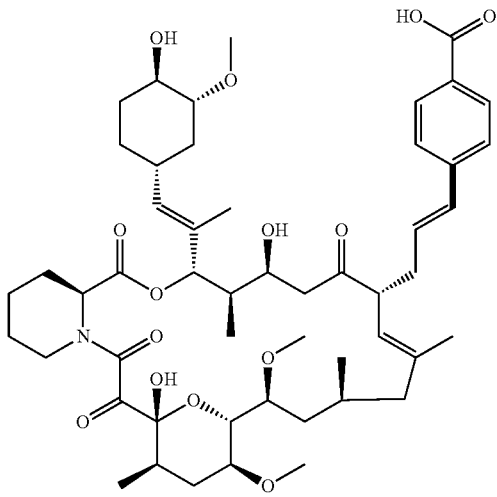

$C_{51}H_{73}NO_{14}$

3

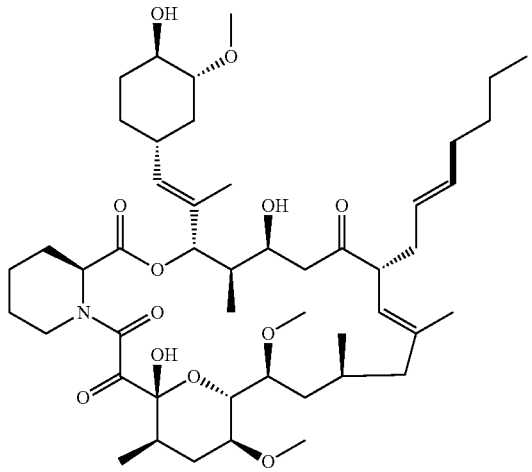

$C_{48}H_{77}NO_{12}$

TABLE 1-continued
Antifungal Compounds
4
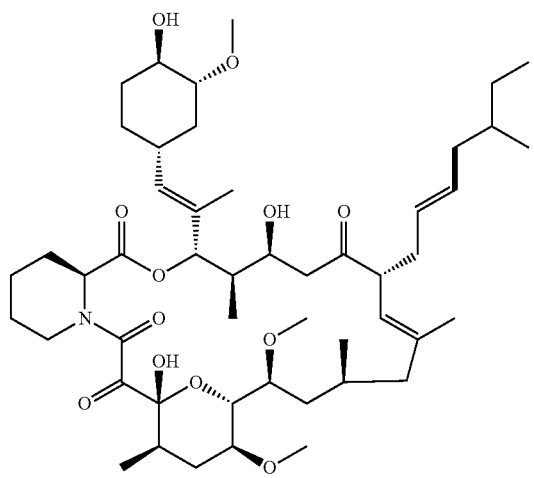
$C_{49}H_{79}NO_{12}$
5
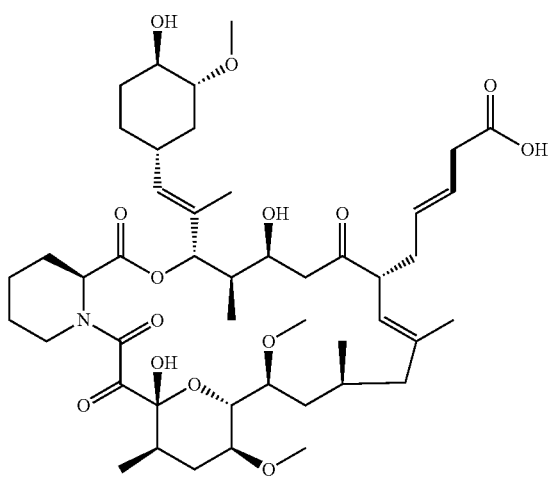
$C_{46}H_{71}NO_{14}$
6
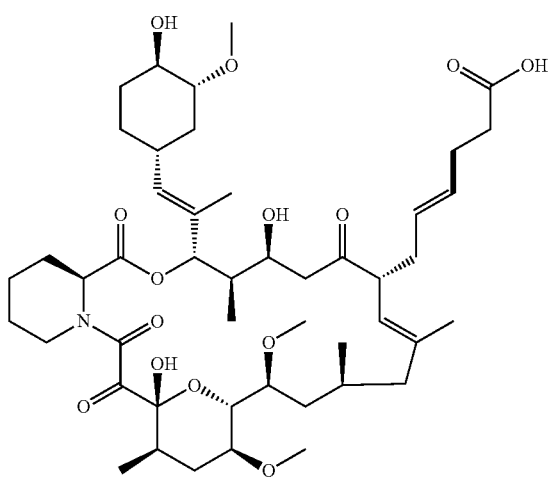
$C_{47}H_{73}NO_{14}$ TABLE 1-continued
Antifungal Compounds
7
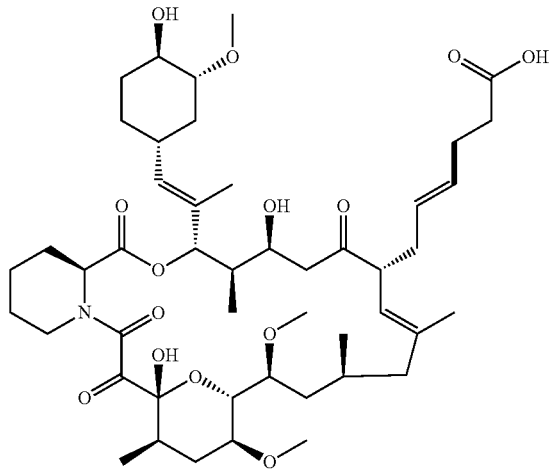
$C_{47}H_{73}NO_{14}$
8
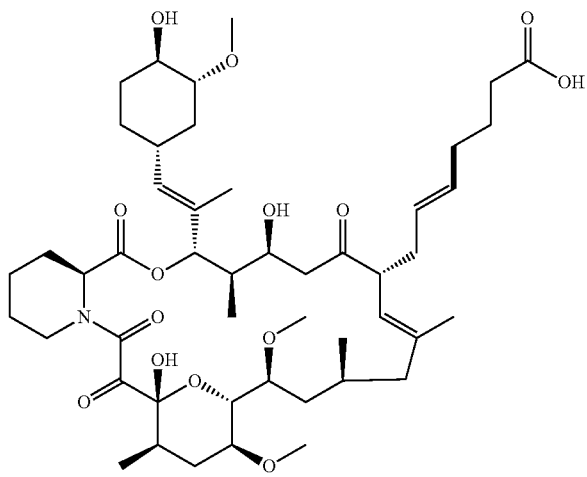
$C_{48}H_{75}NO_{14}$
9
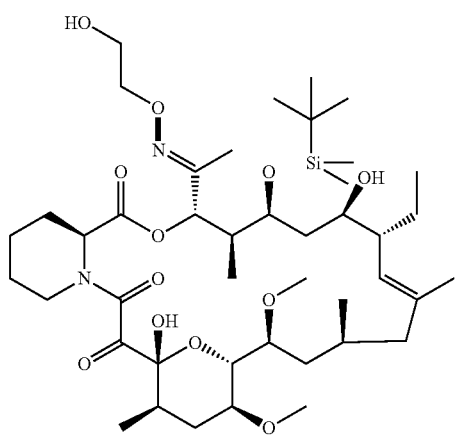
$C_{43}H_{76}N_2O_{12}Si$ TABLE 1-continued
Antifungal Compounds
10
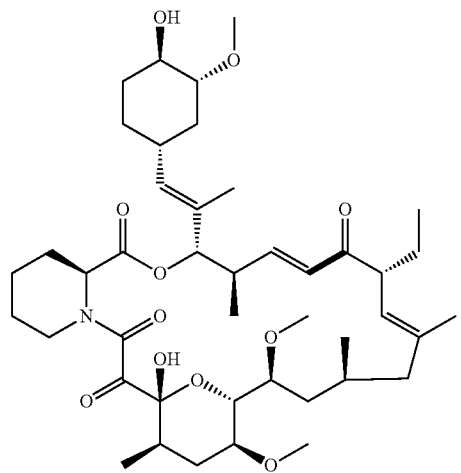
$C_{43}H_{67}NO_{11}$
11
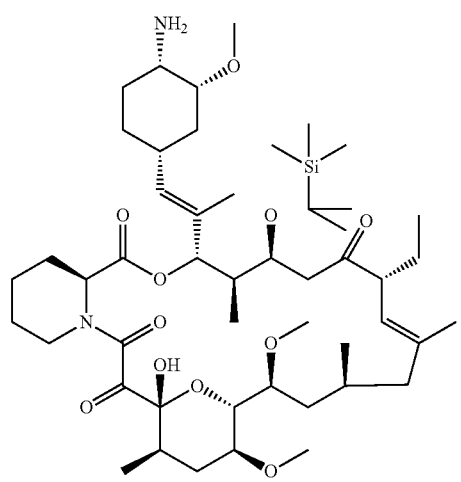
$C_{49}H_{84}N_2O_{11}Si$
12
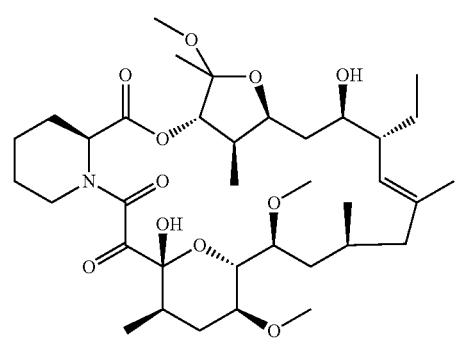 [SMILES: CC[C@@H]1/C=C(\C)C[C@H](C)C[C@H](OC)[C@H]2O[C@@](O)(C(=O)C(=O)N3CCCC[C@H]3C(=O)O[C@H]3[C@H](C)[C@H](C[C@H]1O)OC3(C)OC)[C@H](C)C[C@@H]2OC]
$C_{36}H_{59}NO_{11}$ TABLE 1-continued
Antifungal Compounds
13
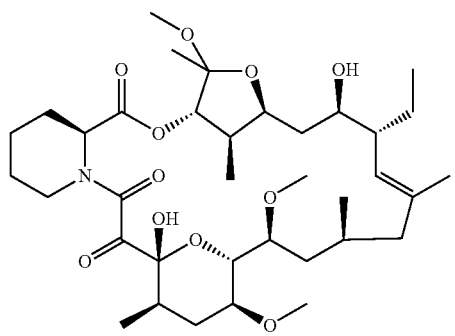 [SMILES: CC[C@@H]1/C=C(\C)C[C@H](C)C[C@H](OC)[C@H]2O[C@@](O)(C(=O)C(=O)N3CCCC[C@H]3C(=O)O[C@H]3[C@H](C)[C@H](C[C@H]1O)OC3(C)OC)[C@H](C)C[C@@H]2OC]
$C_{36}H_{59}NO_{11}$
14
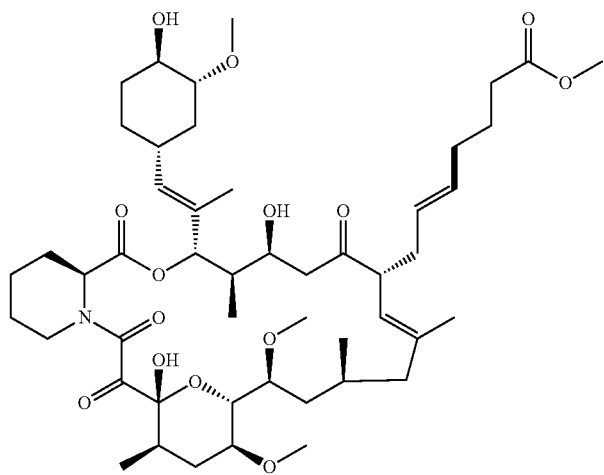
$C_{49}H_{77}NO_{14}$
15
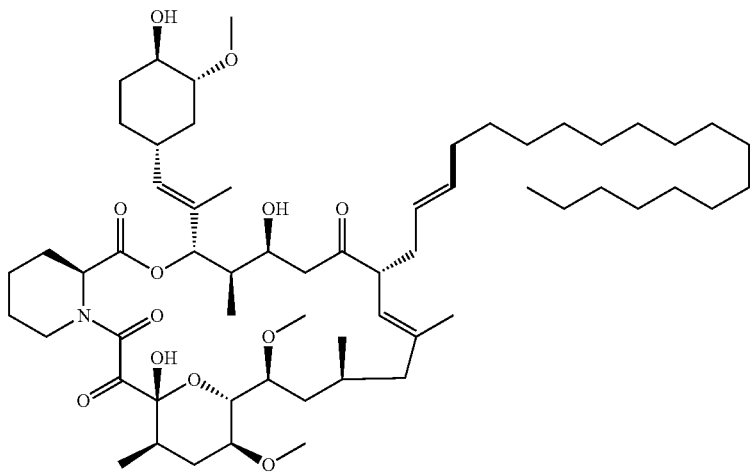
$C_{60}H_{101}NO_{12}$ TABLE 1-continued
Antifungal Compounds
16
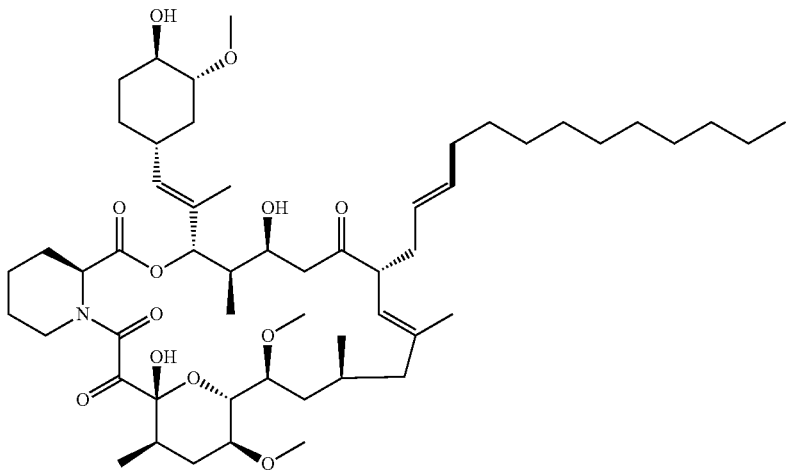
$C_{54}H_{89}NO_{12}$
17
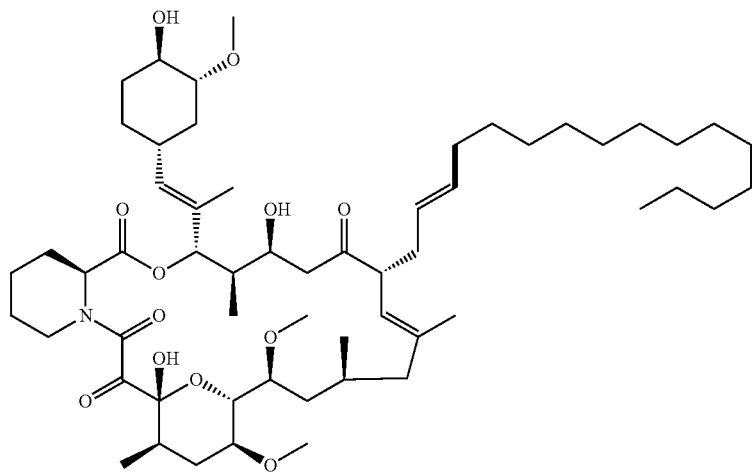
$C_{57}H_{95}NO_{12}$
18
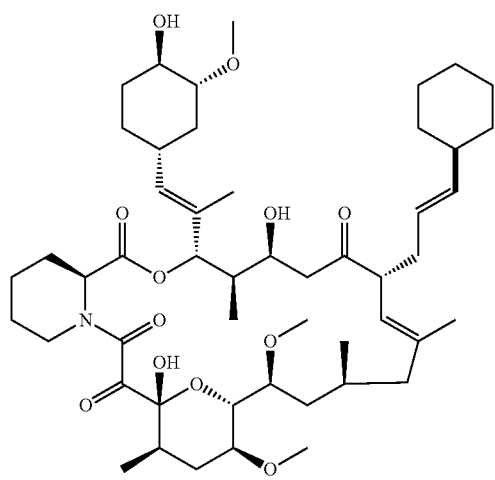
$C_{50}H_{79}NO_{12}$ TABLE 1-continued
Antifungal Compounds
19
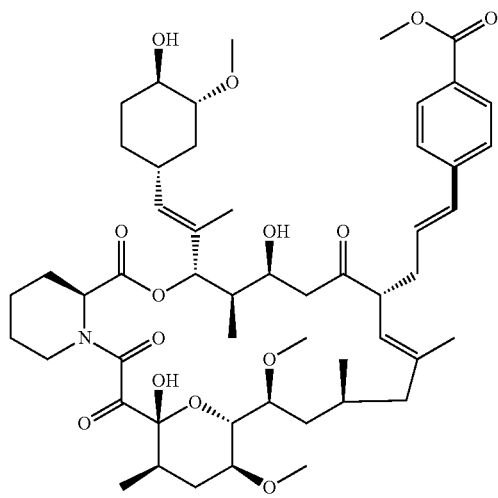
$C_{52}H_{75}NO_{14}$
20
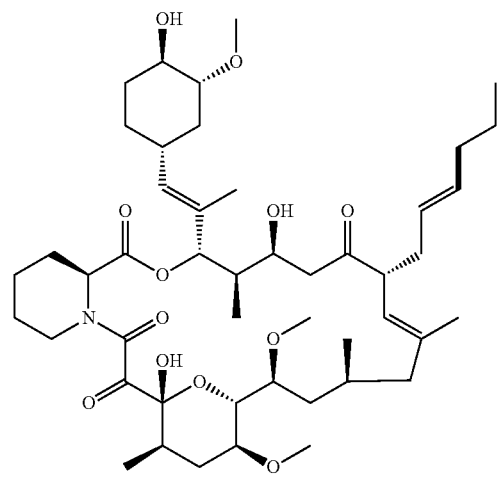
$C_{47}H_{75}NO_{12}$
21
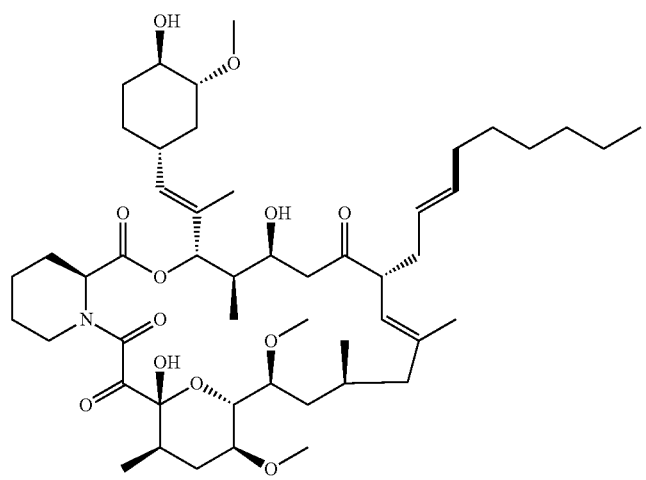
$C_{50}H_{81}NO_{12}$ TABLE 1-continued
Antifungal Compounds
22
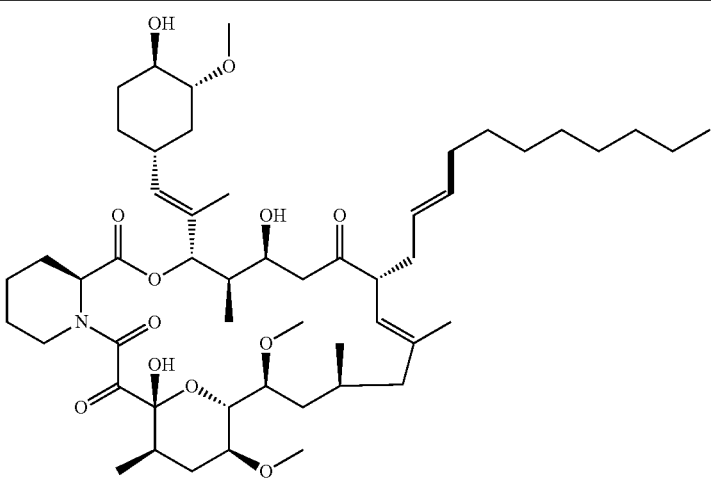
$C_{52}H_{85}NO_{12}$
23
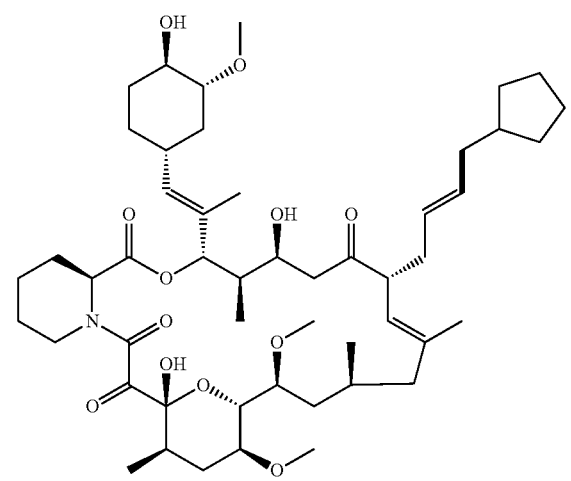
$C_{50}H_{79}NO_{12}$
24
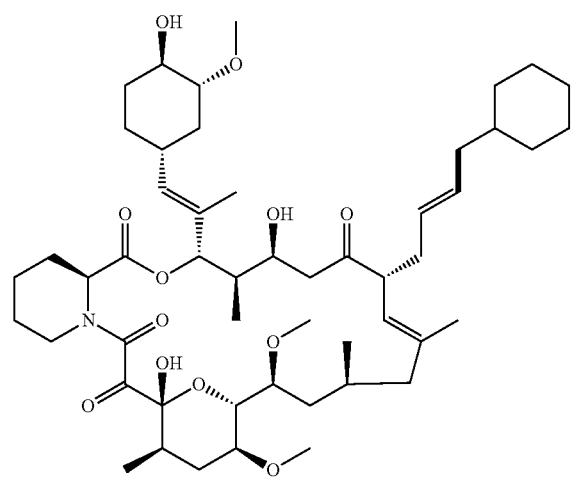
$C_{51}H_{81}NO_{12}$ TABLE 1-continued
Antifungal Compounds
25
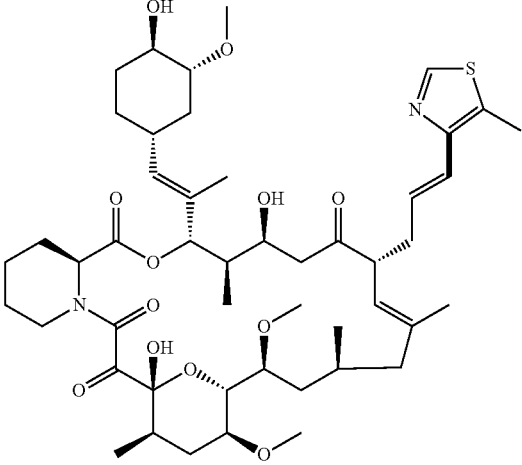
$C_{48}H_{72}N_2O_{12}S$
26
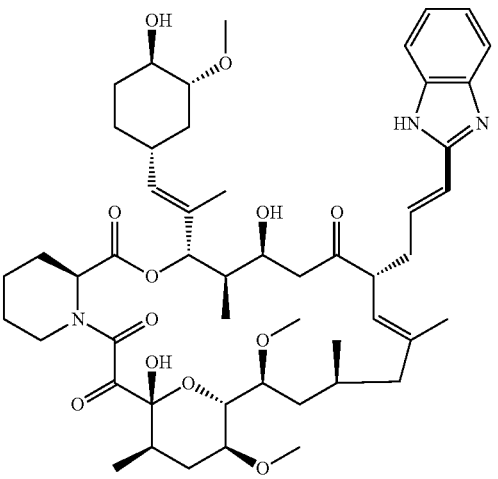
$C_{51}H_{73}N_3O_{12}$
27
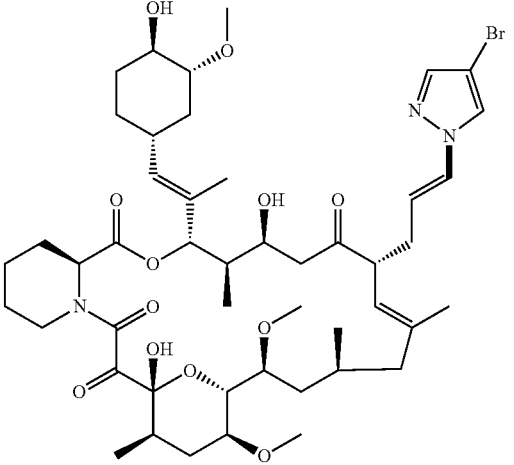
$C_{47}H_{70}BrN_3O_{12}$ TABLE 1-continued
Antifungal Compounds
28 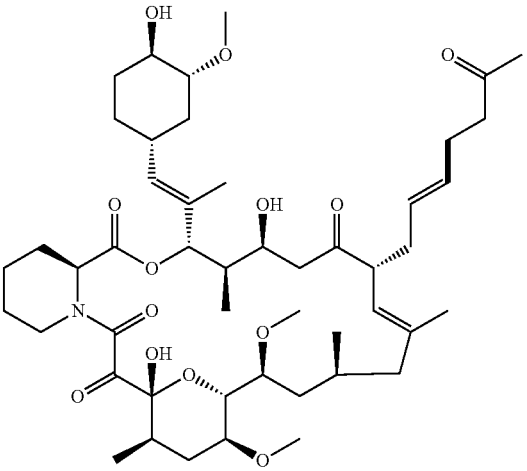
$C_{48}H_{75}NO_{13}$
29 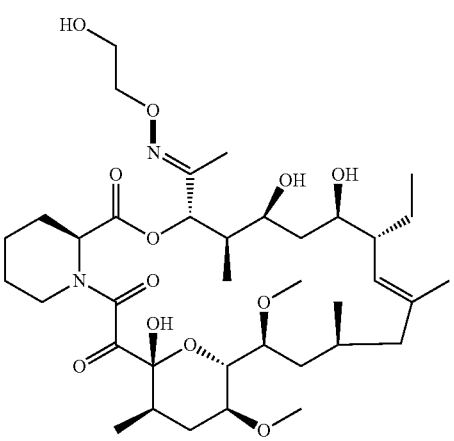
$C_{37}H_{62}N_2O_{12}$
30 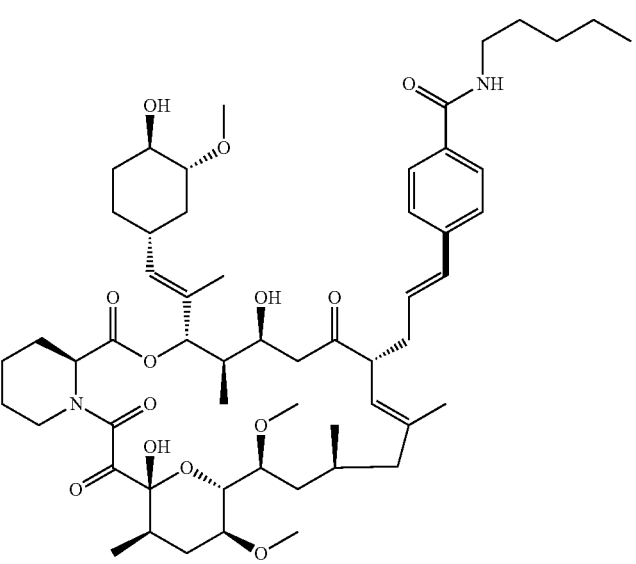
$C_{56}H_{84}N_2O_{13}$ TABLE 1-continued
Antifungal Compounds
31
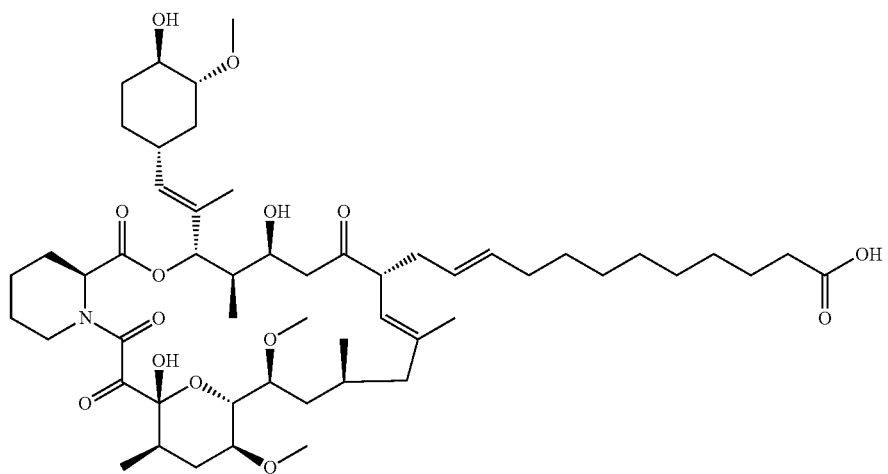 [SMILES: CO[C@H]1C[C@@H](C)C/C(C)=C/[C@@H](C/C=C/CCCCCCCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{53}H_{85}NO_{14}$
32
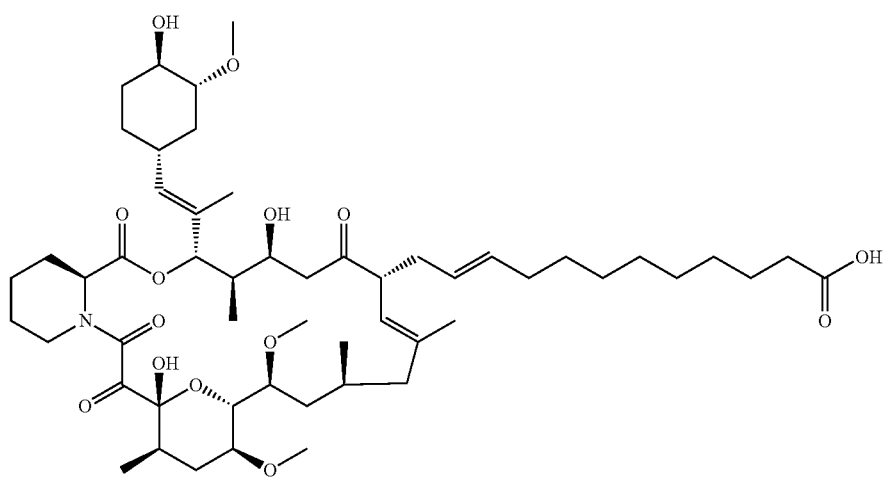 [SMILES: CO[C@H]1C[C@@H](C)C/C(C)=C/[C@@H](C/C=C/CCCCCCCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{53}H_{85}NO_{14}$
33
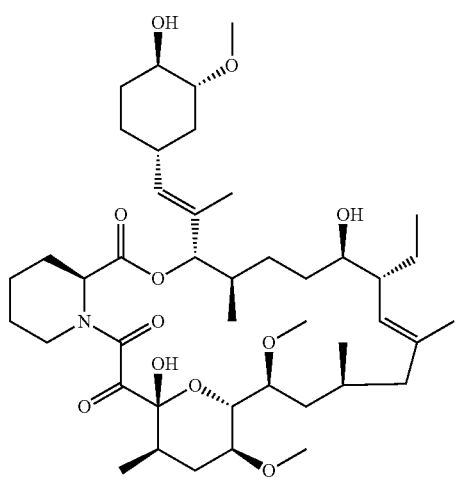 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)CC[C@H]1O)[C@H](C)C[C@@H]2OC]
$C_{43}H_{71}NO_{11}$ TABLE 1-continued
Antifungal Compounds
34
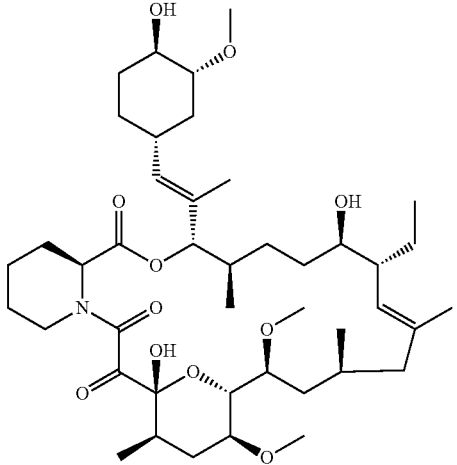 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)CC[C@H]1O)[C@H](C)C[C@@H]2OC]
$C_{43}H_{71}NO_{11}$
35
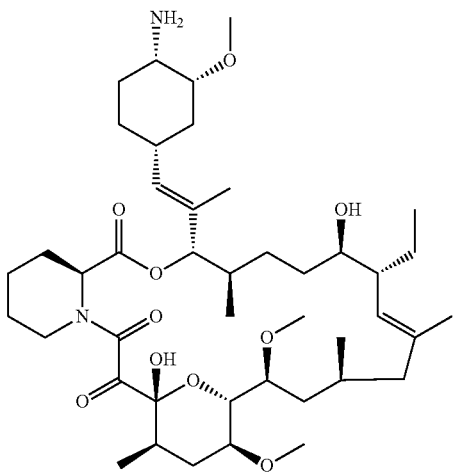 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@H](N)[C@H](OC)C3)[C@H](C)CC[C@H]1O)[C@H](C)C[C@@H]2OC]
$C_{43}H_{72}N_2O_{10}$
36
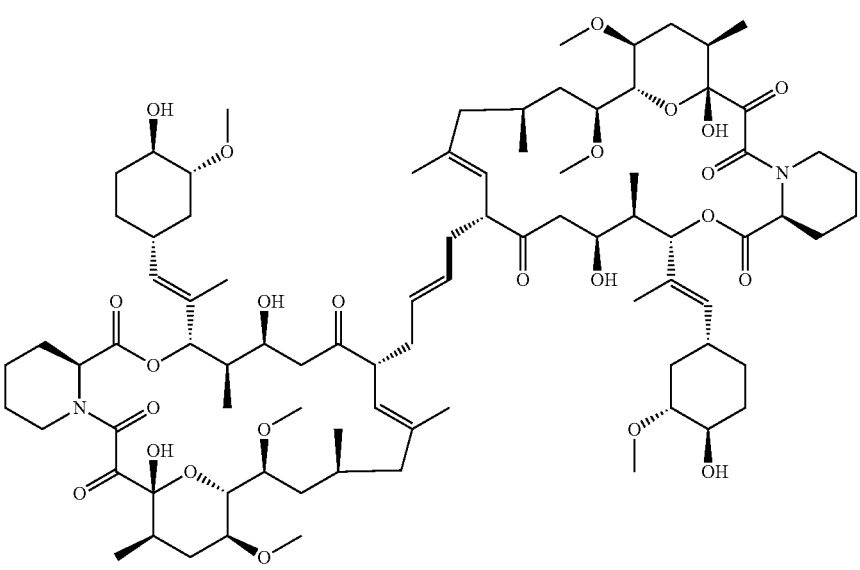
$C_{86}H_{134}N_2O_{24}$ TABLE 1-continued
Antifungal Compounds
37 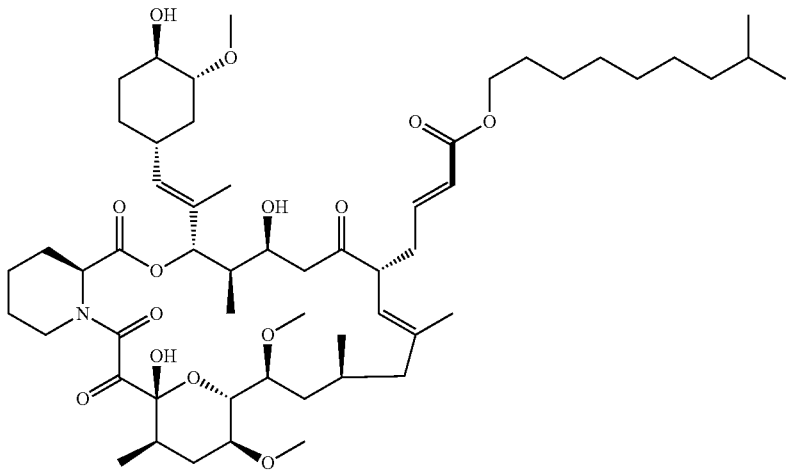
$C_{55}H_{89}NO_{14}$
38 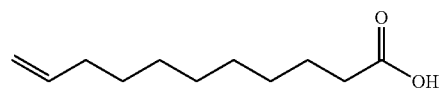
$C_{11}H_{20}O_2$
39 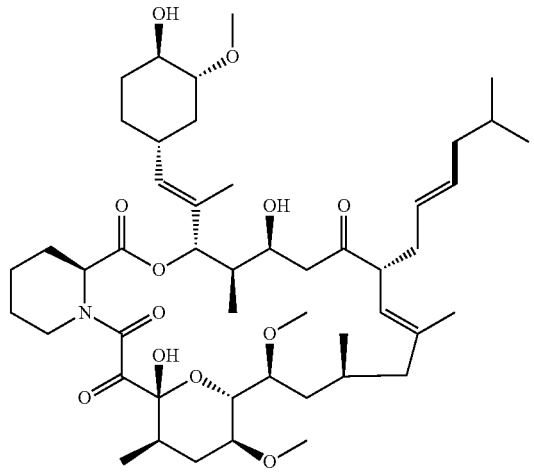
$C_{48}H_{77}NO_{12}$ TABLE 1-continued
Antifungal Compounds
40
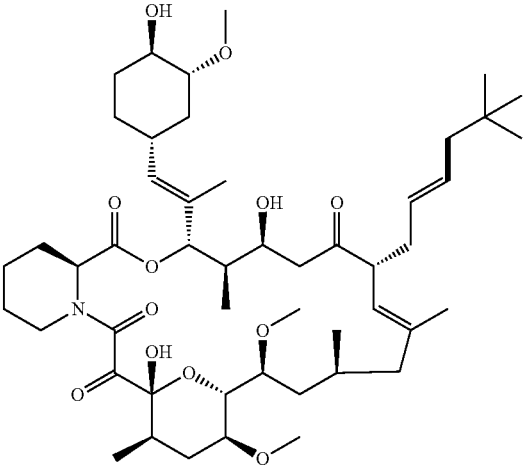
$C_{49}H_{79}NO_{12}$
41
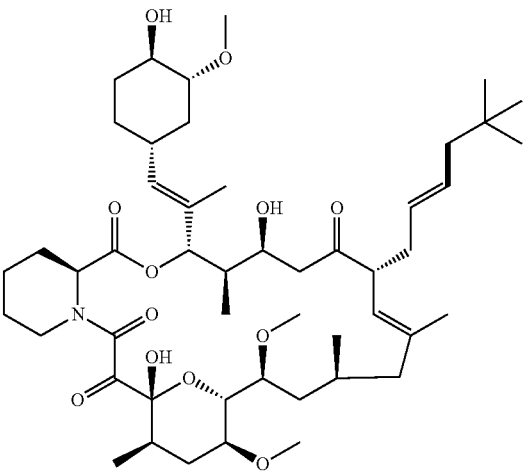
$C_{49}H_{79}NO_{12}$
42
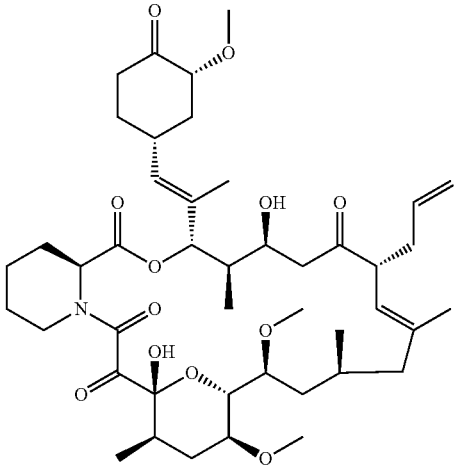 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC(=O)[C@H](OC)C3)[C@H](C)[C@@H](O)CC1=O)[C@H](C)C[C@@H]2OC]
$C_{44}H_{67}NO_{12}$ TABLE 1-continued Antifungal Compounds

43

$C_{43}H_{67}NO_{12}$

44

$C_{43}H_{69}NO_{13}$

45

$C_{43}H_{69}NO_{13}$

TABLE 1-continued
Antifungal Compounds
46 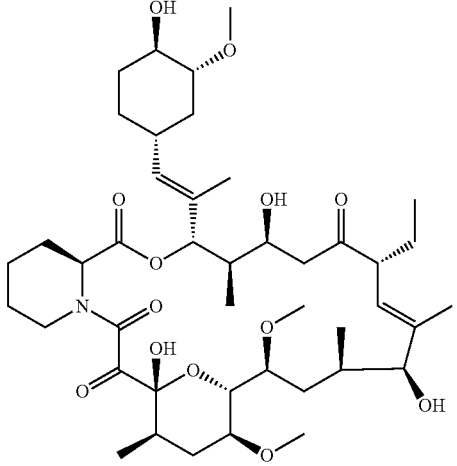 [SMILES: CC[C@@H]1/C=C(\C)[C@@H](O)[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{43}H_{69}NO_{13}$
47 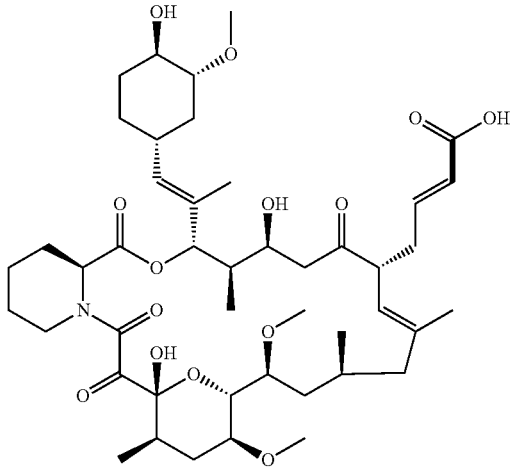
$C_{45}H_{69}NO_{14}$
48 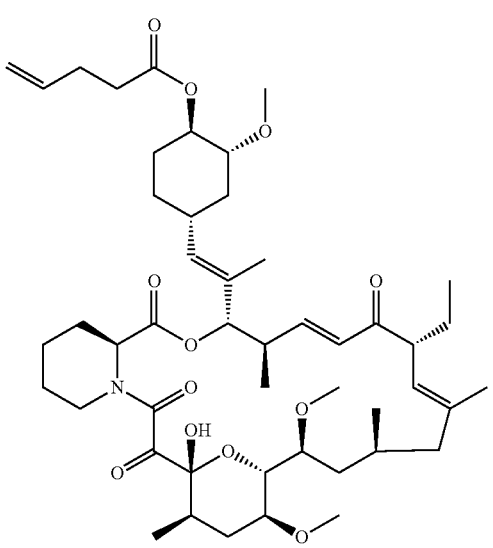 [SMILES: C=CCCC(=O)O[C@@H]1CC[C@@H](/C=C(\C)[C@H]2OC(=O)[C@@H]3CCCCN3C(=O)C(=O)[C@]3(O)O[C@H]([C@@H](OC)C[C@@H](C)C/C(C)=C/[C@@H](CC)C(=O)/C=C/[C@H]2C)[C@@H](OC)C[C@H]3C)C[C@H]1OC]
$C_{48}H_{73}NO_{12}$ TABLE 1-continued
Antifungal Compounds
49
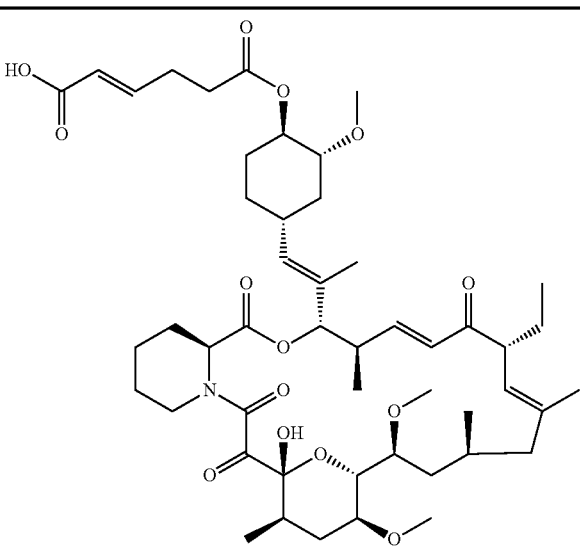
$C_{49}H_{73}NO_{14}$
50
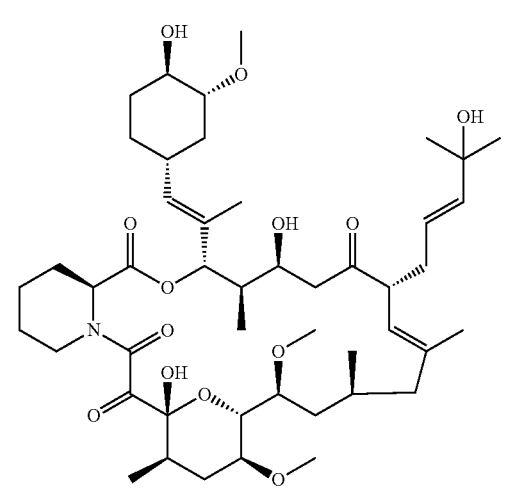 [SMILES: CO[C@H]1C[C@@H](C)C/C(C)=C/[C@@H](C/C=C/C(C)(C)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{47}H_{75}NO_{13}$
51
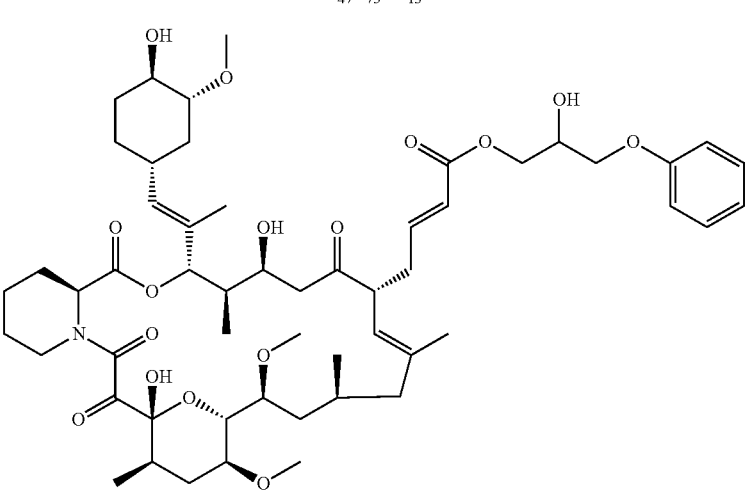
$C_{54}H_{79}NO_{16}$ TABLE 1-continued
Antifungal Compounds
52
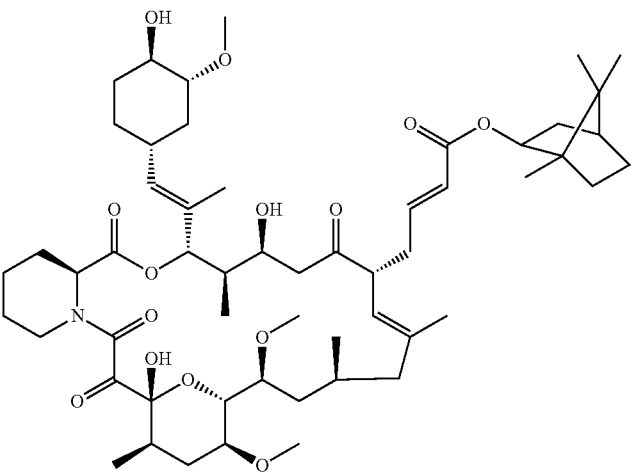 [SMILES: CO[C@H]1C[C@@H](C)C/C(C)=C/[C@@H](C/C=C/C(=O)OC2CC3CCC2(C)C3(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{55}H_{85}NO_{14}$
53
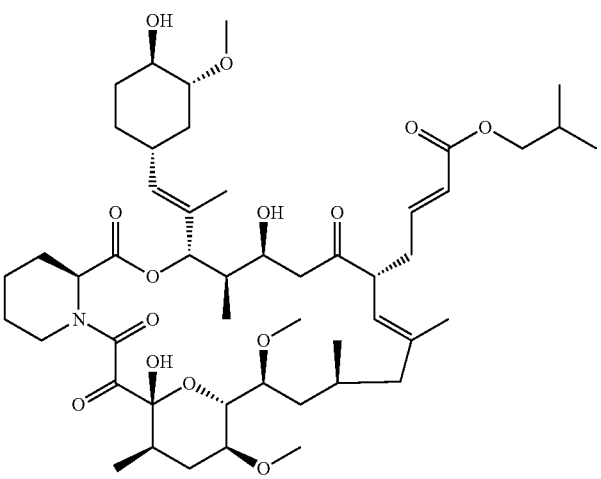 [SMILES: CO[C@H]1C[C@@H](C)C/C(C)=C/[C@@H](C/C=C/C(=O)OCC(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{49}H_{77}NO_{14}$
54
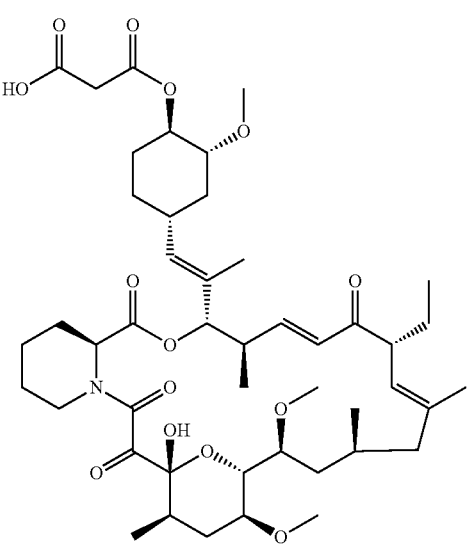 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)CC(=O)O)[C@H](OC)C3)[C@H](C)/C=C/C1=O)[C@H](C)C[C@@H]2OC]
$C_{46}H_{69}NO_{14}$ TABLE 1-continued
Antifungal Compounds
55
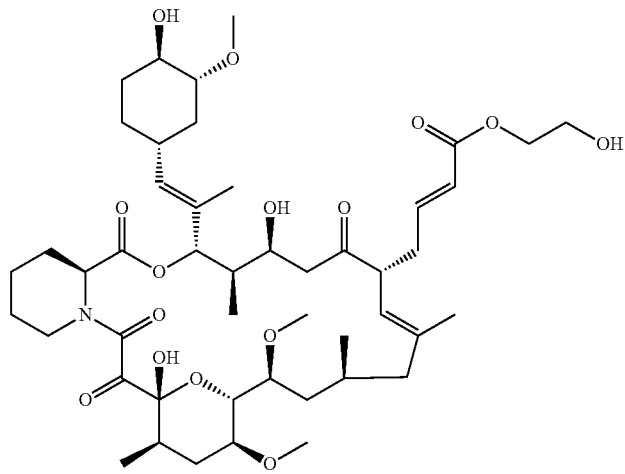 [SMILES: CO[C@H]1C[C@@H](C)C/C(C)=C/[C@@H](C/C=C/C(=O)OCCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{47}H_{73}NO_{15}$
56
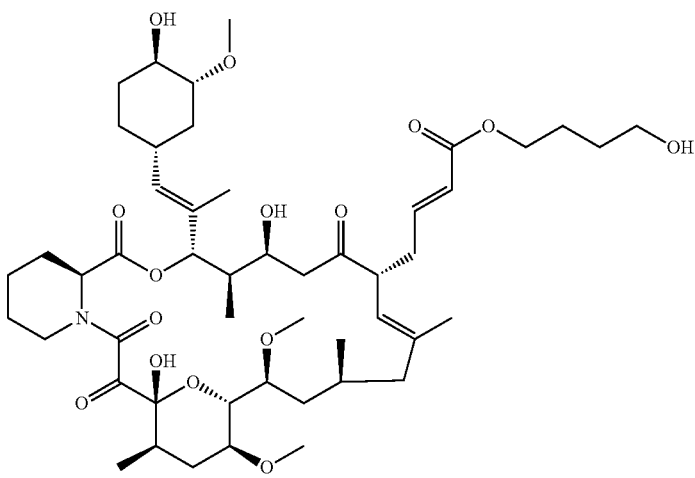 [SMILES: CO[C@H]1C[C@@H](C)C/C(C)=C/[C@@H](C/C=C/C(=O)OCCCCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{49}H_{77}NO_{15}$
57
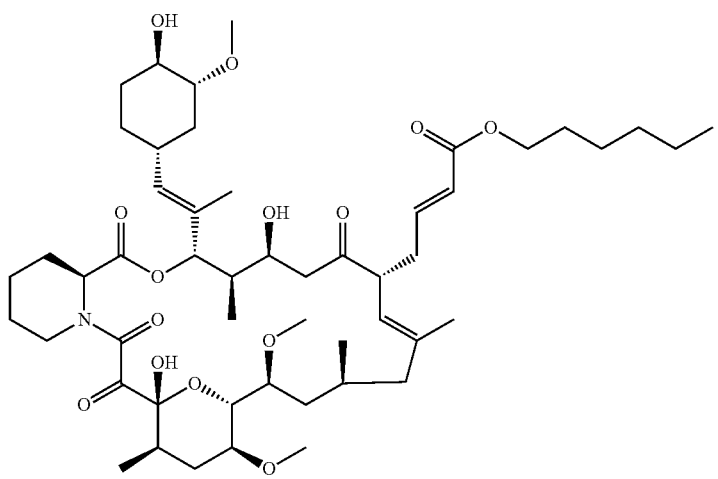 [SMILES: CCCCCCOC(=O)/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{51}H_{81}NO_{14}$ TABLE 1-continued
Antifungal Compounds
58
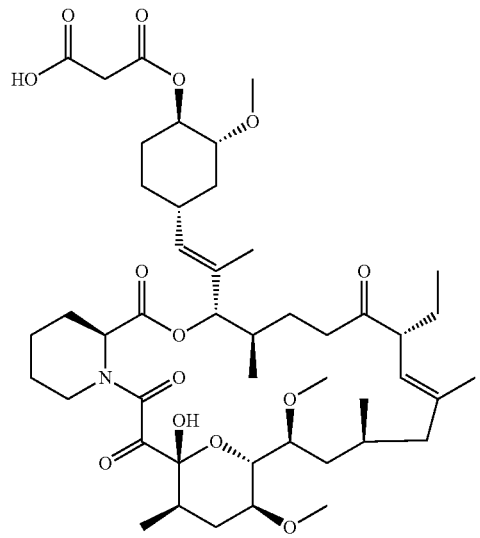 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)CC(=O)O)[C@H](OC)C3)[C@H](C)CCC1=O)[C@H](C)C[C@@H]2OC]
$C_{46}H_{71}NO_{14}$
59
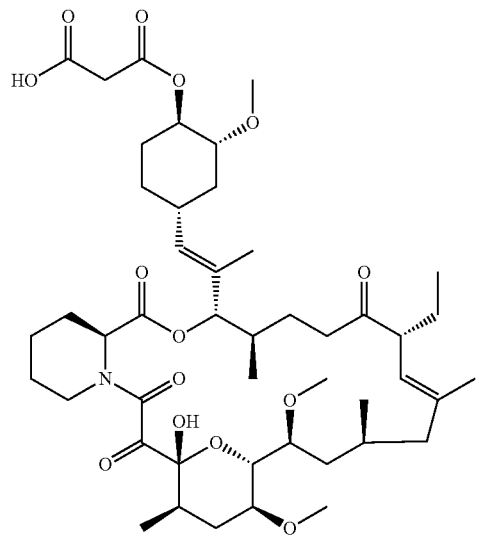 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)CC(=O)O)[C@H](OC)C3)[C@H](C)CCC1=O)[C@H](C)C[C@@H]2OC]
$C_{46}H_{71}NO_{14}$ TABLE 1-continued
Antifungal Compounds
60 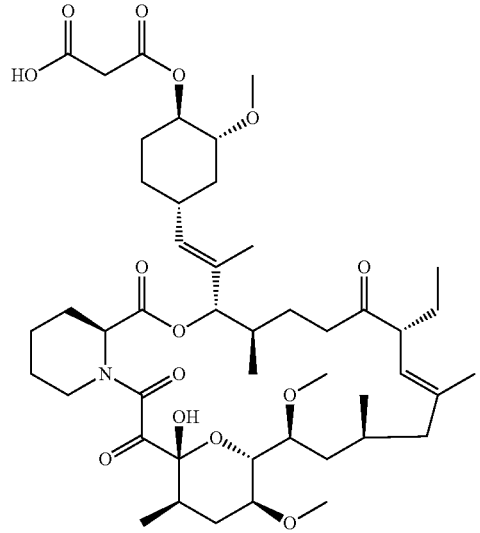 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)CC(=O)O)[C@H](OC)C3)[C@H](C)CCC1=O)[C@H](C)C[C@@H]2OC]
$C_{46}H_{71}NO_{14}$
61 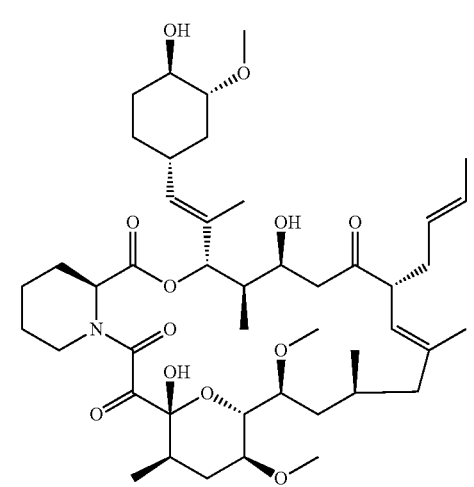 [SMILES: C/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{45}H_{71}NO_{12}$
62 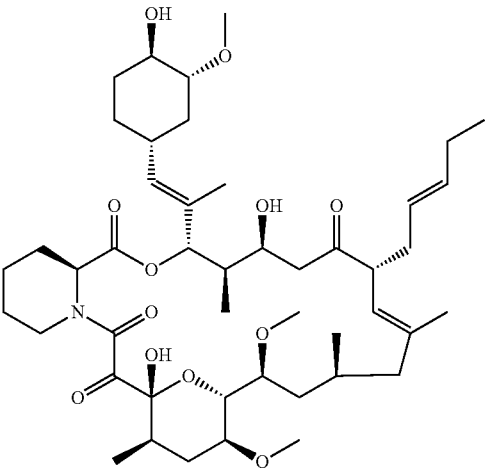 [SMILES: CC/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{46}H_{73}NO_{12}$ TABLE 1-continued
Antifungal Compounds
63
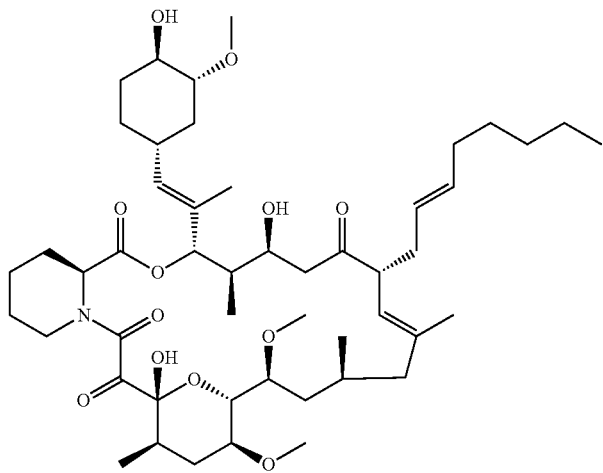 [SMILES: CCCCC/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{49}H_{79}NO_{12}$
64
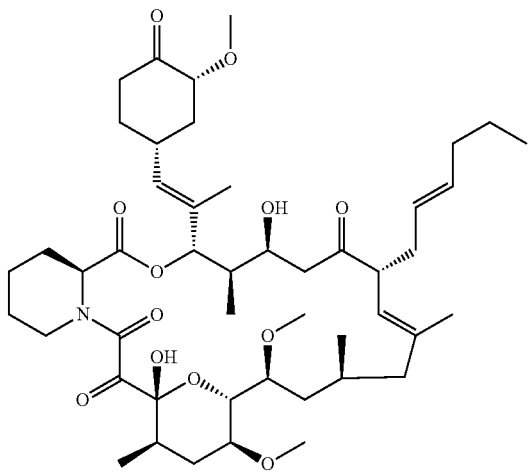 [SMILES: CCC/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC(=O)[C@H](OC)C3)[C@H](C)[C@@H](O)CC1=O)[C@H](C)C[C@@H]2OC]
$C_{47}H_{73}NO_{12}$
65
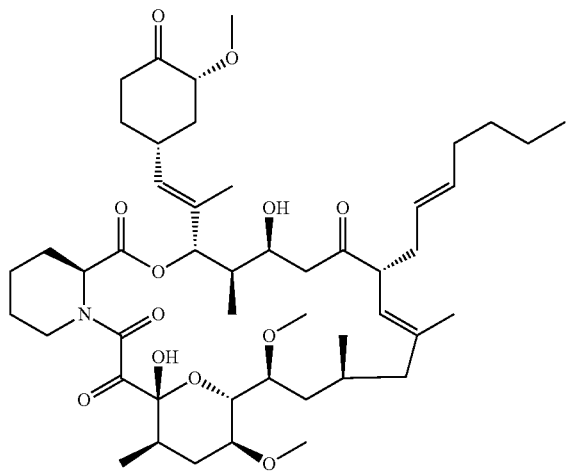 [SMILES: CCCC/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC(=O)[C@H](OC)C3)[C@H](C)[C@@H](O)CC1=O)[C@H](C)C[C@@H]2OC]
$C_{48}H_{75}NO_{12}$

TABLE 1-continued
Antifungal Compounds
66
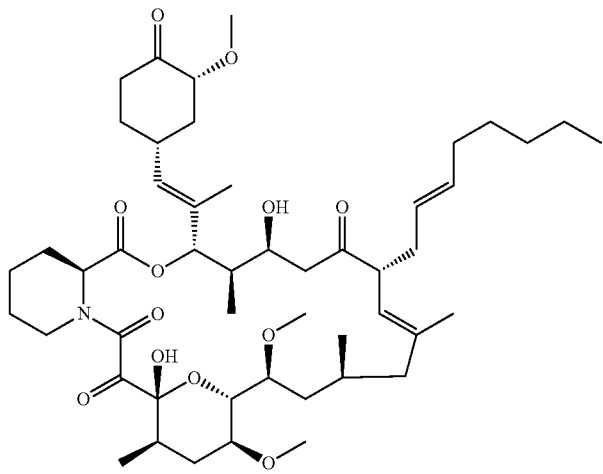 [SMILES: CCCCC/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC(=O)[C@H](OC)C3)[C@H](C)[C@@H](O)CC1=O)[C@H](C)C[C@@H]2OC]
$C_{49}H_{77}NO_{12}$
67
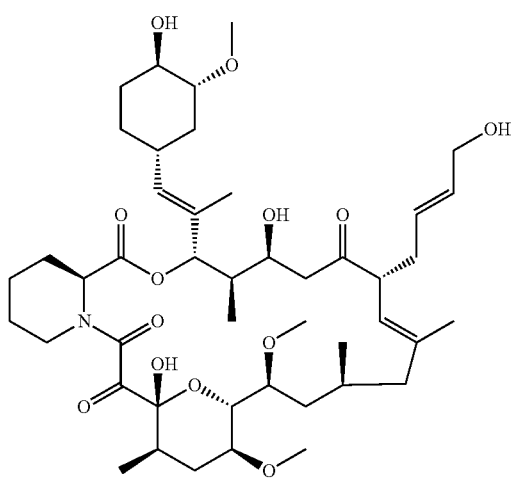 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{45}H_{71}NO_{13}$
68
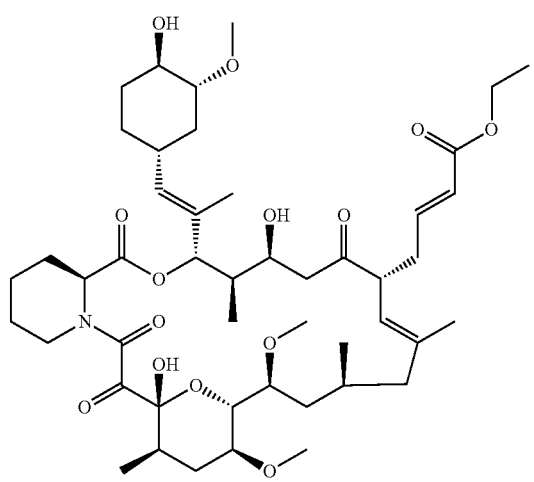 [SMILES: CCOC(=O)/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{47}H_{73}NO_{14}$ TABLE 1-continued
Antifungal Compounds
69
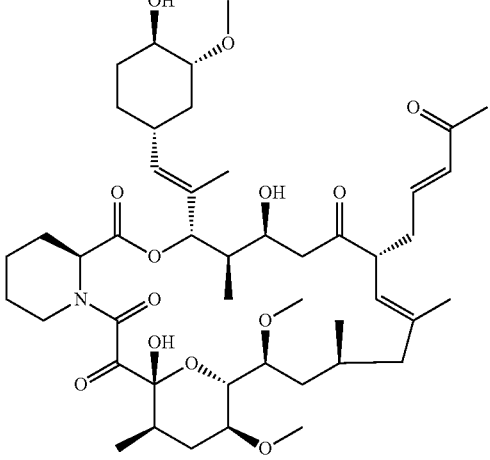
$C_{46}H_{71}NO_{13}$
70
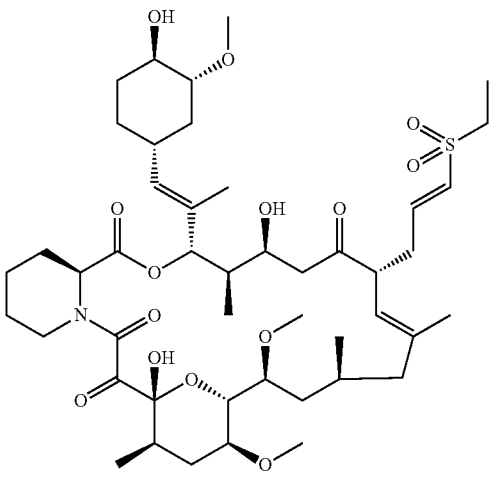 [SMILES: CCS(=O)(=O)/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{46}H_{73}NO_{14}S$
71
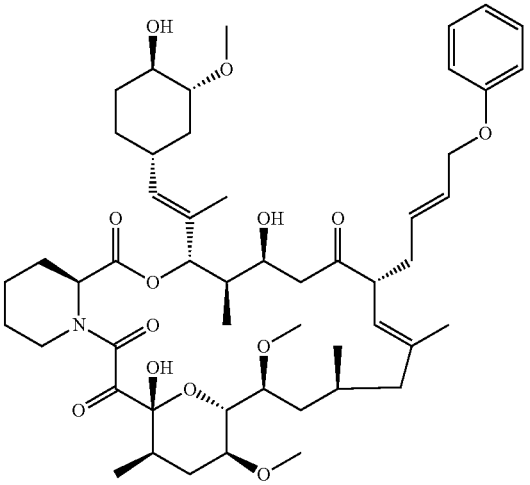 [SMILES: CO[C@H]1C[C@@H](C)C/C(C)=C/[C@@H](C/C=C/COc2ccccc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{51}H_{75}NO_{13}$ TABLE 1-continued
Antifungal Compounds
72
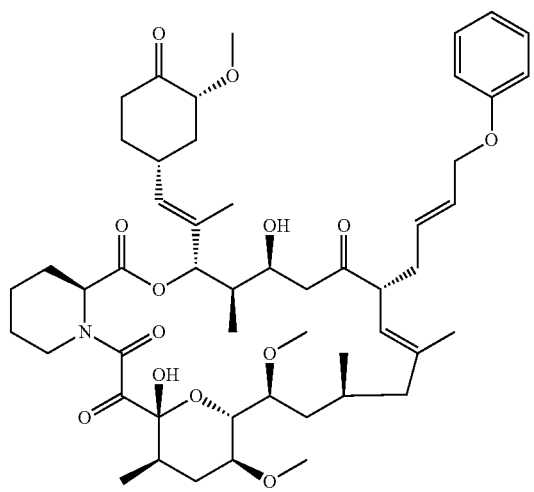 [SMILES: CO[C@H]1C[C@@H](C)C/C(C)=C/[C@@H](C/C=C/COc2ccccc2)C(=O)C[C@H](O)[C@@H](C)[C@@H](/C(C)=C/[C@@H]2CCC(=O)[C@H](OC)C2)OC(=O)[C@@H]2CCCCN2C(=O)C(=O)[C@]2(O)O[C@H]1[C@@H](OC)C[C@H]2C]
$C_{51}H_{73}NO_{13}$
73
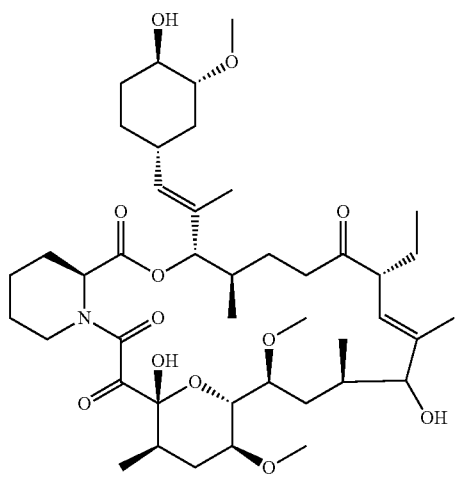 [SMILES: CC[C@@H]1/C=C(\C)C(O)[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)CCC1=O)[C@H](C)C[C@@H]2OC]
$C_{43}H_{69}NO_{12}$
74
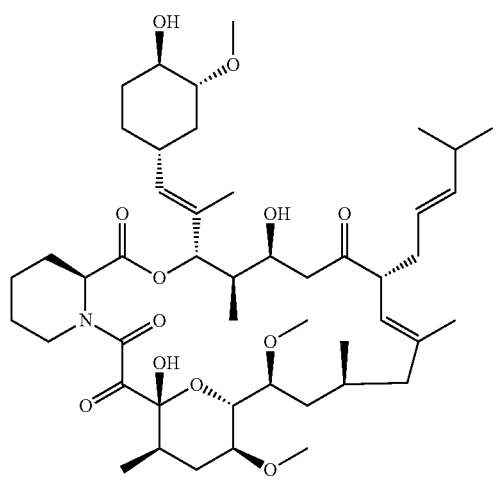
$C_{47}H_{75}NO_{12}$ TABLE 1-continued
Antifungal Compounds
75
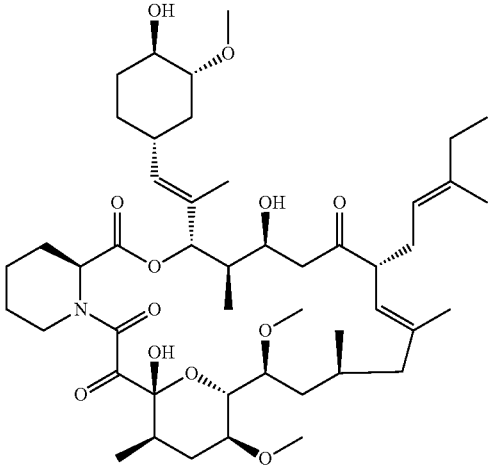 [SMILES: CC/C(C)=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{47}H_{75}NO_{12}$
76
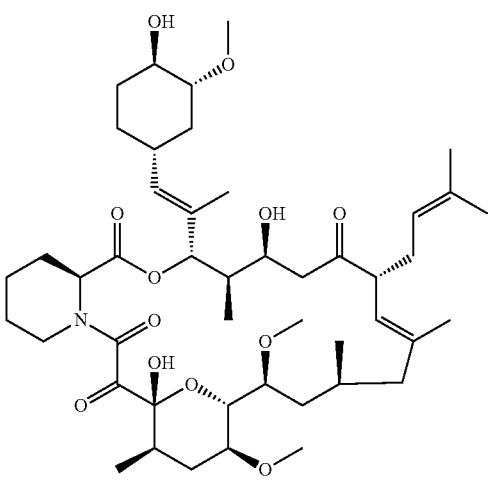 [SMILES: CO[C@H]1C[C@@H](C)C/C(C)=C/[C@@H](CC=C(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{46}H_{73}NO_{12}$
77
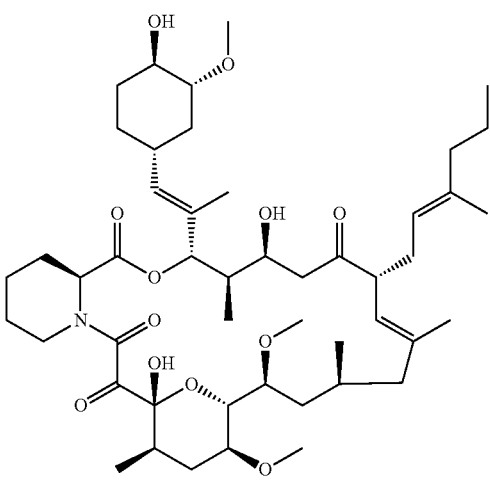 [SMILES: CCC/C(C)=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{48}H_{77}NO_{14}$ TABLE 1-continued
Antifungal Compounds
78
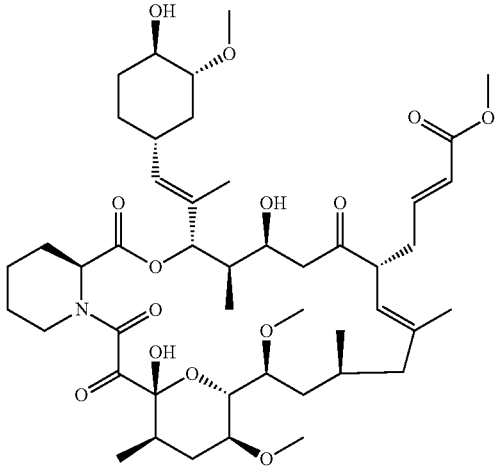 [SMILES: COC(=O)/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{46}H_{71}NO_{14}$
79
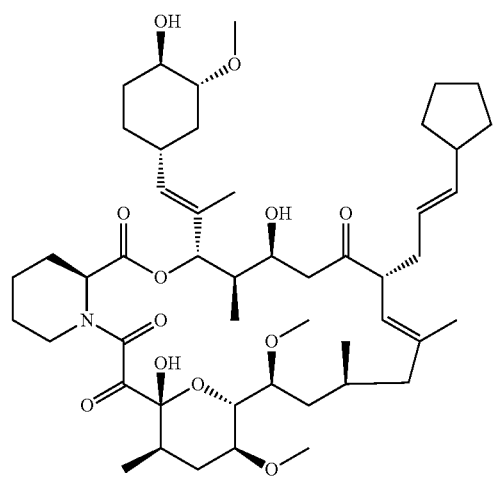 [SMILES: CO[C@H]1C[C@@H](C)C/C(C)=C/[C@@H](C/C=C/C2CCCC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{49}H_{77}NO_{12}$
80
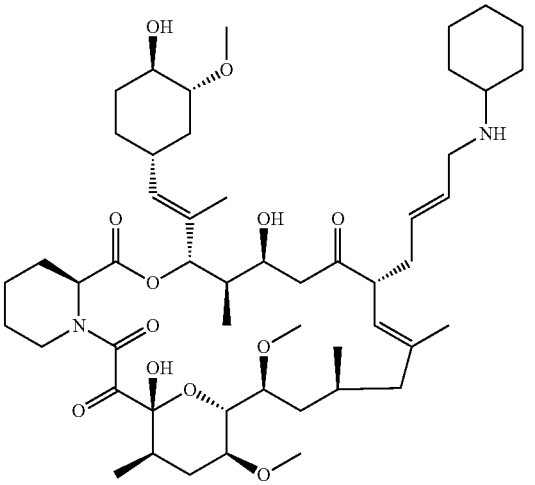 [SMILES: CO[C@H]1C[C@@H](C)C/C(C)=C/[C@@H](C/C=C/CNC2CCCCC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{51}H_{82}N_2O_{12}$ TABLE 1-continued
Antifungal Compounds
81
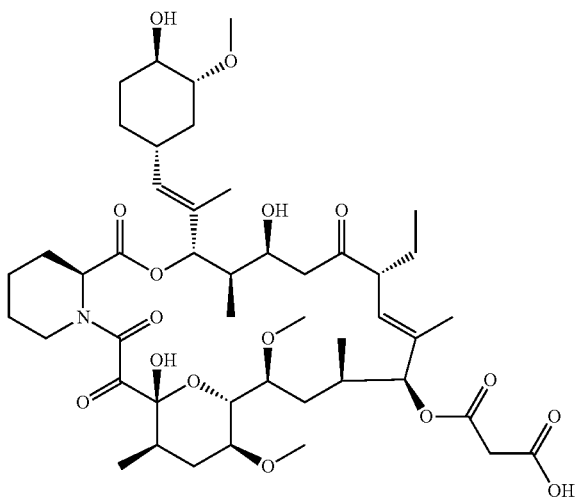 [SMILES: CC[C@@H]1/C=C(\C)[C@@H](OC(=O)CC(=O)O)[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
$C_{46}H_{71}NO_{16}$
82
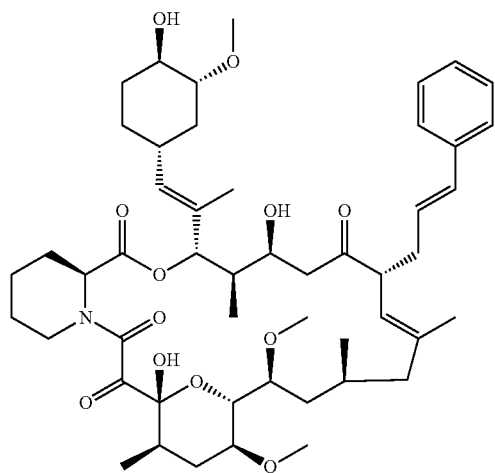 [SMILES: CO[C@H]1C[C@@H](C)C/C(C)=C/[C@@H](C/C=C/c2ccccc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
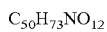
$C_{50}H_{73}NO_{12}$
83
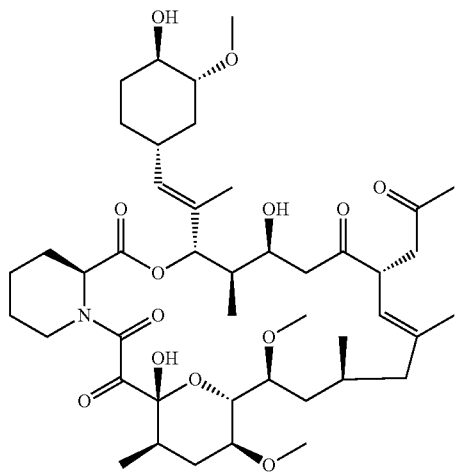 [SMILES: CO[C@H]1C[C@@H](C)C/C(C)=C/[C@@H](CC(C)=O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
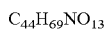
$C_{44}H_{69}NO_{13}$ TABLE 1-continued
Antifungal Compounds
84
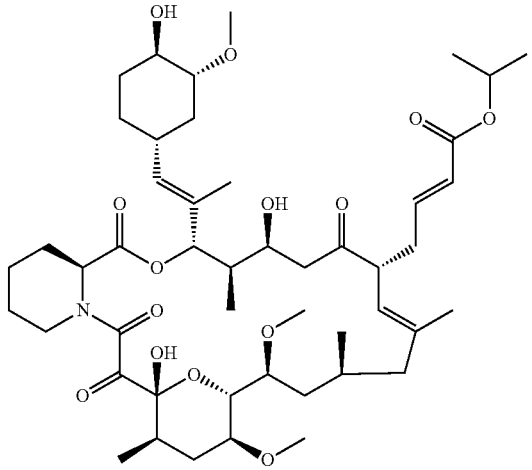 [SMILES: CO[C@H]1C[C@@H](C)C/C(C)=C/[C@@H](C/C=C/C(=O)OC(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{48}H_{75}NO_{14}$
85
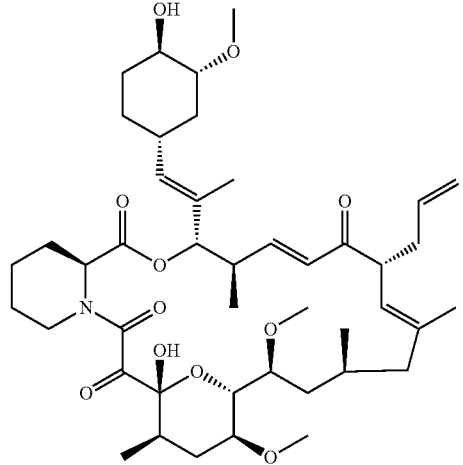 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)/C=C/C1=O)[C@H](C)C[C@@H]2OC]
$C_{44}H_{67}NO_{11}$
86
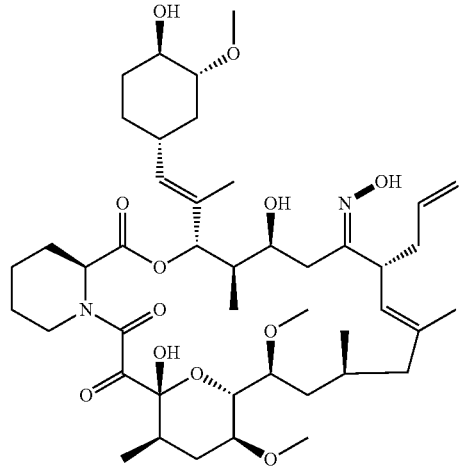
$C_{44}H_{70}N_2O_{12}$ TABLE 1-continued
Antifungal Compounds
87
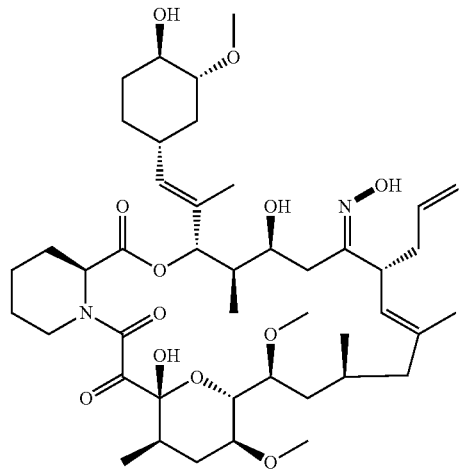
$C_{44}H_{70}N_2O_{12}$
88
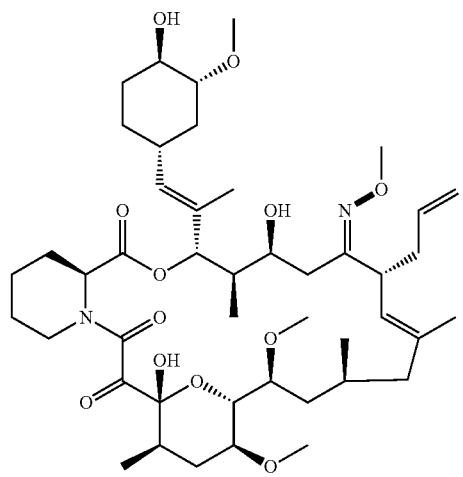
$C_{45}H_{72}N_2O_{12}$
89
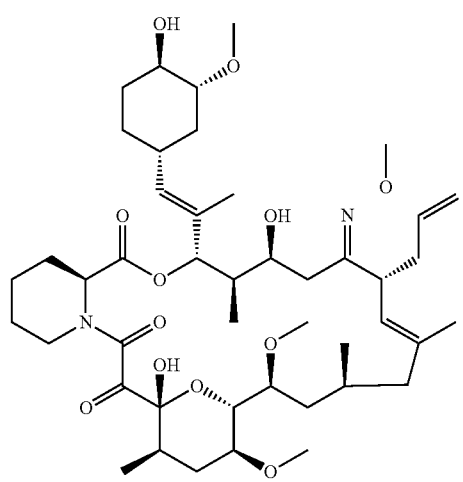
$C_{45}H_{72}N_2O_{12}$ TABLE 1-continued
Antifungal Compounds
90
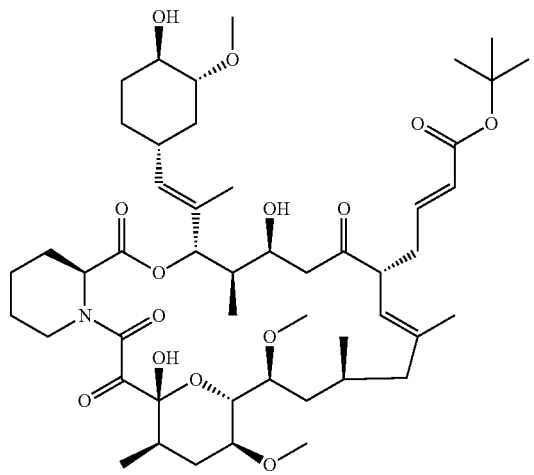 [SMILES: CO[C@H]1C[C@@H](C)C/C(C)=C/[C@@H](C/C=C/C(=O)OC(C)(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{49}H_{77}NO_{14}$
91
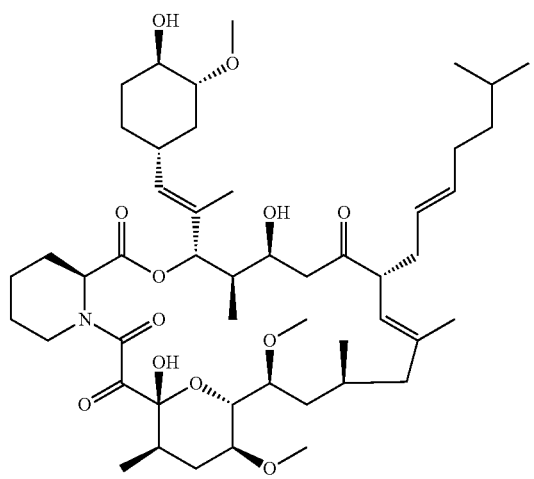 [SMILES: CO[C@H]1C[C@@H](C)C/C(C)=C/[C@@H](C/C=C/CCC(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{49}H_{79}NO_{12}$
92
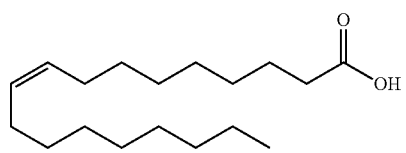 [SMILES: CCCCCCCC/C=C\CCCCCCCC(=O)O]
$C_{18}H_{34}O_2$
93
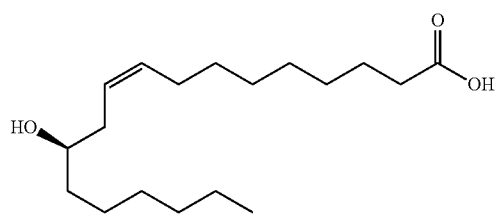 [SMILES: CCCCCC[C@@H](O)C/C=C\CCCCCCCC(=O)O]
$C_{18}H_{34}O_3$ TABLE 1-continued Antifungal Compounds

94

$C_{18}H_{36}O_3$

95

$C_8H_{16}O_3$

96

$C_{47}H_{75}NO_{14}$

97

$C_{54}H_{81}NO_{15}S$

TABLE 1-continued
Antifungal Compounds
98
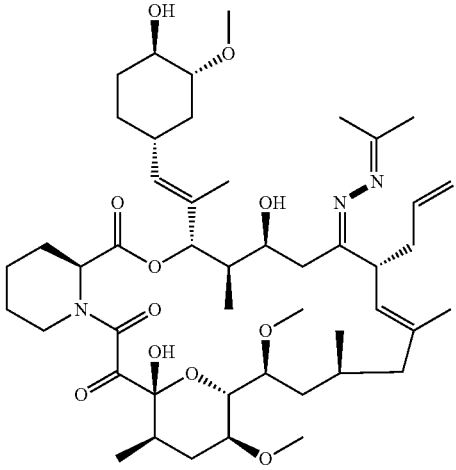
$C_{47}H_{75}N_3O_{11}$
99
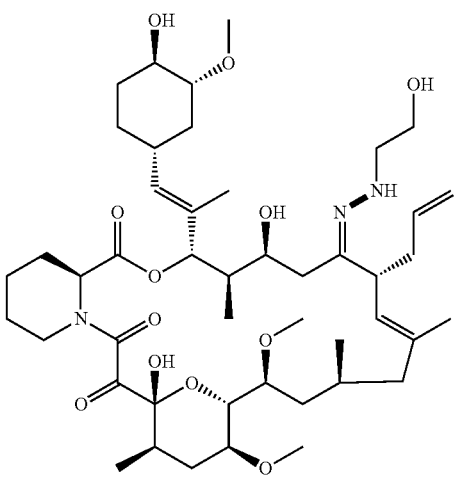
$C_{46}H_{75}N_3O_{12}$
100
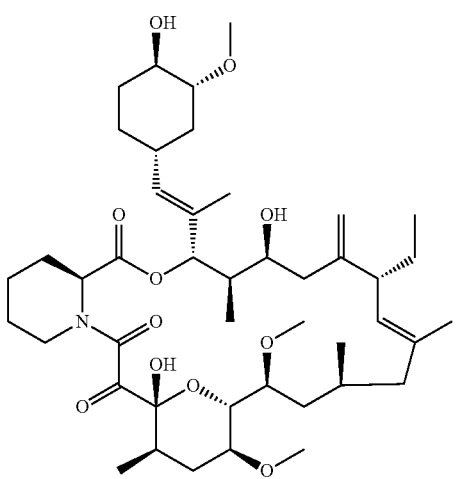 [SMILES: C=C1C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C/C(C)=C/[C@H]1CC)[C@@H](OC)C[C@H]2C]
$C_{44}H_{71}NO_{11}$ TABLE 1-continued
Antifungal Compounds
101
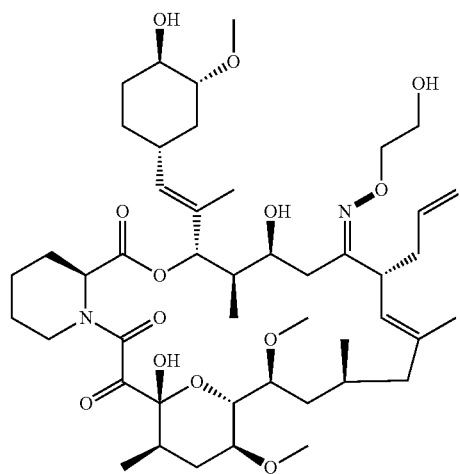
$C_{46}H_{74}N_2O_{13}$
102
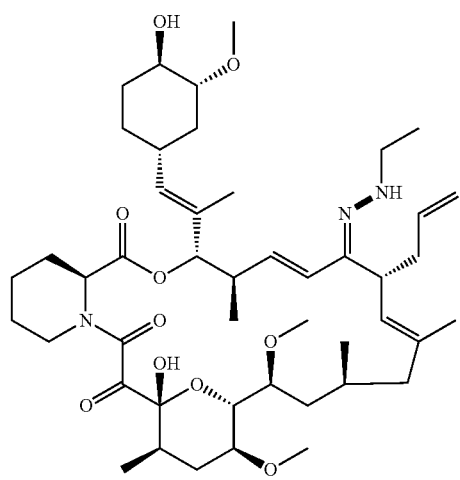
$C_{46}H_{73}N_3O_{10}$
103
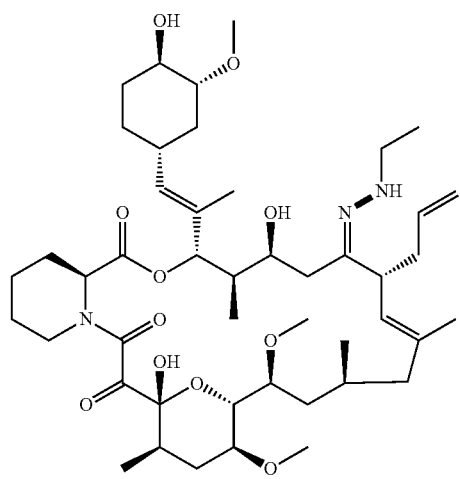
$C_{46}H_{75}N_3O_{11}$ TABLE 1-continued
Antifungal Compounds
104
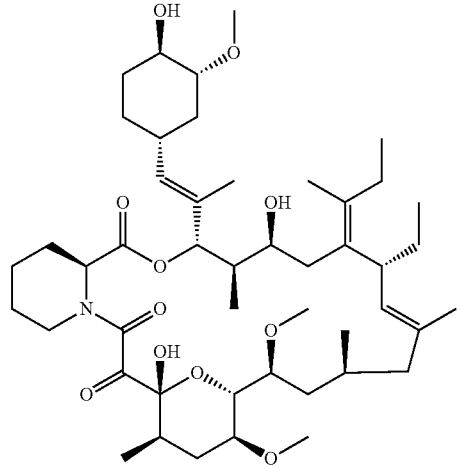 [SMILES: CC/C(C)=C1/C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C/C(C)=C/[C@H]1CC)[C@@H](OC)C[C@H]2C]
$C_{47}H_{77}NO_{11}$
105
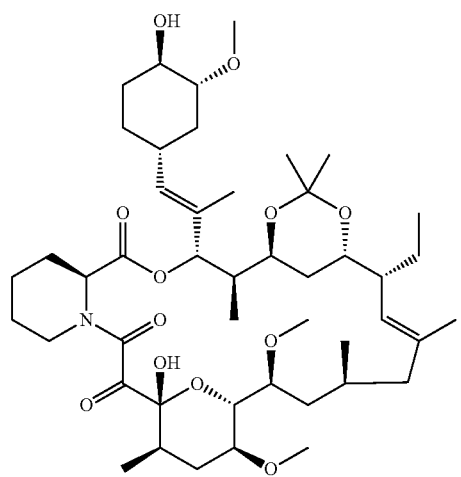 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H]3C[C@@H]1OC(C)(C)O3)[C@H](C)C[C@@H]2OC]
$C_{46}H_{75}NO_{12}$
106
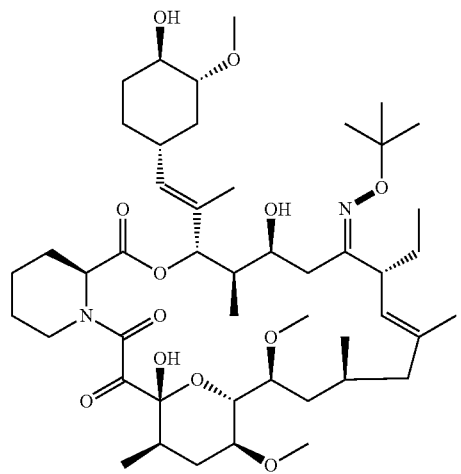
$C_{47}H_{78}N_{2}O_{12}$ TABLE 1-continued
Antifungal Compounds
107
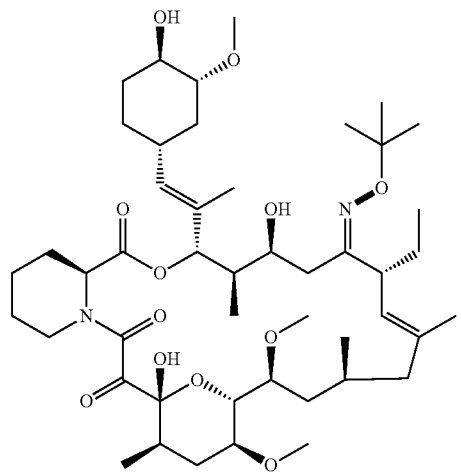
$C_{47}H_{78}N_2O_{12}$
108
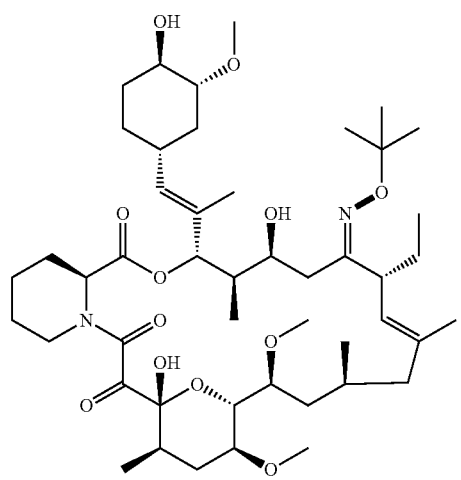
$C_{47}H_{78}N_2O_{12}$
109
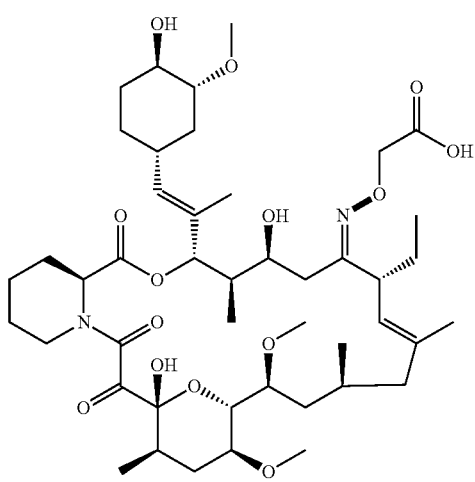
$C_{45}H_{72}N_2O_{14}$ TABLE 1-continued
Antifungal Compounds
110
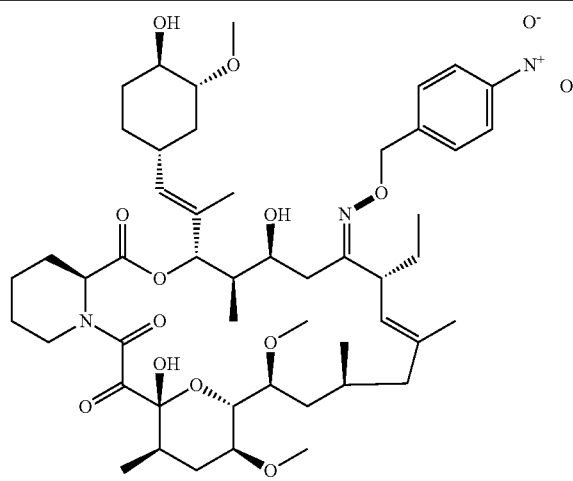
$C_{50}H_{75}N_3O_{14}$
111
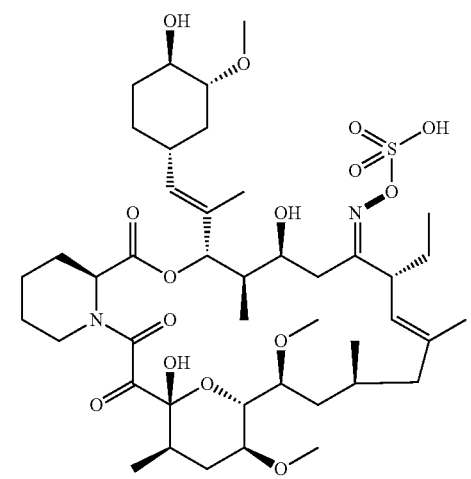
$C_{43}H_{70}N_2O_{15}S$
112
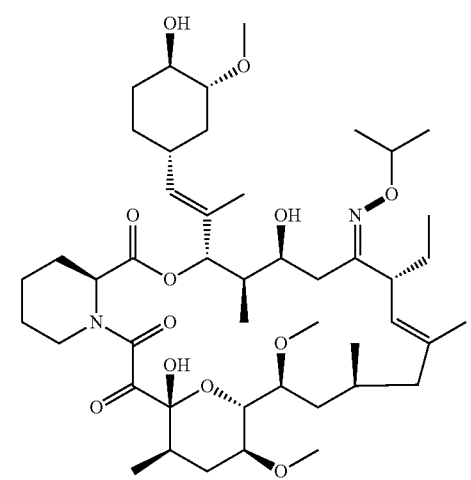
$C_{46}H_{76}N_2O_{12}$ TABLE 1-continued
Antifungal Compounds
113
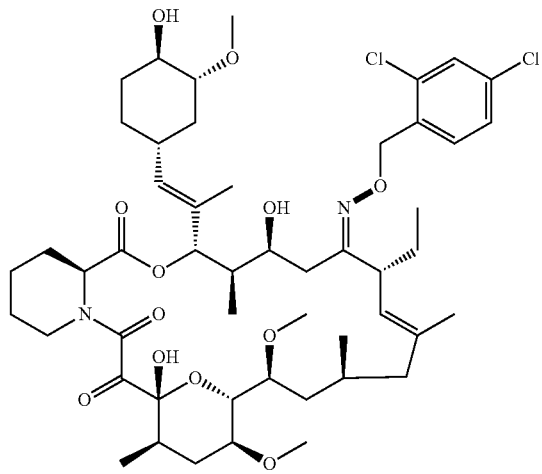
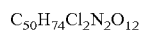
114
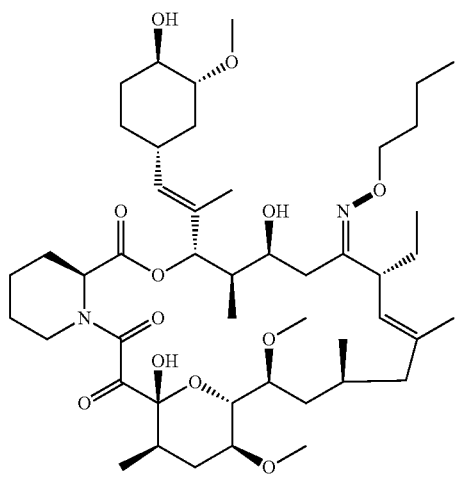
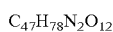
115
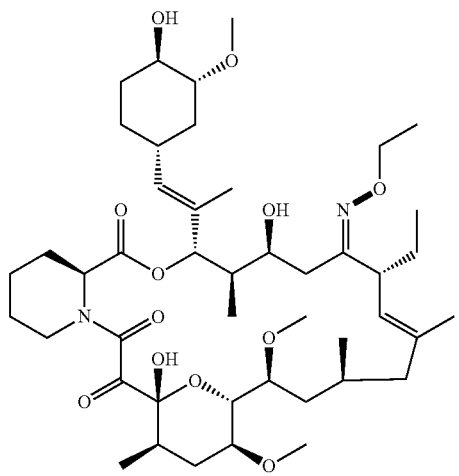

TABLE 1-continued
Antifungal Compounds
116
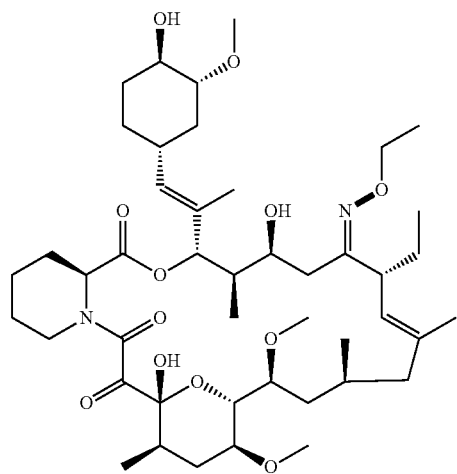
$C_{45}H_{74}N_2O_{12}$
117
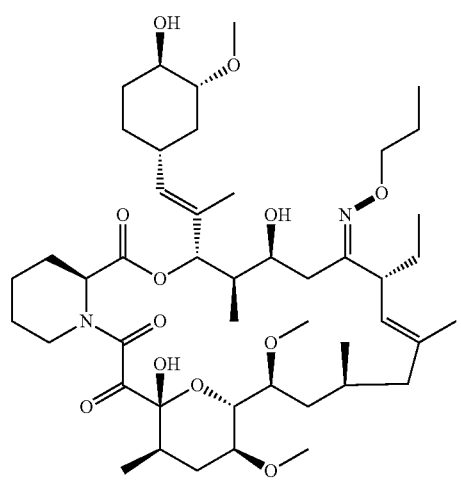
$C_{46}H_{76}N_2O_{12}$
118
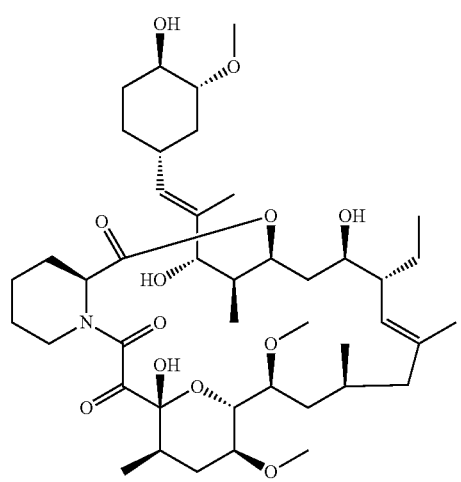 [SMILES: CC[C@@H]1/C=C(\C)C[C@H](C)C[C@H](OC)[C@H]2O[C@@](O)(C(=O)C(=O)N3CCCC[C@H]3C(=O)O[C@H]([C@@H](C)[C@H](O)/C(C)=C/[C@@H]3CC[C@@H](O)[C@H](OC)C3)C[C@H]1O)[C@H](C)C[C@@H]2OC]
$C_{43}H_{71}NO_{12}$ TABLE 1-continued
Antifungal Compounds
119
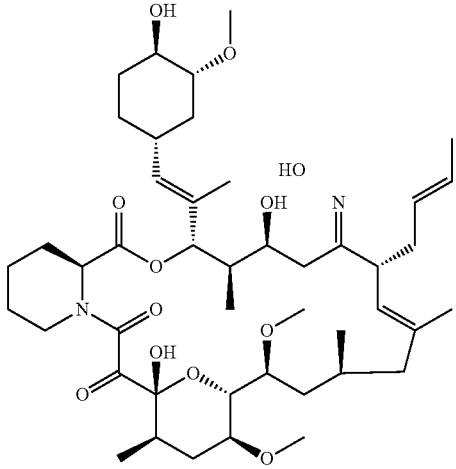
$C_{45}H_{72}N_2O_{12}$
120
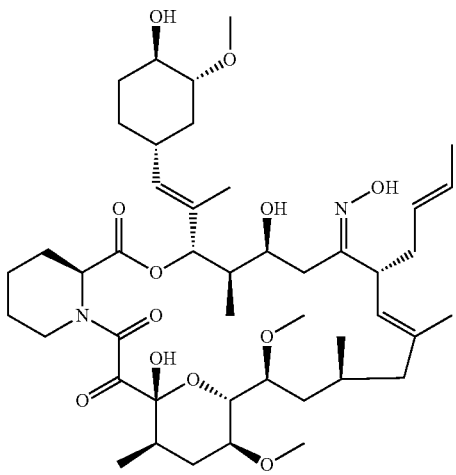 [SMILES: C/C=C/C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)C/C1=N/O)[C@H](C)C[C@@H]2OC]
$C_{45}H_{72}N_2O_{12}$
121
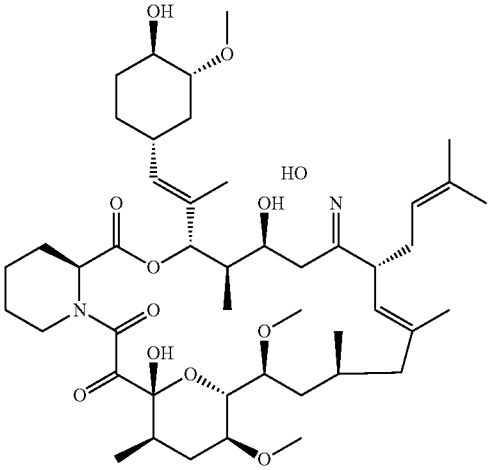
$C_{46}H_{74}N_2O_{12}$ TABLE 1-continued
Antifungal Compounds
122
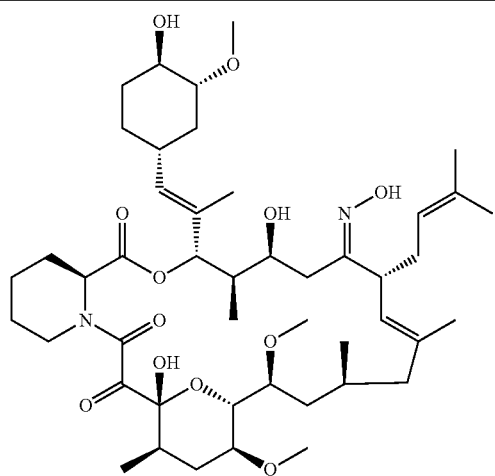
$C_{46}H_{74}N_2O_{12}$
123
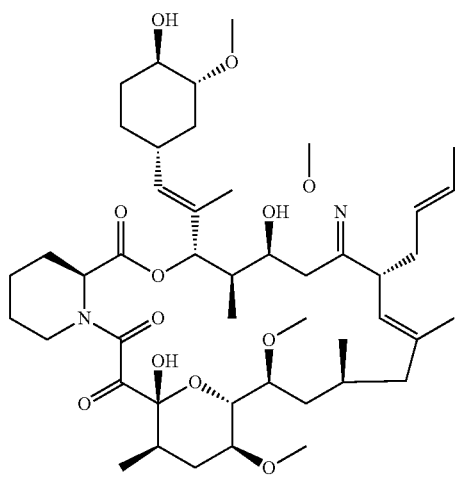
$C_{46}H_{74}N_2O_{12}$
124
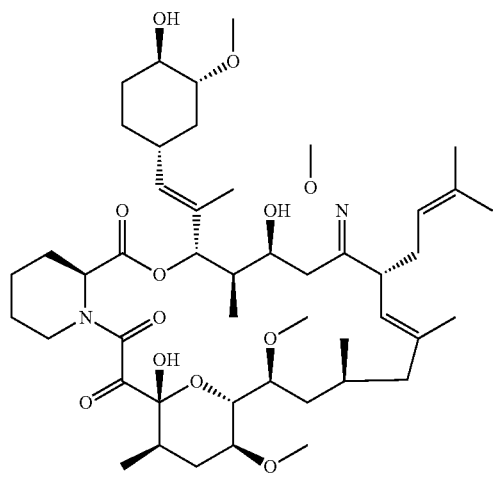
$C_{47}H_{76}N_2O_{12}$ TABLE 1-continued
Antifungal Compounds
125
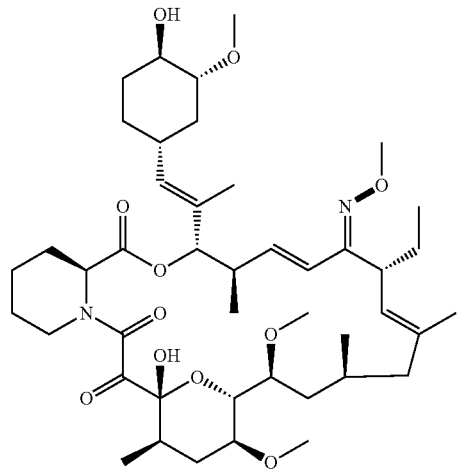
C$_{44}$H$_{70}$N$_2$O$_{11}$
126
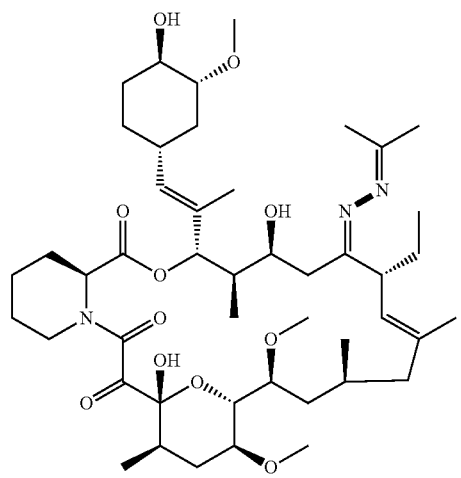
C$_{46}$H$_{75}$N$_3$O$_{11}$
127
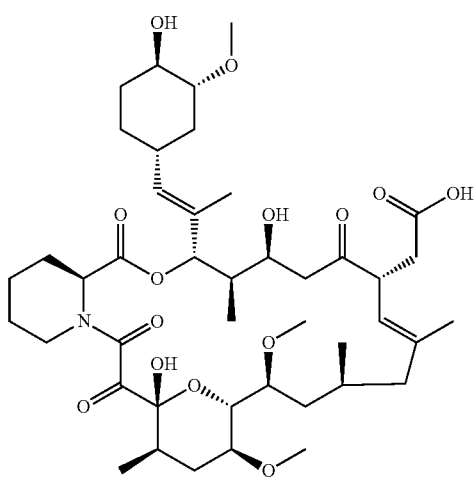 [SMILES: CO[C@H]1C[C@@H](C)C/C(C)=C/[C@@H](CC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
C$_{43}$H$_{67}$NO$_{14}$ TABLE 1-continued
Antifungal Compounds
128
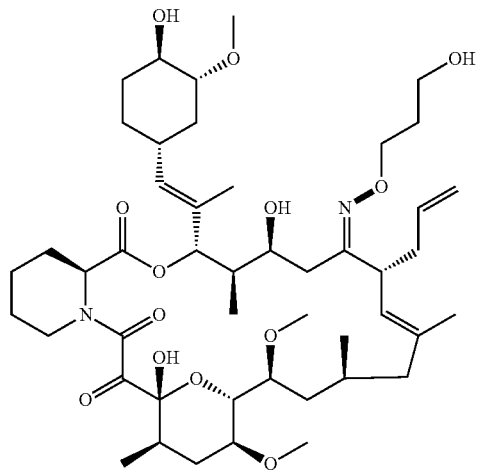
$C_{47}H_{76}N_2O_{13}$
129
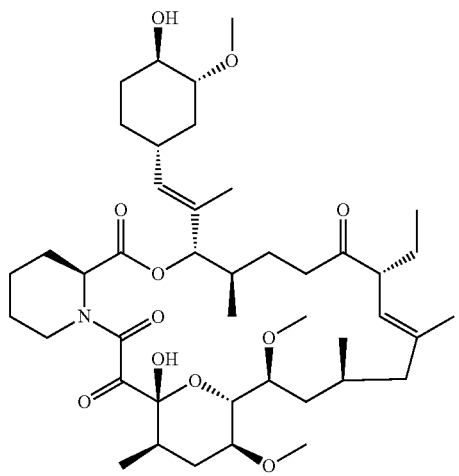 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)CCC1=O)[C@H](C)C[C@@H]2OC]
$C_{43}H_{69}NO_{11}$
130
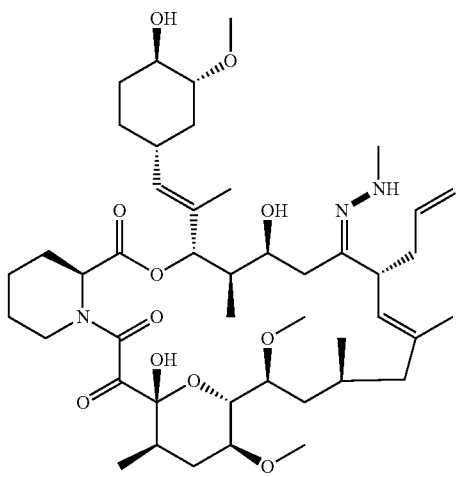
$C_{45}H_{73}N_3O_{11}$ TABLE 1-continued
Antifungal Compounds
131
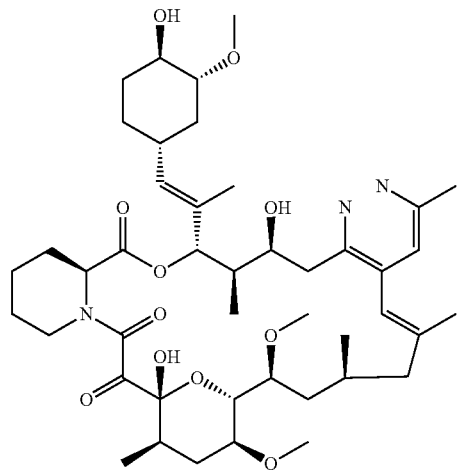 [SMILES: CO[C@H]1C[C@@H](C)C/C(C)=C/C(/C=C(/C)N)=C(/N)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{44}H_{67}N_3O_{11}$
132
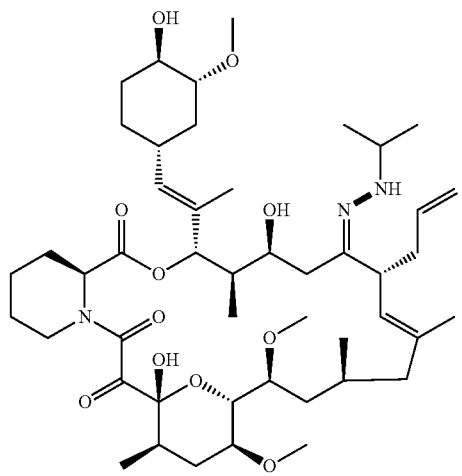
$C_{47}H_{77}N_3O_{11}$
133
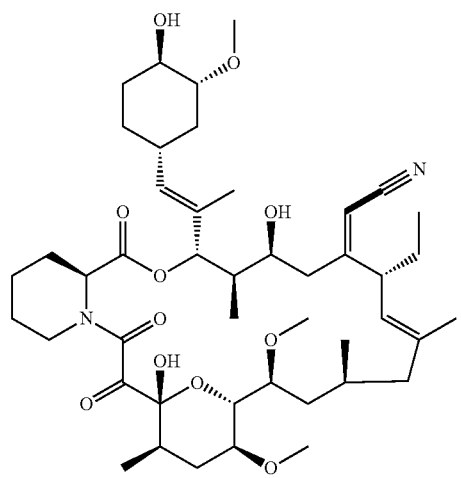
$C_{45}H_{70}N_2O_{11}$ TABLE 1-continued
Antifungal Compounds
134 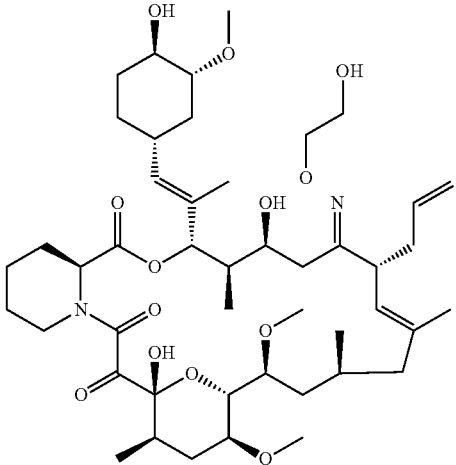
$C_{46}H_{74}N_2O_{13}$
135 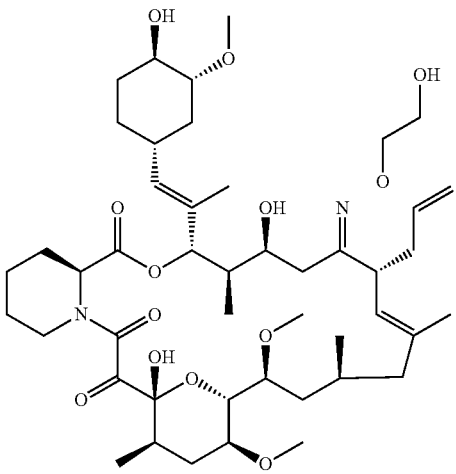
$C_{46}H_{74}N_2O_{13}$
136 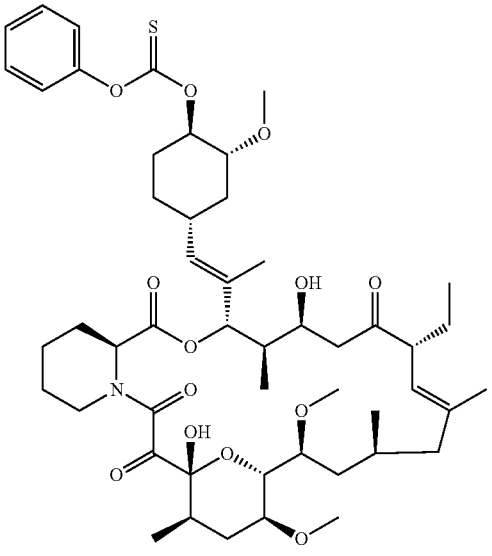 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=S)Oc4ccccc4)[C@H](OC)C3)[C@H](C)[C@@H](O)CC1=O)[C@H](C)C[C@@H]2OC]
$C_{50}H_{73}NO_{13}S$ 111 112
TABLE 1-continued
Antifungal Compounds
137
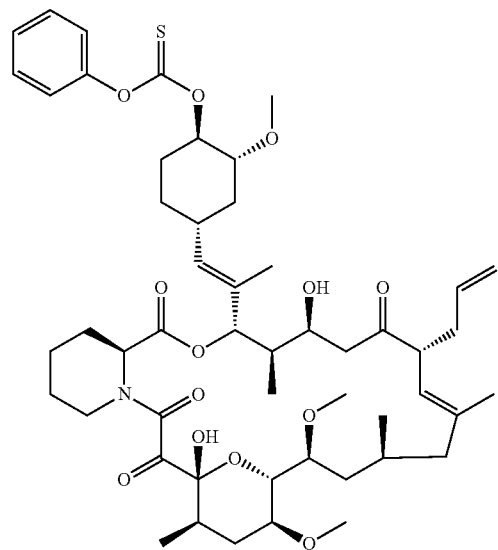 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=S)Oc4ccccc4)[C@H](OC)C3)[C@H](C)[C@@H](O)CC1=O)[C@H](C)C[C@@H]2OC]
$C_{51}H_{73}NO_{13}S$
138
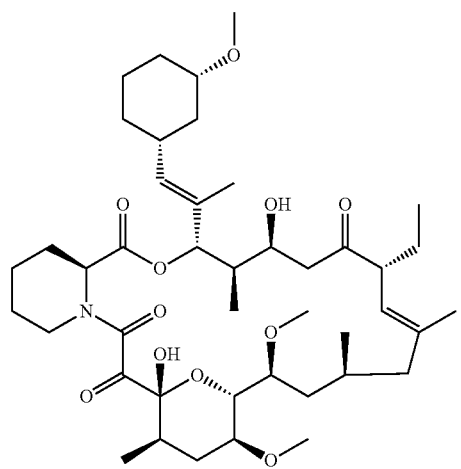 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC[C@H](OC)C3)[C@H](C)[C@@H](O)CC1=O)[C@H](C)C[C@@H]2OC]
$C_{43}H_{69}NO_{11}$ TABLE 1-continued
Antifungal Compounds
139
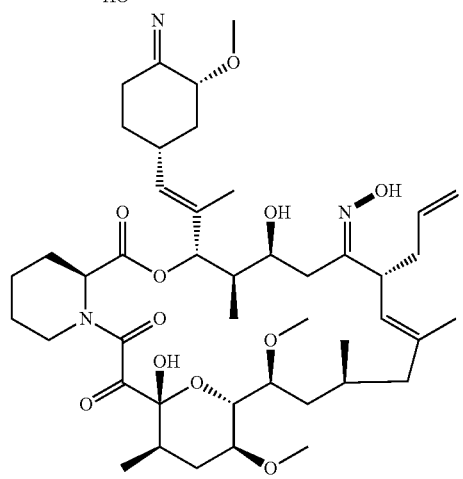
C₄₄H₆₉N₃O₁₂
140
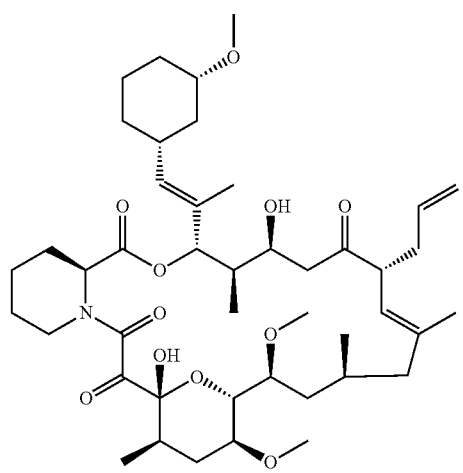 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC[C@H](OC)C3)[C@H](C)[C@@H](O)CC1=O)[C@H](C)C[C@@H]2OC]
C₄₄H₆₉NO₁₁
141
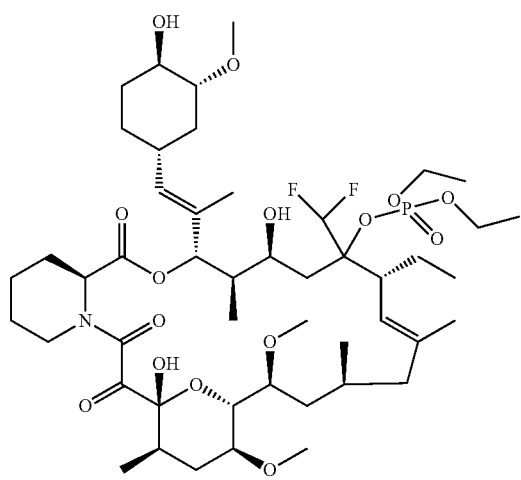
C₄₈H₈₀F₂NO₁₅P TABLE 1-continued
Antifungal Compounds
142
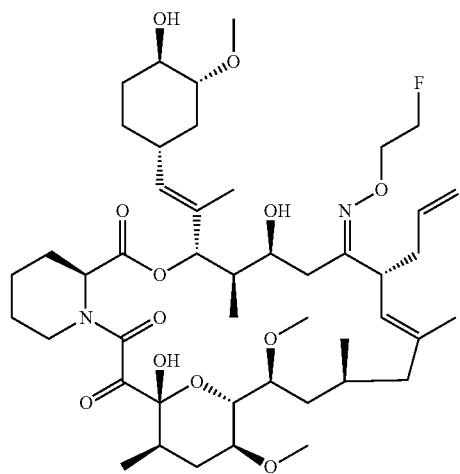 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)C/C1=N/OCCF)[C@H](C)C[C@@H]2OC]
$C_{46}H_{73}FN_2O_{12}$
143
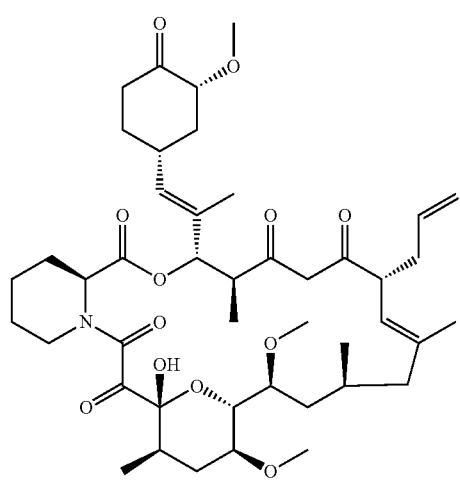 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC(=O)[C@H](OC)C3)[C@H](C)C(=O)CC1=O)[C@H](C)C[C@@H]2OC]
$C_{44}H_{65}NO_{12}$
144
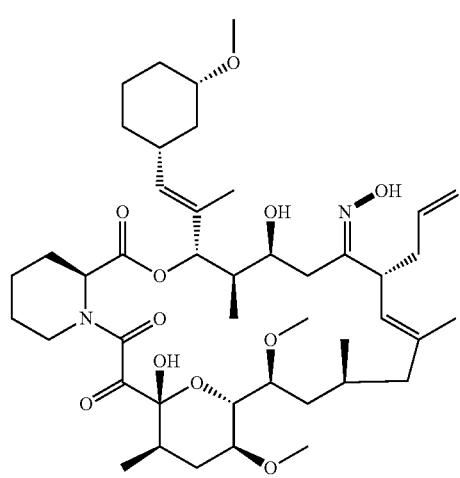
$C_{44}H_{70}N_2O_{11}$ TABLE 1-continued
Antifungal Compounds
145
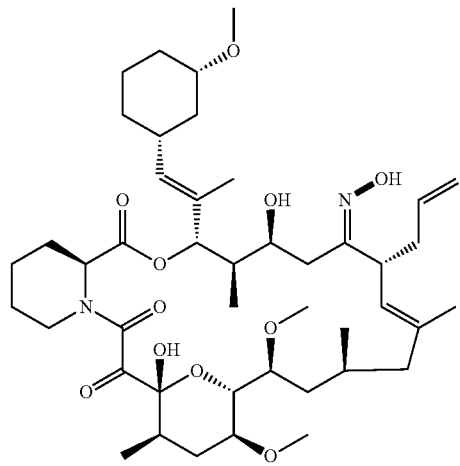
$C_{44}H_{70}N_2O_{11}$
146
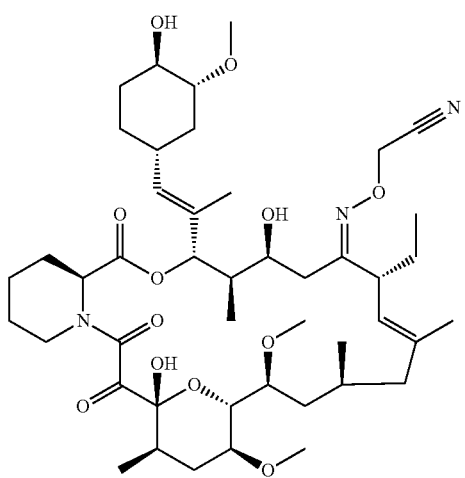 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)C/C1=N/OCC#N)[C@H](C)C[C@@H]2OC]
$C_{45}H_{71}N_3O_{12}$
147
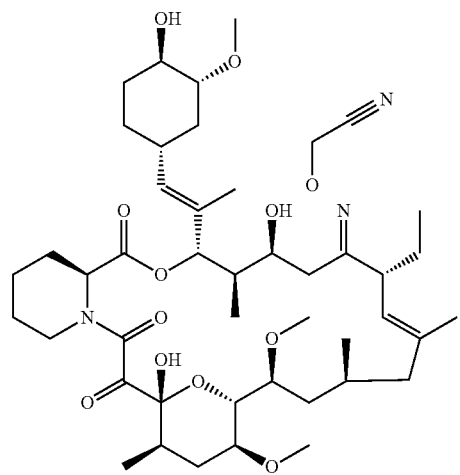
$C_{45}H_{71}N_3O_{12}$ TABLE 1-continued
Antifungal Compounds
148
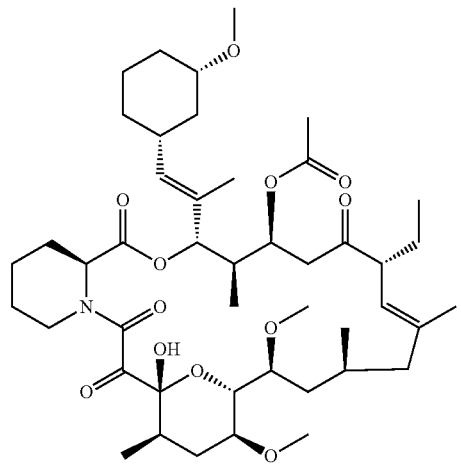 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC[C@H](OC)C3)[C@H](C)[C@@H](OC(C)=O)CC1=O)[C@H](C)C[C@@H]2OC]
$C_{45}H_{71}NO_{12}$
149
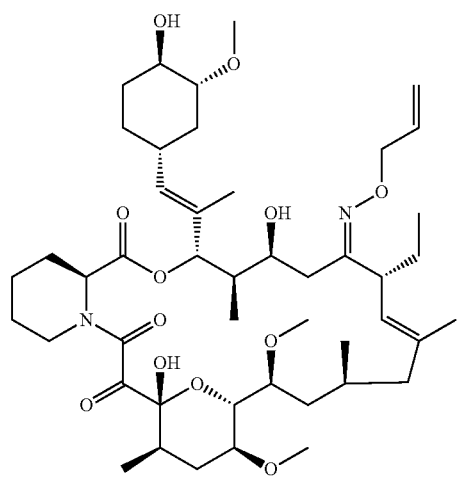 [SMILES: C=CCO/N=C1/C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C/C(C)=C/[C@H]1CC)[C@@H](OC)C[C@H]2C]
$C_{46}H_{74}N_2O_{12}$
150
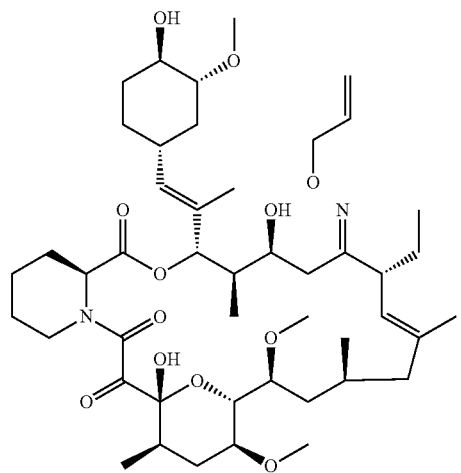
$C_{46}H_{74}N_2O_{12}$ TABLE 1-continued
Antifungal Compounds
151
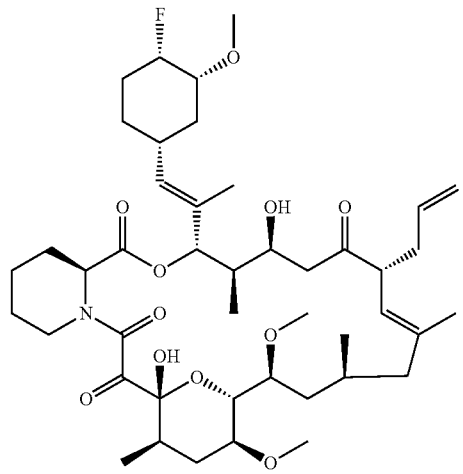
$C_{44}H_{68}FNO_{11}$
152
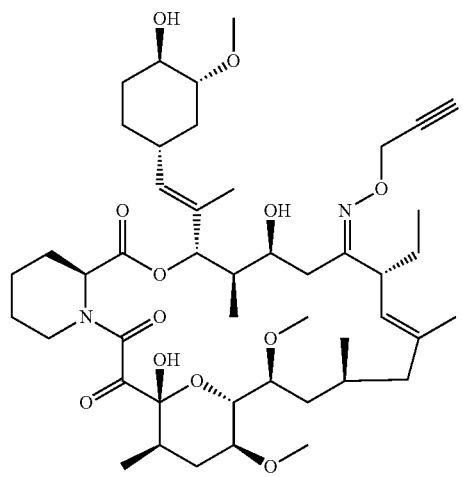 [SMILES: C#CCO/N=C1/C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C/C(C)=C/[C@H]1CC)[C@@H](OC)C[C@H]2C]
$C_{46}H_{72}N_2O_{12}$
153
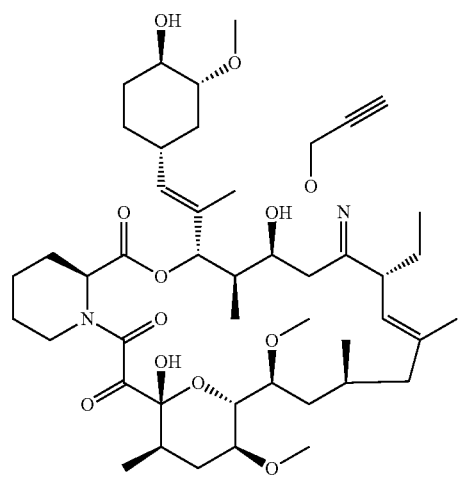
$C_{46}H_{72}N_2O_{12}$ TABLE 1-continued
Antifungal Compounds
154 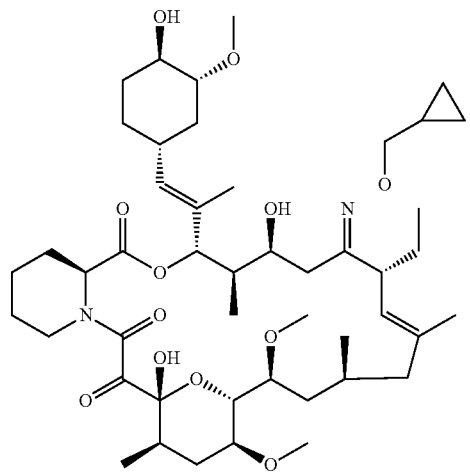
C$_{47}$H$_{76}$N$_2$O$_{12}$
155 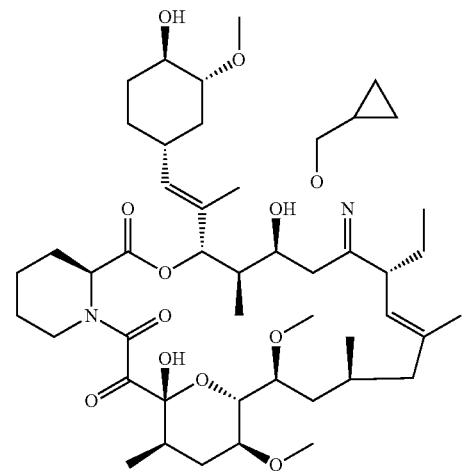
C$_{47}$H$_{76}$N$_2$O$_{12}$
156 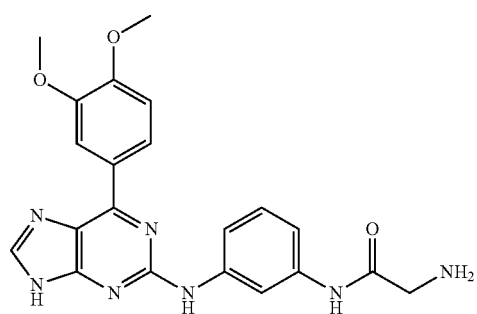 [SMILES: COc1ccc(-c2nc(Nc3cccc(NC(=O)CN)c3)nc3[nH]cnc23)cc1OC]
C$_{21}$H$_{21}$N$_7$O$_3$ TABLE 1-continued
Antifungal Compounds
157
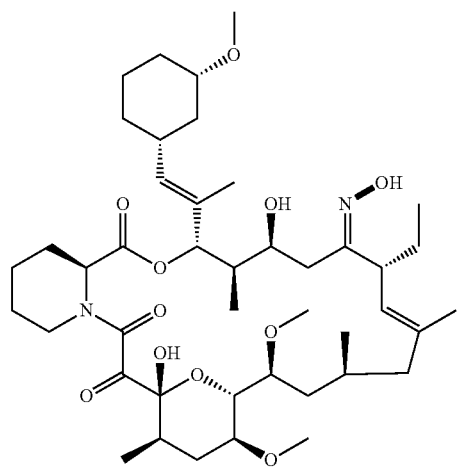
$C_{43}H_{70}N_2O_{11}$
158
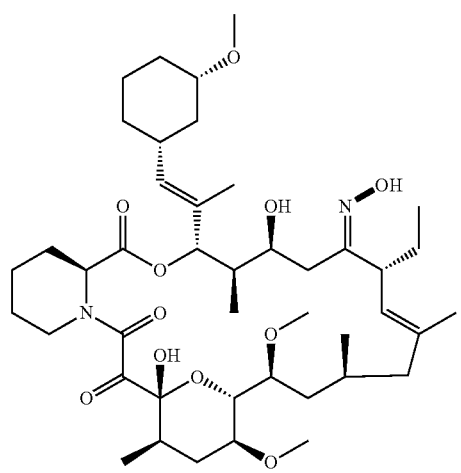
$C_{43}H_{70}N_2O_{11}$
159
160
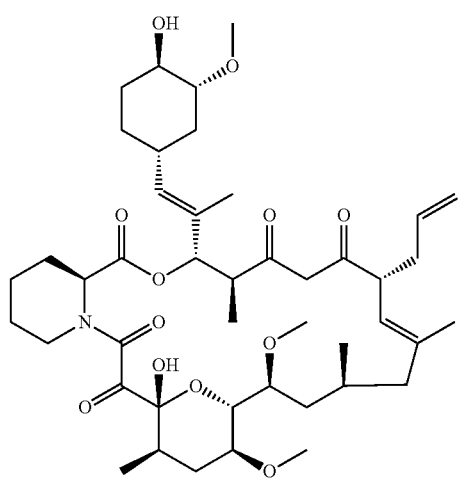 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)C(=O)CC1=O)[C@H](C)C[C@@H]2OC]
$C_{44}H_{67}NO_{12}$ TABLE 1-continued
Antifungal Compounds
161
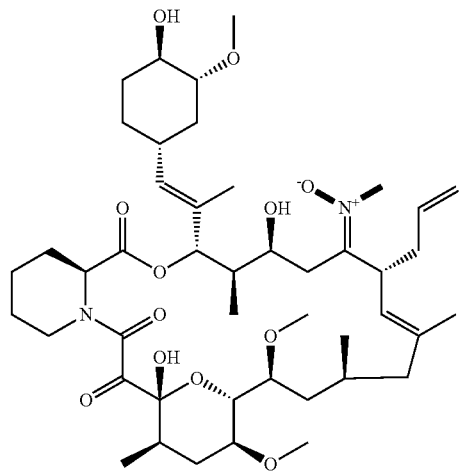
$C_{45}H_{72}N_2O_{12}$
162
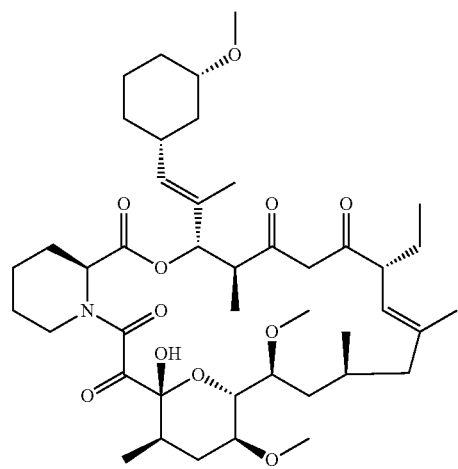 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC[C@H](OC)C3)[C@H](C)C(=O)CC1=O)[C@H](C)C[C@@H]2OC]
$C_{43}H_{67}NO_{11}$
163
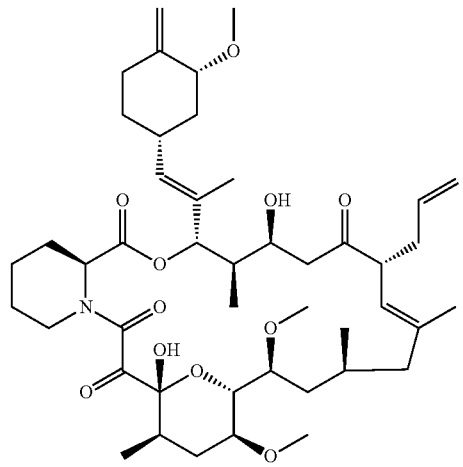 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC(=C)[C@H](OC)C3)[C@H](C)[C@@H](O)CC1=O)[C@H](C)C[C@@H]2OC]
$C_{45}H_{69}NO_{11}$

TABLE 1-continued
Antifungal Compounds
164
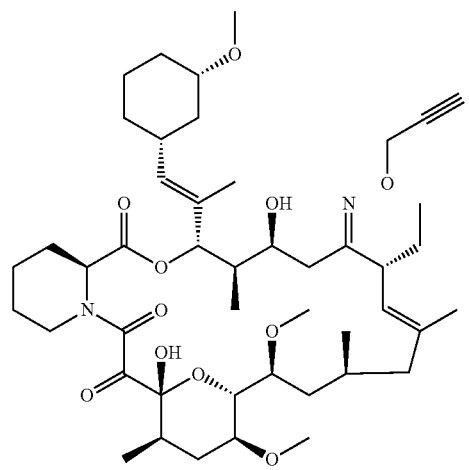
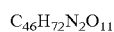
165
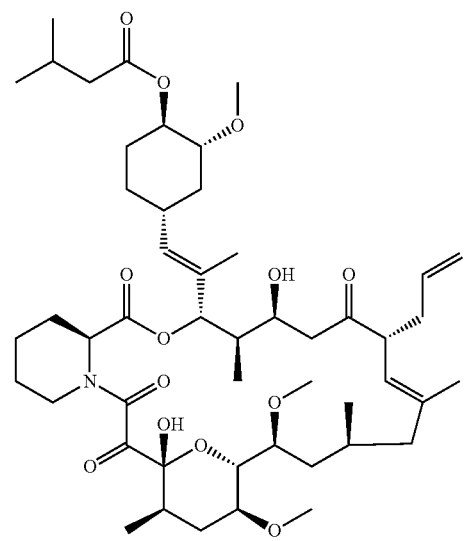 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)CC(C)C)[C@H](OC)C3)[C@H](C)[C@@H](O)CC1=O)[C@H](C)C[C@@H]2OC]

TABLE 1-continued
Antifungal Compounds
166
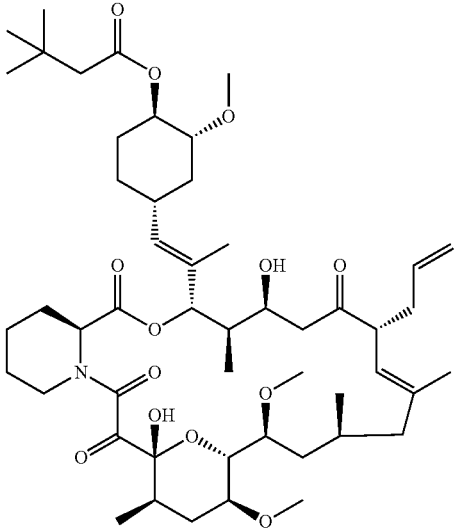 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)CC(C)(C)C)[C@H](OC)C3)[C@H](C)[C@@H](O)CC1=O)[C@H](C)C[C@@H]2OC]
C₅₀H₇₉NO₁₃
167
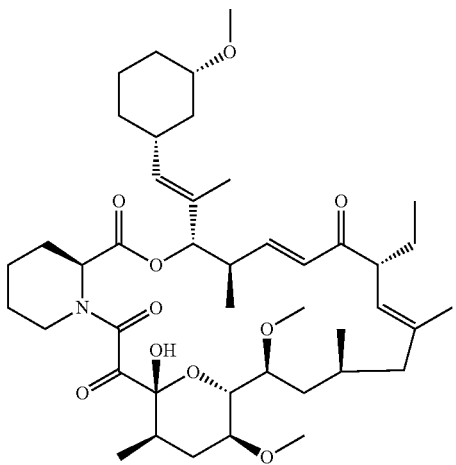 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CCC[C@H](OC)C3)[C@H](C)/C=C/C1=O)[C@H](C)C[C@@H]2OC]
C₄₃H₆₇NO₁₀
168
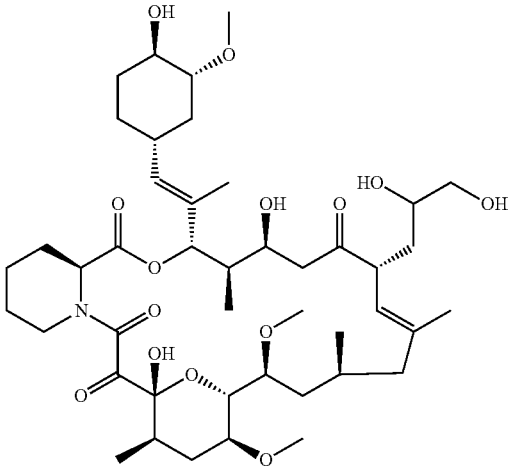 [SMILES: CO[C@H]1C[C@@H](C)C/C(C)=C/[C@@H](CC(O)CO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
C₄₄H₇₁NO₁₄

TABLE 1-continued
Antifungal Compounds
169
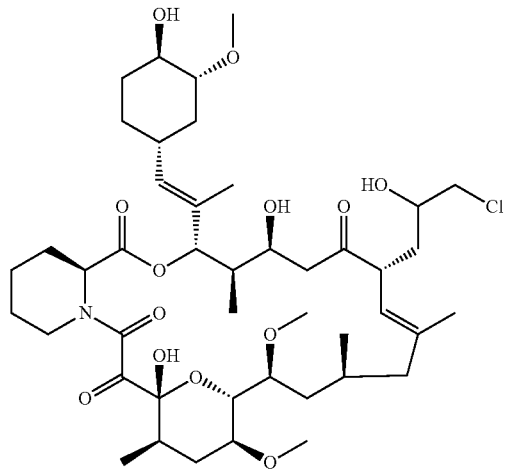 [SMILES: CO[C@H]1C[C@@H](C)C/C(C)=C/[C@@H](CC(O)CCl)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{44}H_{70}ClNO_{13}$
170
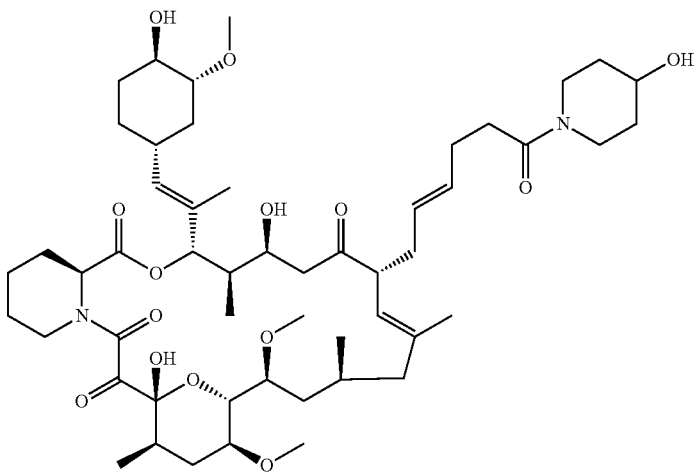 [SMILES: CO[C@H]1C[C@@H](C)C/C(C)=C/[C@@H](C/C=C/CCC(=O)N2CCC(O)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{52}H_{82}N_2O_{14}$
171
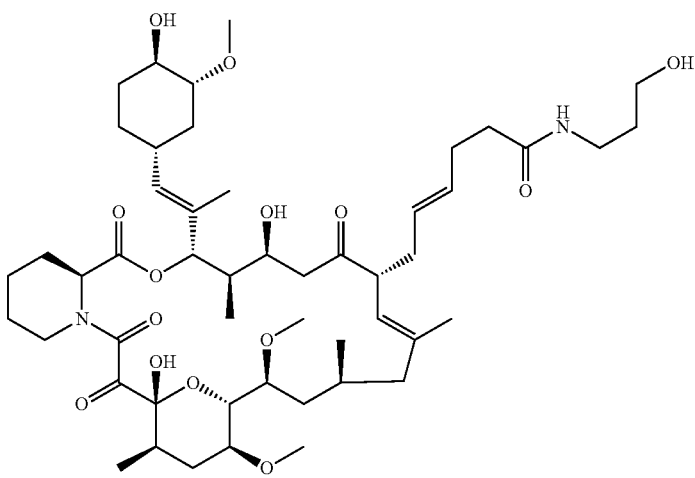 [SMILES: CO[C@H]1C[C@@H](C)C/C(C)=C/[C@@H](C/C=C/CCC(=O)NCCCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{50}H_{80}N_2O_{14}$ TABLE 1-continued
Antifungal Compounds
172
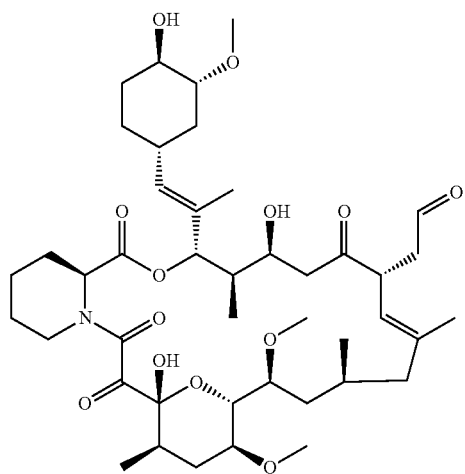 [SMILES: CO[C@H]1C[C@@H](C)C/C(C)=C/[C@@H](CC=O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{43}H_{67}NO_{13}$
173
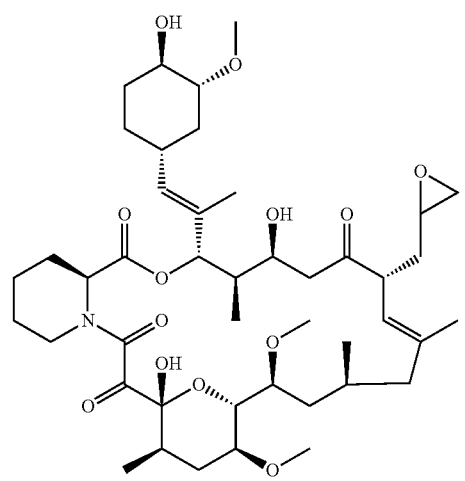 [SMILES: CO[C@H]1C[C@@H](C)C/C(C)=C/[C@@H](CC2CO2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{44}H_{69}NO_{13}$
174
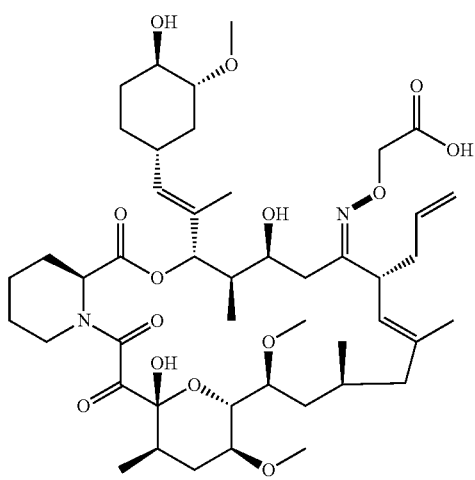
$C_{46}H_{72}N_2O_{14}$ TABLE 1-continued
Antifungal Compounds
175
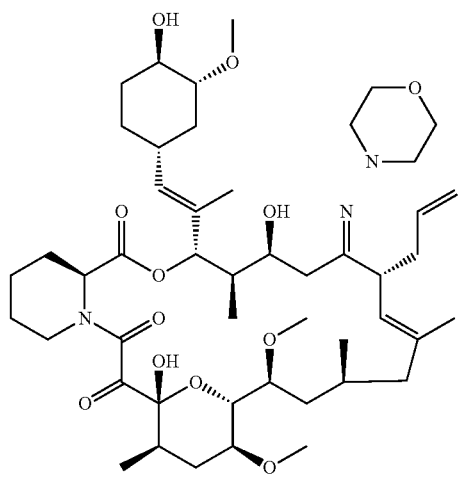
$C_{48}H_{77}N_3O_{12}$
176
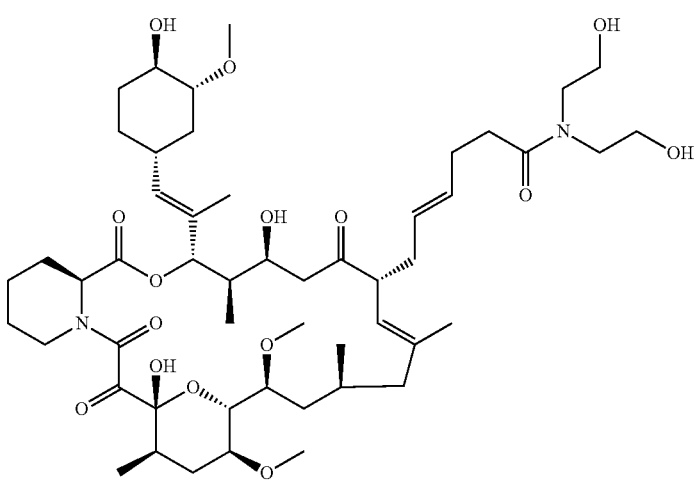 [SMILES: CO[C@H]1C[C@@H](C)C/C(C)=C/[C@@H](C/C=C/CCC(=O)N(CCO)CCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{51}H_{82}N_2O_{15}$
177
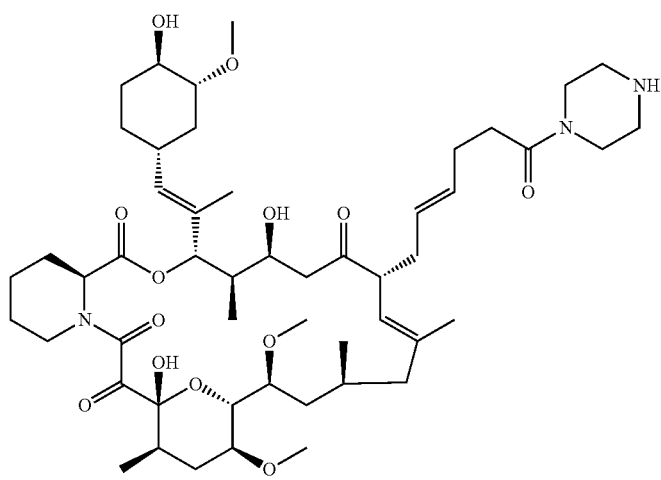 [SMILES: CO[C@H]1C[C@@H](C)C/C(C)=C/[C@@H](C/C=C/CCC(=O)N2CCNCC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{51}H_{81}N_3O_{13}$ TABLE 1-continued
Antifungal Compounds
178 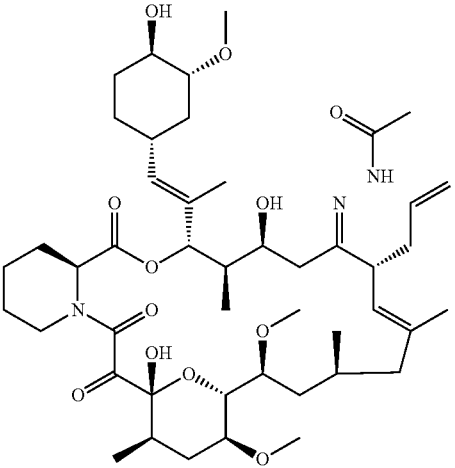
$C_{46}H_{73}N_3O_{12}$
179 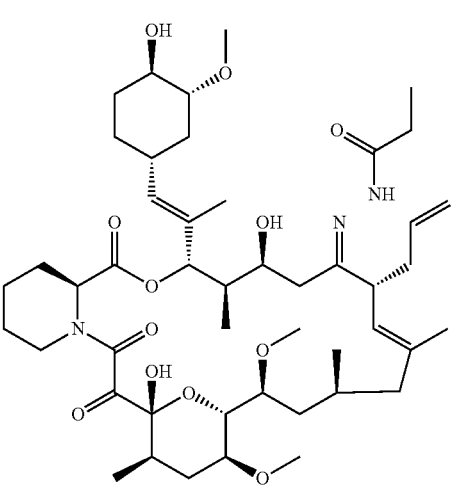
$C_{47}H_{75}N_3O_{12}$
180 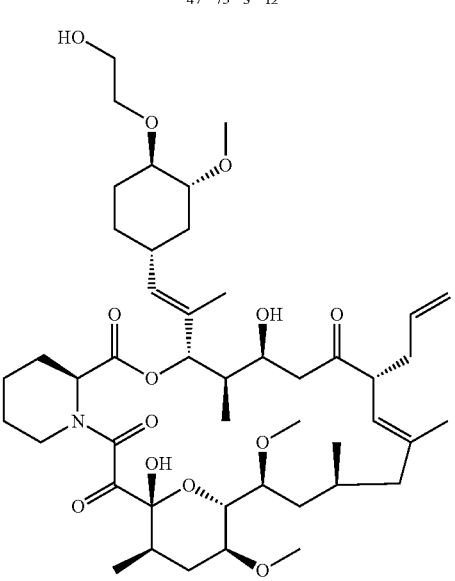
$C_{46}H_{73}NO_{13}$ TABLE 1-continued
Antifungal Compounds
181
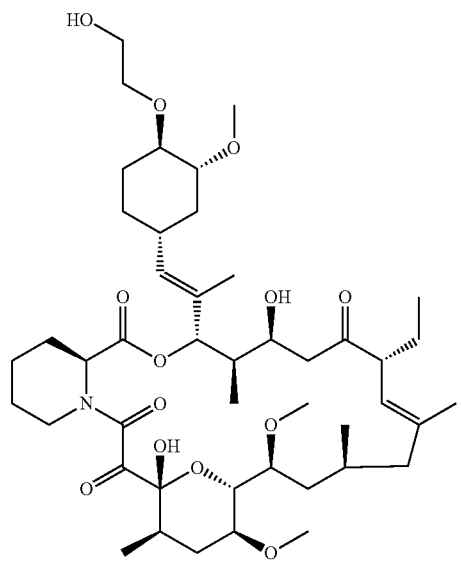 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](OCCO)[C@H](OC)C3)[C@H](C)[C@@H](O)CC1=O)[C@H](C)C[C@@H]2OC]
$C_{45}H_{73}NO_{13}$
182
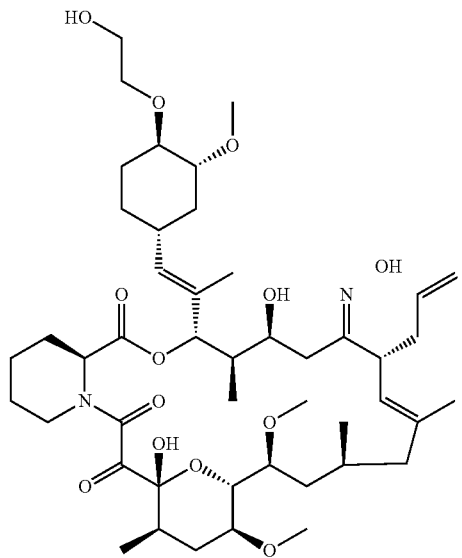
$C_{46}H_{74}N_2O_{13}$ TABLE 1-continued
Antifungal Compounds
183 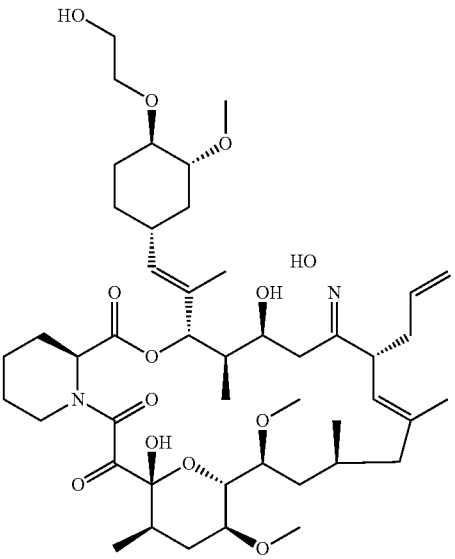
$C_{46}H_{74}N_2O_{13}$
184 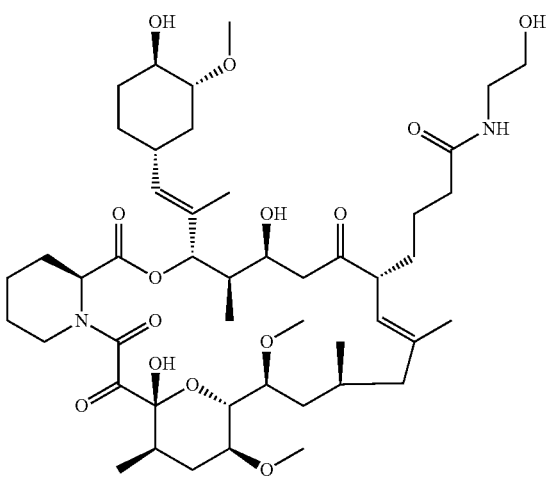 [SMILES: CO[C@H]1C[C@@H](C)C/C(C)=C/[C@@H](CCCC(=O)NCCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{47}H_{76}N_2O_{14}$
185 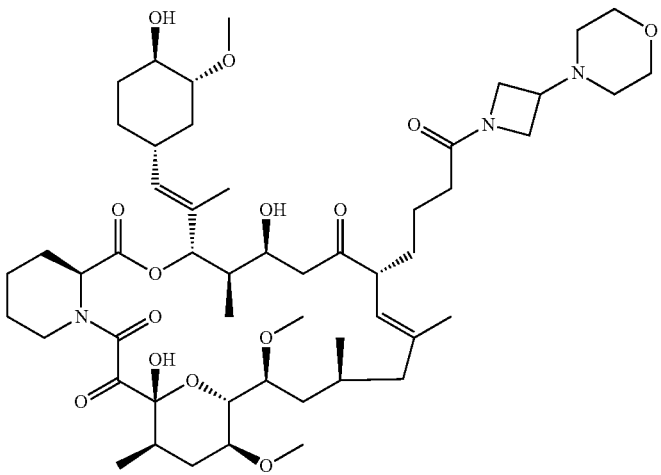 [SMILES: CO[C@H]1C[C@@H](C)C/C(C)=C/[C@@H](CCCC(=O)N2CC(N3CCOCC3)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{52}H_{83}N_3O_{14}$ TABLE 1-continued
Antifungal Compounds
186
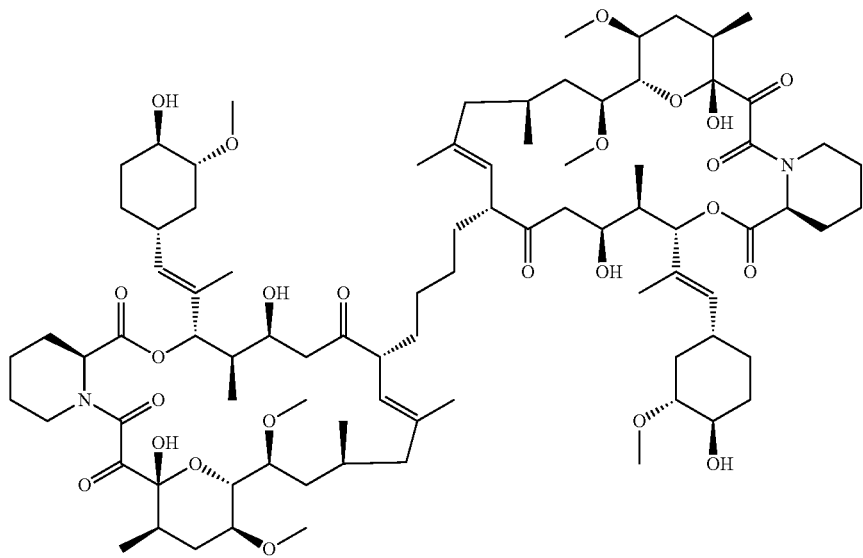 [SMILES: CO[C@H]1C[C@@H](C)C/C(C)=C/[C@@H](CCCC[C@@H]2/C=C(\C)C[C@H](C)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
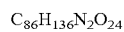
187
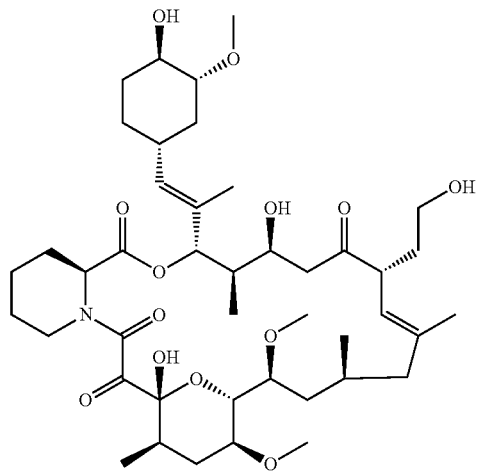 [SMILES: CO[C@H]1C[C@@H](C)C/C(C)=C/[C@@H](CCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
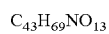

TABLE 1-continued
Antifungal Compounds
188
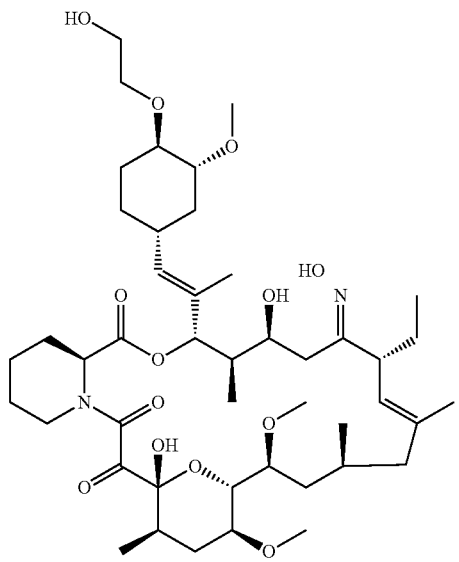
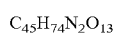
189
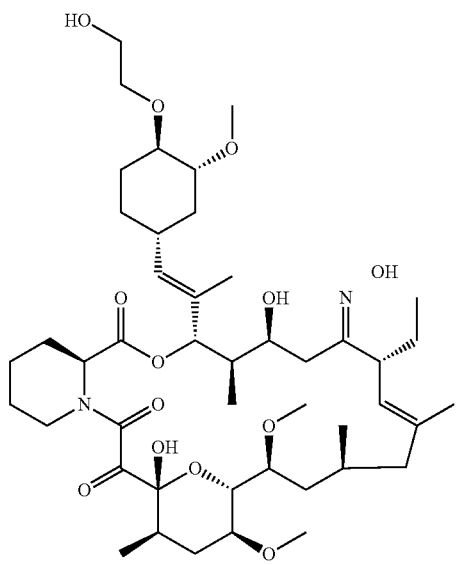
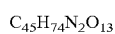

TABLE 1-continued
Antifungal Compounds
190
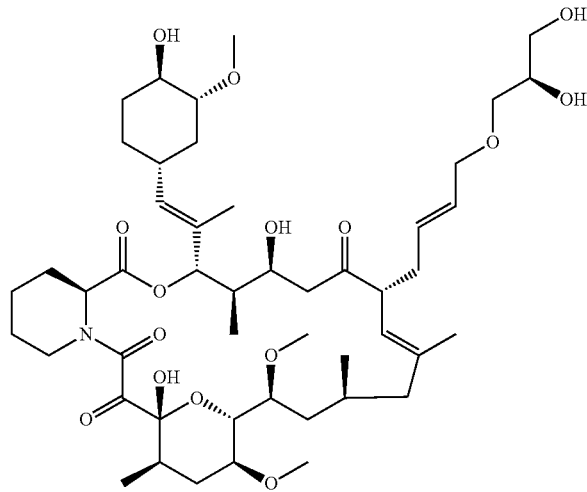 [SMILES: CO[C@H]1C[C@@H](C)C/C(C)=C/[C@@H](C/C=C/COC[C@H](O)CO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{48}H_{77}NO_{15}$
191
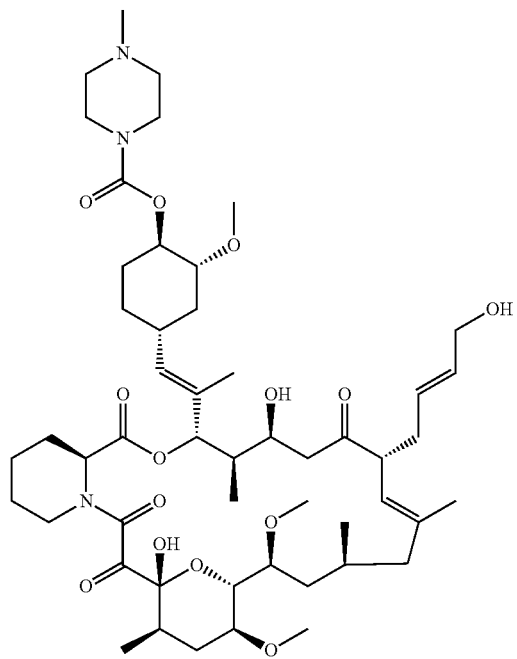 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CCN(C)CC3)[C@H](OC)C2)OC(=O)[C@@H]2CCCCN2C(=O)C(=O)[C@]2(O)O[C@H]1[C@@H](OC)C[C@H]2C]
$C_{51}H_{81}N_3O_{14}$

TABLE 1-continued
Antifungal Compounds
192
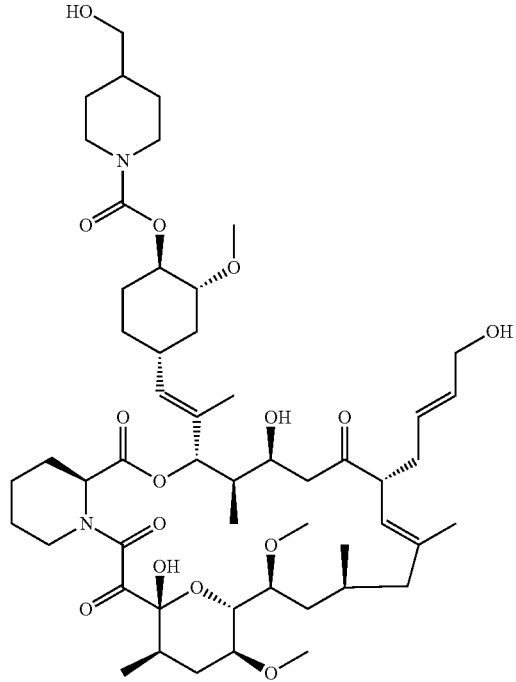 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CCC(CO)CC3)[C@H](OC)C2)OC(=O)[C@@H]2CCCCN2C(=O)C(=O)[C@]2(O)O[C@H]1[C@@H](OC)C[C@H]2C]
$C_{52}H_{82}N_2O_{15}$
193
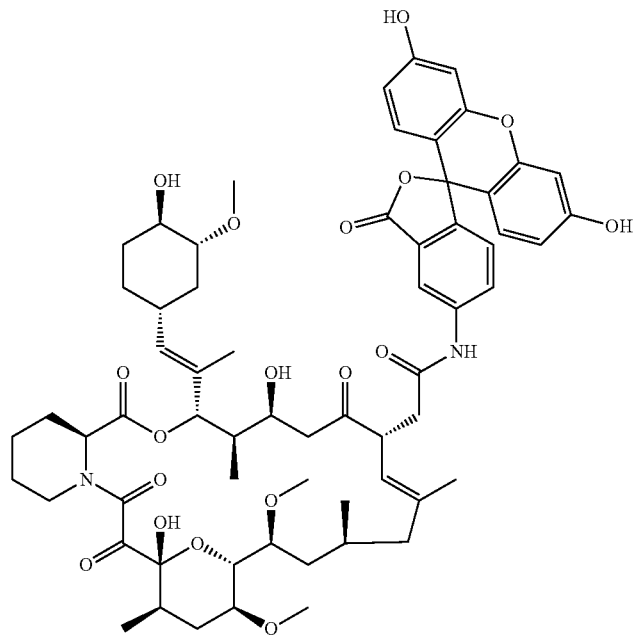 [SMILES: CO[C@H]1C[C@@H](C)C/C(C)=C/[C@@H](CC(=O)Nc2ccc3c(c2)C(=O)OC32c3ccc(O)cc3Oc3cc(O)ccc32)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{63}H_{78}N_2O_{18}$ TABLE 1-continued
Antifungal Compounds
194
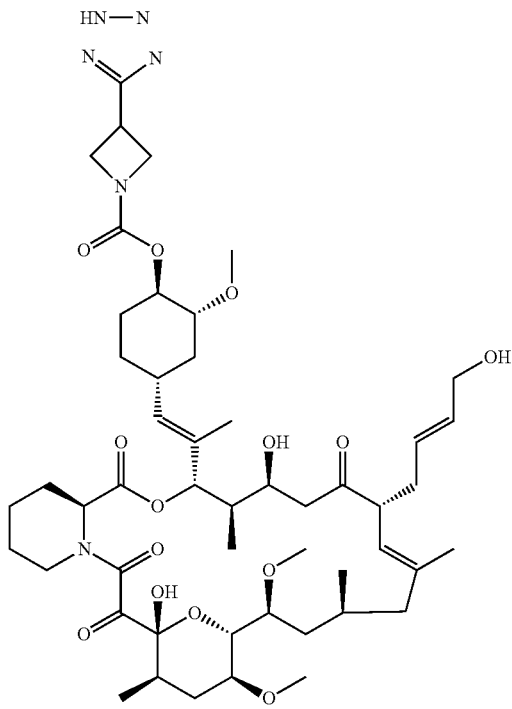
$C_{50}H_{76}N_6O_{14}$
195
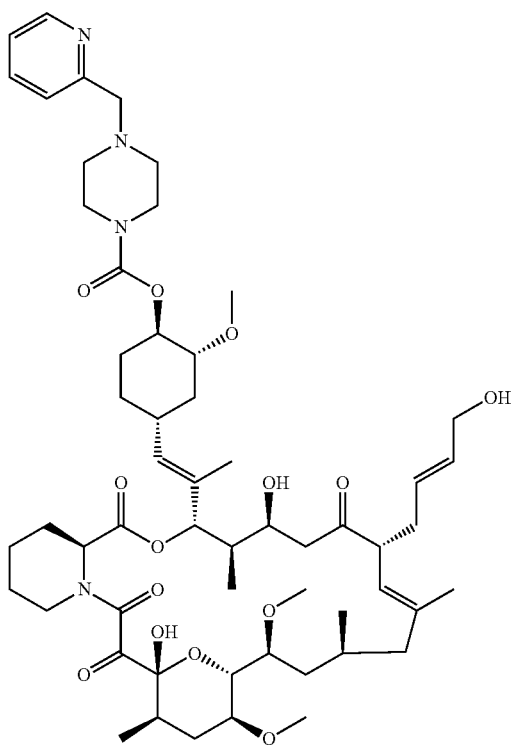 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CCN(Cc4ccccn4)CC3)[C@H](OC)C2)OC(=O)[C@@H]2CCCCN2C(=O)C(=O)[C@]2(O)O[C@H]1[C@@H](OC)C[C@H]2C]
$C_{56}H_{84}N_4O_{14}$ TABLE 1-continued
Antifungal Compounds
196
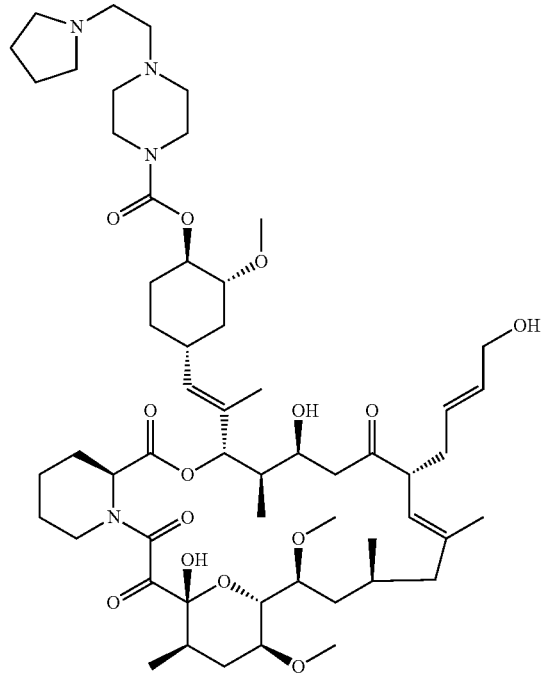 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CCN(CCN4CCCC4)CC3)[C@H](OC)C2)OC(=O)[C@@H]2CCCCN2C(=O)C(=O)[C@]2(O)O[C@H]1[C@@H](OC)C[C@H]2C]
$C_{56}H_{90}N_4O_{14}$
197
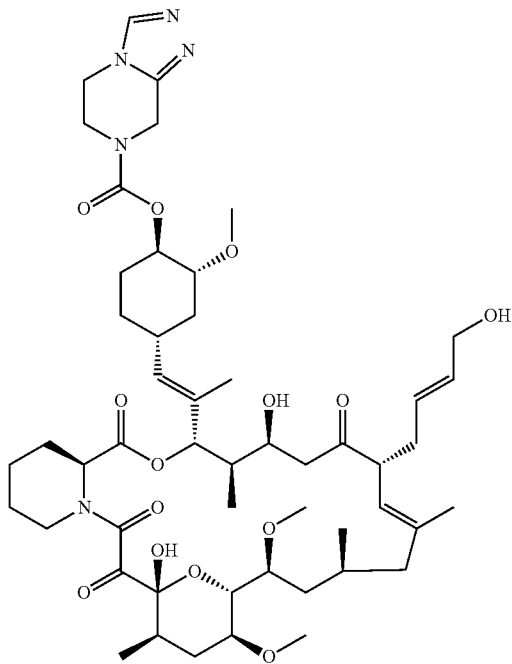 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CCN(C=N)C(=N)C3)[C@H](OC)C2)OC(=O)[C@@H]2CCCCN2C(=O)C(=O)[C@]2(O)O[C@H]1[C@@H](OC)C[C@H]2C]
$C_{51}H_{77}N_5O_{14}$ TABLE 1-continued
Antifungal Compounds
198
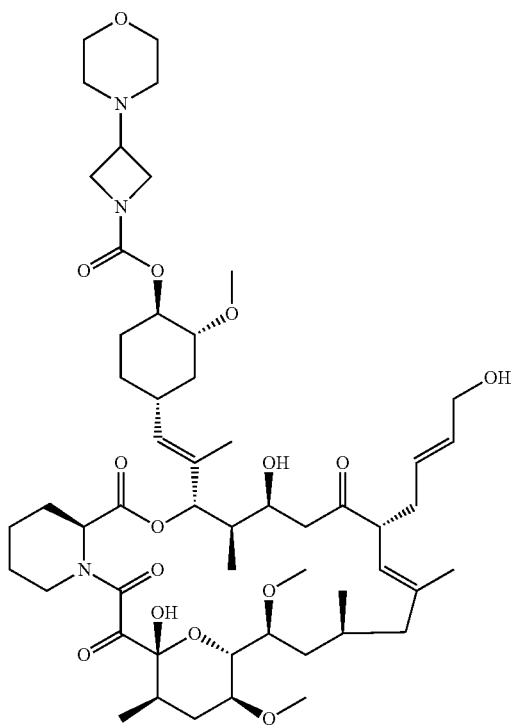 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CC(N4CCOCC4)C3)[C@H](OC)C2)OC(=O)[C@@H]2CCCCN2C(=O)C(=O)[C@]2(O)O[C@H]1[C@@H](OC)C[C@H]2C]
199
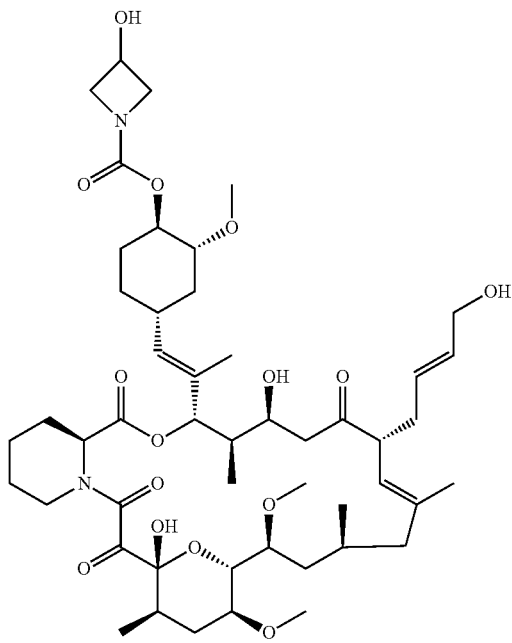 [SMILES: CO[C@H]1C[C@@H](C)C/C(C)=C/[C@@H](C/C=C/CO)C(=O)C[C@H](O)[C@@H](C)[C@@H](/C(C)=C/[C@@H]2CC[C@@H](OC(=O)N3CC(O)C3)[C@H](OC)C2)OC(=O)[C@@H]2CCCCN2C(=O)C(=O)[C@]2(O)O[C@H]1[C@@H](OC)C[C@H]2C]
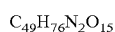

TABLE 1-continued
Antifungal Compounds
200
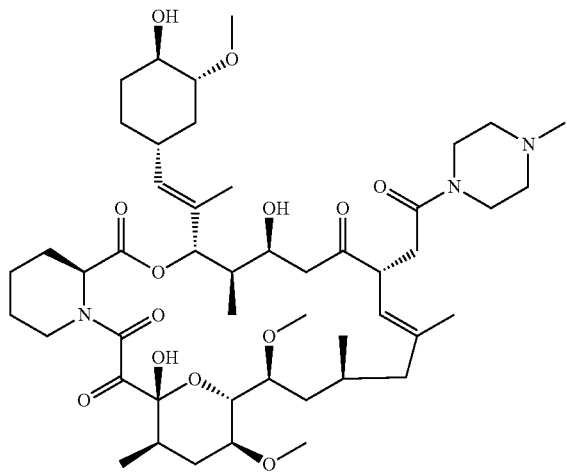 [SMILES: CO[C@H]1C[C@@H](C)C/C(C)=C/[C@@H](CC(=O)N2CCN(C)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
201
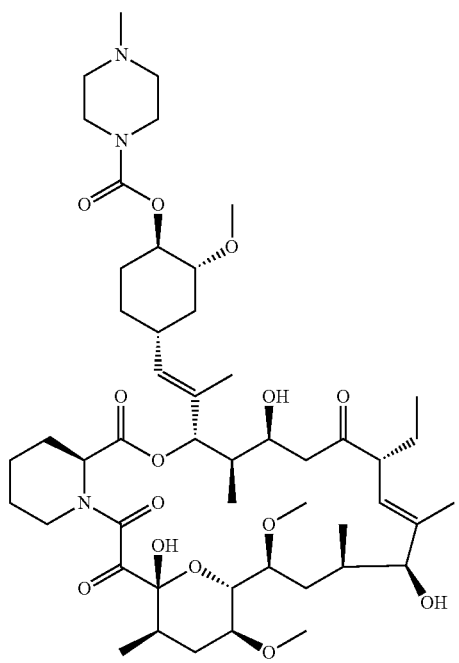 [SMILES: CC[C@@H]1/C=C(\C)[C@@H](O)[C@H](C)C[C@H](OC)[C@H]2O[C@@](O)(C(=O)C(=O)N3CCCC[C@H]3C(=O)O[C@H](/C(C)=C/[C@@H]3CC[C@@H](OC(=O)N4CCN(C)CC4)[C@H](OC)C3)[C@H](C)[C@@H](O)CC1=O)[C@H](C)C[C@@H]2OC]
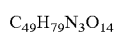

161 162
TABLE 1-continued
Antifungal Compounds
202
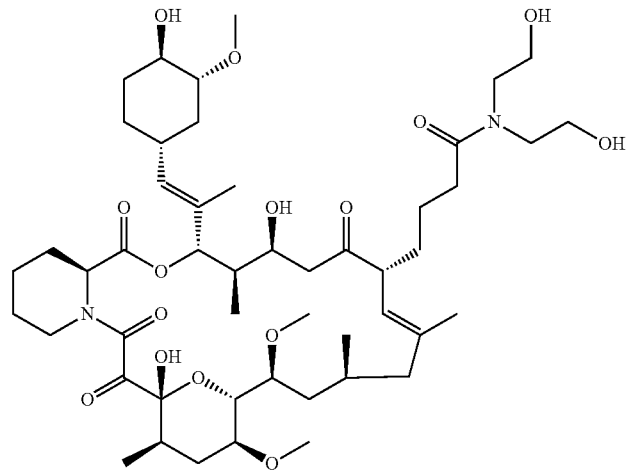 [SMILES: CO[C@H]1C[C@@H](C)C/C(C)=C/[C@@H](CCCC(=O)N(CCO)CCO)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
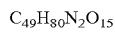
203
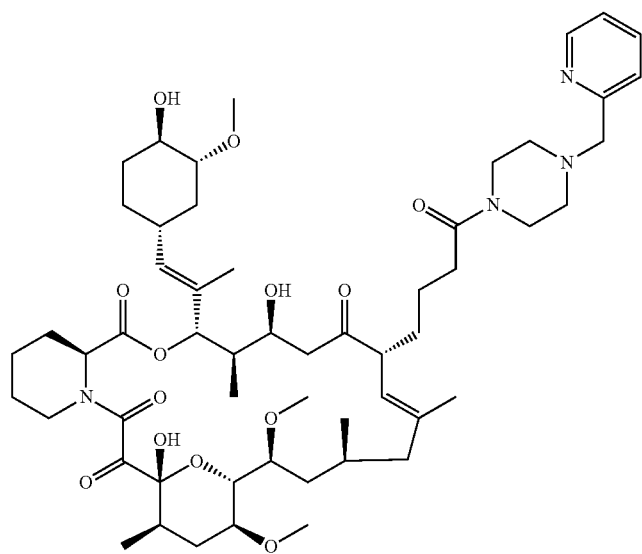 [SMILES: CO[C@H]1C[C@@H](C)C/C(C)=C/[C@@H](CCCC(=O)N2CCN(Cc3ccccn3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
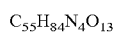

TABLE 1-continued
Antifungal Compounds
204
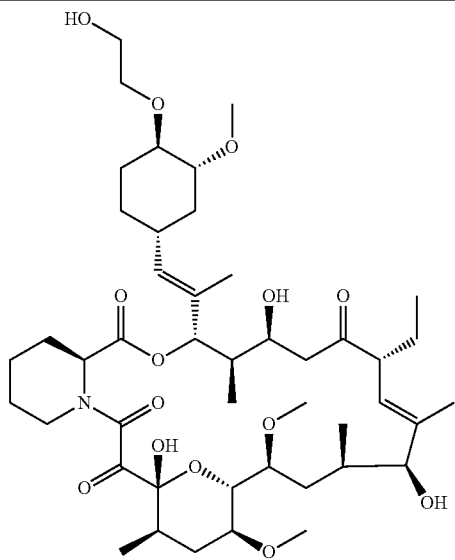
$C_{45}H_{73}NO_{14}$
205
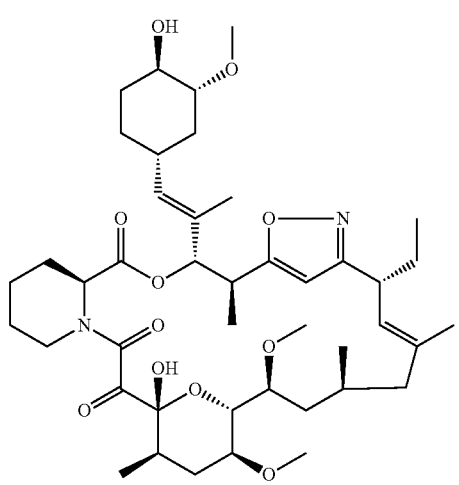 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)c3cc1no3)[C@H](C)C[C@@H]2OC]
$C_{43}H_{66}N_2O_{11}$
206
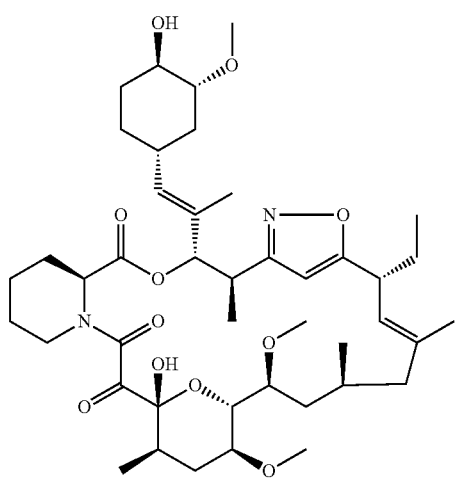 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)c3cc1on3)[C@H](C)C[C@@H]2OC]
$C_{43}H_{66}N_2O_{11}$

TABLE 1-continued
Antifungal Compounds
207
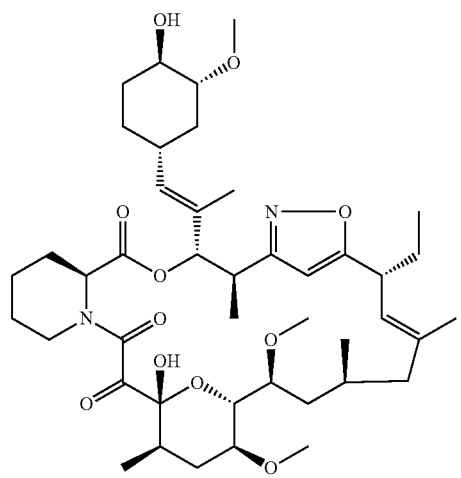 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)c3cc1on3)[C@H](C)C[C@@H]2OC]
$C_{43}H_{66}N_2O_{11}$
208
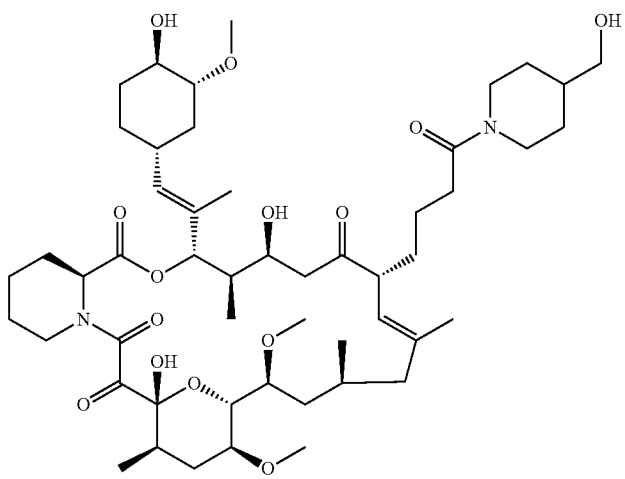 [SMILES: CO[C@H]1C[C@@H](C)C/C(C)=C/[C@@H](CCCC(=O)N2CCC(CO)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{51}H_{82}N_2O_{14}$
209
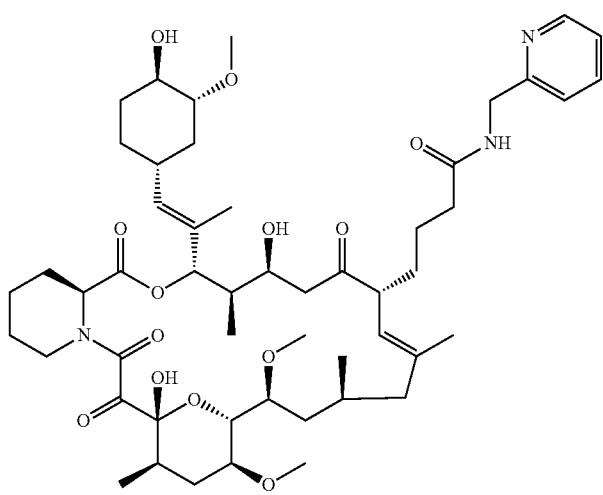 [SMILES: CO[C@H]1C[C@@H](C)C/C(C)=C/[C@@H](CCCC(=O)NCc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
$C_{51}H_{77}N_3O_{13}$ TABLE 1-continued
Antifungal Compounds
210
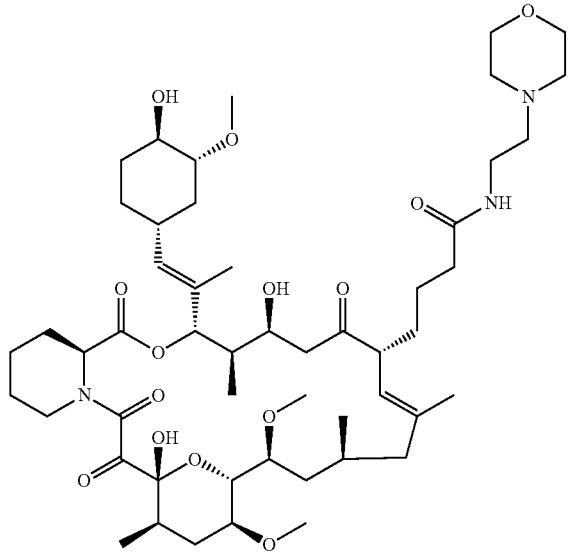 [SMILES: CO[C@H]1C[C@@H](C)C/C(C)=C/[C@@H](CCCC(=O)NCCN2CCOCC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
C$_{51}$H$_{83}$N$_3$O$_{14}$
211
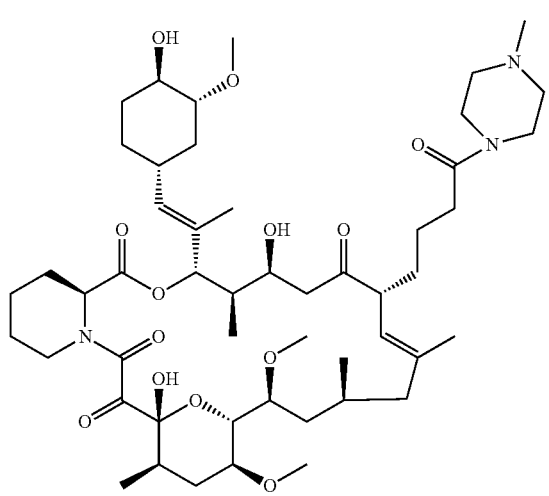 [SMILES: CO[C@H]1C[C@@H](C)C/C(C)=C/[C@@H](CCCC(=O)N2CCN(C)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
C$_{50}$H$_{81}$N$_3$O$_{13}$ TABLE 1-continued
Antifungal Compounds
212
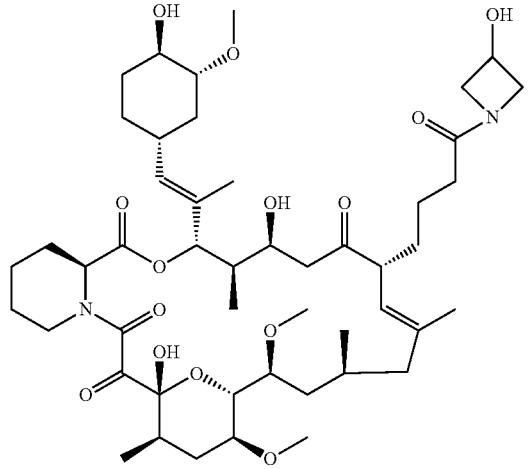 [SMILES: CO[C@H]1C[C@@H](C)C/C(C)=C/[C@@H](CCCC(=O)N2CC(O)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
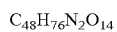
213
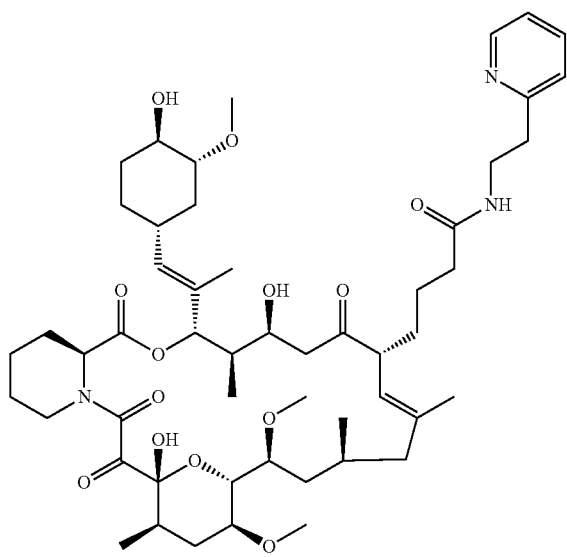 [SMILES: CO[C@H]1C[C@@H](C)C/C(C)=C/[C@@H](CCCC(=O)NCCc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
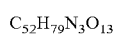

TABLE 1-continued
Antifungal Compounds
214 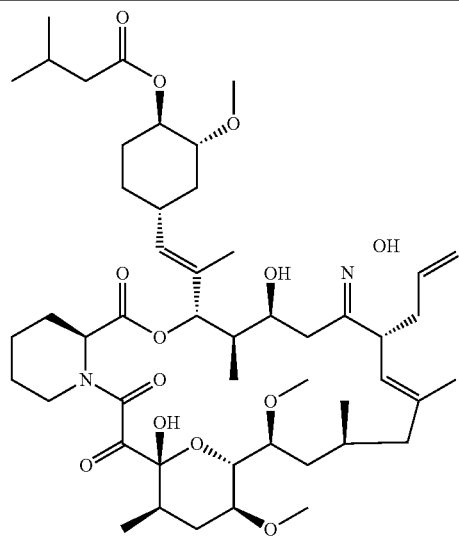
$C_{49}H_{78}N_2O_{13}$
215 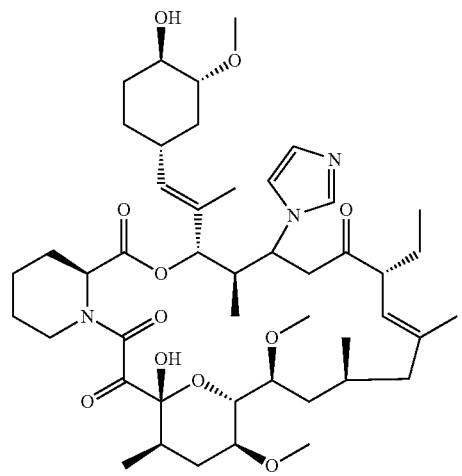 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)C(n3ccnc3)CC1=O)[C@H](C)C[C@@H]2OC]
$C_{46}H_{71}N_3O_{11}$
216
217 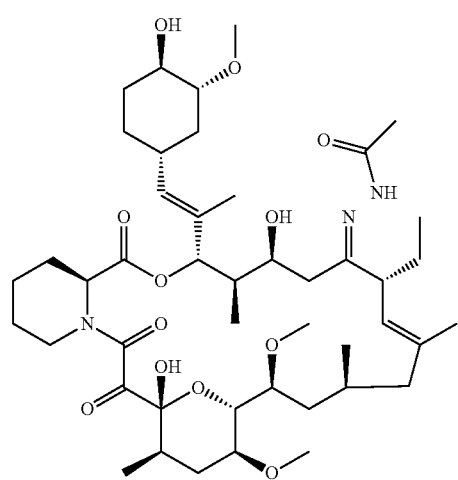
$C_{45}H_{73}N_3O_{12}$ TABLE 1-continued Antifungal Compounds

218

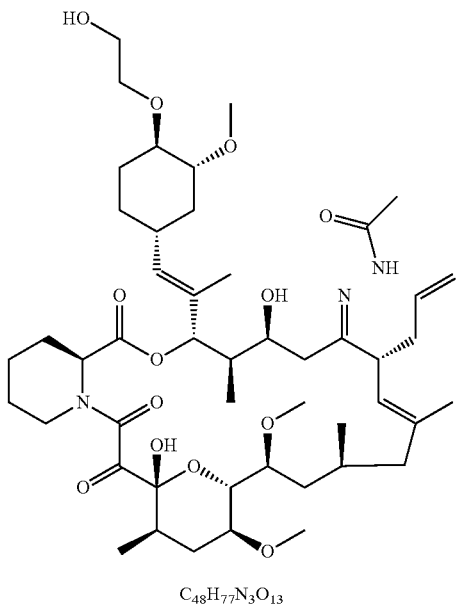

$C_{48}H_{77}N_3O_{13}$

219

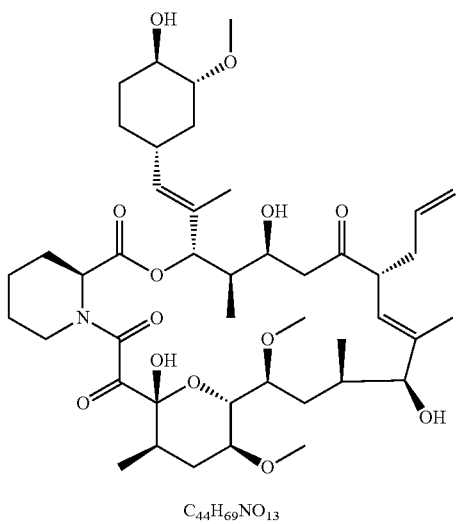

$C_{44}H_{69}NO_{13}$

EXAMPLES

Preparation of "$C_{22}$"-Oximes from FK506 or Ascomycin

Example Procedure: Combined FK506 (0.50 g, 0.60 mmol), hydroxylamine hydrochloride (0.50 g, 7.0 mmol), pyridine (0.25 mL, 3.2 mmol), and ethanol (60 mL). The mixture was heated at reflux. LCMS at 2 h indicated complete reaction. The mixture was cooled to rt, diluted with water, and treated with dilute HCl (to ~pH4). The Ethanol was evaporated, and the residue was extracted into DCM three times. The combined organic phase was washed with brine, dried over $Na_2SO_4$, and evaporated to give a white solid. Purification by Biotage flash chromatography (25 g SNAP column, 7-60% Acetone/Hexane). Fraction 16 (82 mg, 16%) appears to be enriched in one oxime isomer, fraction 18 (68 mg, 13%) appears to be enriched in the other oxime isomer, and fraction 17 (103 mg, 20%) is a less-enriched mixture of isomers.

Preparation of "C22"-Hydrazones From FK506 or Ascomycin

Example Procedure: Combined FK506 (0.50 g, 0.62 mmol), Ethanol (35 mL), 2-hydroxyethylhydrazine (0.25 mL, 3.7 mmol), and TsOH (0.71 g, 3.7 mmol). The mixture was stirred at rt for 20 h. The solvent was evaporated and the residue was purified by Biotage flash chromatography (25 g SNAP, 7-60% Acetone/Hexane). The appropriate fractions were combined and further purified by NP-HPLC (Kromasil, 4.6 mm×250 mm, 100-5 sil, 20% EtOH/Heptane). The appropriate fractions were combined and evaporated to give the desired material as a white solid (32 mg 6%).

Preparation of C23-C24-dehydro-C22-ethylhydrazone From FK506

Procedure: Combined FK506 (300 mg, 0.37 mmol), ethanol (21 mL), ethylhydrazine hydrochloride (216 mg, 2.2 mmol), and TsOH (426 mg, 2.2 mmol), and the mixture was stirred at rt. LCMS at 18 h indicated no starting material remained. The mixture was diluted with DCM and water and then adjusted to neutral pH with NaHCO$_3$. The organic solvents were evaporated and the aqueous residue was extracted with DCM three times. The combined organics were washed with brine, dried over Na$_2$SO$_4$, and evaporated to give an oil. Purification with Biotage flash chromatography (25 g SNAP, 7-60% acetone/hexanes). Both the C24-hydroxy-C22-hydrazone (24 mg, 8%) and the C23-C24-dehydro-C22-hydrazone (22 mg, 7%) were isolated from a separable mixture.

Preparation of C22 Exocyclic Alkenes from Ascomycin

Example Procedure using the Peterson Olefination: C24,C32-bis-TBS-protected ascomycin (0.18 g, 0.18 mmol) was dissolved in THF (5 mL) and the solution was cooled to –78° C. TMSCH$_2$Li (0.44 mL of 1M solution in pentane, 0.44 mmol) was added dropwise (a yellow color appeared and dissipated with each drop, and then an orange color finally persisted. The mixture was maintained at –78° C. for 20 h. The reaction was quenched at –78° C. with two drops of glacial acetic acid. Water was added and the mixture was brought to rt. The mixture was treated with a saturated solution of NaHCO$_3$, and then the pH 8 mixture was extracted with ether. The ethereal extract was washed with brine, dried over Na$_2$SO$_4$, and then evaporated to give an oil. This material was then dissolved in acetonitrile (4.5 mL), and treated with a 48% aqueous HF solution (0.50 mL, 14 mmol). The mixture was stirred for 8 h, and then quenched by the addition of ethoxytrimethylsilane (2.0 mL, 12.8 mmol). The mixture was evaporated to dryness and purified by Biotage flash chromatography (10 g SNAP column, 7-60% acetone/hexanes). The product containing fractions were combined and further purified by normal phase HPLC (Kromasil, 4.6 mm×250 mm, 100-5 sil). The appropriate fractions were combined to give the desired product as a glassy solid (9.2 mg, 7%).

Example Procedure using a disubstituted alkyl lithium: C24,C32-bis-TBS-protected ascomycin (0.29 g, 0.28 mmol) was dissolved in THF (8 mL) and the solution was cooled to –78° C. Sec-butyl lithium (0.50 mL of a 1.4 M solution in cyclohexane, 0.70 mmol) was added dropwise (a yellow color appeared and dissipated with each drop, and then an orange color finally persisted. The mixture was maintained at –78° C. for 24 h. The reaction was quenched at –78° C. with 3 drops of glacial acetic acid. Water was added and the mixture was brought to rt. The mixture was treated with a saturated solution of NaHCO$_3$, and then the pH 8 mixture was extracted with ether. The ethereal extract was washed with brine, dried over Na$_2$SO$_4$, and then evaporated to give an oily white solid. This material was then dissolved in acetonitrile (7.5 mL), and treated with a 48% aqueous HF solution (0.80 mL, 22 mmol). The mixture was stirred for 8 h, and then quenched by the addition of ethoxytrimethylsilane (2.0 mL, 12.8 mmol). The mixture was evaporated to dryness and purified by Biotage flash chromatography (10 g SNAP column, 7-60% acetone/hexanes). The product containing fraction was further purified by normal phase HPLC (Kromasil, 4.6 mm×250 mm, 100-5 sil). The appropriate fractions were combined to give the desired product (11 mg, 5%).

Preparation of C22,C24-Acetonide From Ascomycin

Procedure: Dissolved Me$_4$N(OAc)$_3$BH (0.80 g, 0.30 mmol) in ACN (1 mL) and glacial acetic acid (1.5 mL) at rt. Cooled to 0° C. and stirred for 10 min, then added a solution of ascomycin (0.30 g, 0.38 mmol) dissolved in ACN (1.5 mL) and EtOAc (1 mL). The vial was sealed and the mixture stirred at 0° C. LCMS after 2 h indicated no starting material remained. The desired m/z was present along with the m/z corresponding to over-reduction. The reaction was quenched with Rochelle's Salt (0.5 M, 2 mL) and the mixture was transferred to a round bottom flask and evaporated. The residue was extracted with ethyl acetate (3×25 mL). The combined organic phase was washed with brine, dried over sodium sulfate, and then the solvent was evaporated. The crude product was dissolved in acetone (13 mL) and 2,2-dimethoxypropane (13 mL), and then a catalytic amount of pyridinium-p-toluenesulfonate was added (10 mg, 0.038 mmol). The mixture was stirred at rt, and after one day there was no remaining starting material by TLC. The mixture was diluted with water, and then saturated sodium bicarbonate solution was added (1 mL). The solvents were evaporated and the aqueous residue was extracted with DCM (3×25 mL). The combined organic phase was washed with brine and dried over sodium sulfate. The solvent was evaporated to give a white solid which was purified by Biotage Isolera flash chromatography (10 g SNAP column, 5-40-65% (ethyl acetate/hexanes) step-gradient. The appropriate fractions were combined to give the desired product as a white solid (19 mg, 6%).

Preparation of C23-C24-dehydro-C22-methyloxime From Ascomycin

Procedure: Ascomycin (6.8 g, 8.6 mmol) was dissolved in toluene (140 mL) and then p-toluenesulfonic acid monohydrate (0.68 g, 3.6 mmol) was added in one portion. The solution was heated to 80° C. The mixture continued to stir at 80° C. for a total of 1 h. The mixture was cooled to rt, and without concentrating the solution, the mixture was passed through a plug of silica/Celite eluting with ether and toluene. A black insoluble residue remained clinging to the flask. Concentration of the eluent in vacuo provided a dark tar. The material was purified by Biotage flash chromatography in three portions (50 g SNAP, 7-40% acetone/hexanes). The appropriate fractions from each chromatography were combined and evaporated to give Δ23-24-dehydroascomycin as a white powder (4.0 g, 61%).

Δ23-24-dehydroascomycin (0.54 g, 0.70 mmol) was dissolved in absolute ethanol (65 mL), and then methoxylamine hydrochloride (0.70 g, 8.4 mmol) was added followed by pyridine (0.56 mL, 7.0 mmol). The mixture was stirred at 60° C. After 3.5 h, the reaction was cooled to rt and diluted with water. The ethanol was rotary evaporated. The aqueous residue was treated with a saturated aqueous NaHCO$_3$ solution to adjust to pH 6, and then extracted with EtOAc (3×50 mL). The combined organic phase was washed with brine, dried over Na$_2$SO$_4$, and evaporated to give a white solid. Purification by Biotage FC (25 g SNAP, 7-60% Acetone/Hexane). The appropriate fractions were combined and evaporated to give the desired product as a white solid (0.29 g, 51%).

Preparation of C24-deoxyascomycin

Ascomycin (6.8 g, 8.6 mmol) was dissolved in toluene (140 mL) and then p-toluenesulfonic acid monohydrate (0.68 g, 3.6 mmol) was added in one portion. The solution was heated to 80° C. The mixture continued to stir at 80° C. for a total of 1 h. The mixture was cooled to rt, and without concentrating the solution, the mixture was passed through a plug of silica/Celite eluting with ether and toluene. A black insoluble residue remained clinging to the flask. Concentration of the eluent in vacuo provided a dark tar. The material was purified by Biotage flash chromatography in three portions (50 g SNAP, 7-40% acetone/hexanes). The appropriate fractions from each chromatography were combined and evaporated to give Δ73-24-dehydroascomycin as a white powder (4.0 g, 61%).

The Δ23-24-dehydroascomycin (1.6 g, 2.0 mmol) was dissolved in methanol (25 mL) and added to a suspension of 10% palladium on carbon (0.12 g) in methanol (25 mL). The flask was purged with nitrogen, then hydrogen. A balloon with hydrogen was affixed to the flask with a needle through a rubber septum. The mixture was stirred briskly for 18 min, before carefully filtering through a pad of Celite with MeOH (make sure to keep the pad of Celite wet with MeOH). The solvent was evaporated to give a gray foamy solid. Purification by Biotage flash chromatography (50 g SNAP, 7-60% acetone/hexane, collecting on threshold (30 mAu). Fractions 4-5 were combined and evaporated to give C24-deoxyascomycin as a foamy white solid (0.73 g, 46%).

Preparation of C24-deoxy-C22-hydroxy Ascomycin

Ascomycin (6.8 g, 8.6 mmol) was dissolved in toluene (140 mL) and then p-toluenesulfonic acid monohydrate (0.68 g, 3.6 mmol) was added in one portion. The solution was heated to 80° C. The mixture continued to stir at 80° C. for a total of 1 h. The mixture was cooled to rt, and without concentrating the solution, the mixture was passed through a plug of silica/Celite eluting with ether and toluene. A black insoluble residue remained clinging to the flask. Concentration of the eluent in vacuo provided a dark tar. The material was purified by Biotage flash chromatography in three portions (50 g SNAP, 7-40% acetone/hexanes). The appropriate fractions from each chromatography were combined and evaporated to give Δ73-24-dehydroascomycin as a white powder (4.0 g, 61%).

The Δ23-24-dehydroascomycin (1.6 g, 2.0 mmol) was dissolved in methanol (25 mL) and added to a suspension of 10% palladium on carbon (0.12 g) in methanol (25 mL). The flask was purged with nitrogen, then hydrogen. A balloon with hydrogen was affixed to the flask with a needle through a rubber septum. The mixture was stirred briskly for 18 min, before carefully filtering through a pad of Celite with MeOH (make sure to keep the pad of Celite wet with MeOH). The solvent was evaporated to give a gray foamy solid. Purification by Biotage flash chromatography (50 g SNAP, 7-60% acetone/hexane, collecting on threshold (30 mAu). Fractions 4-5 were combined and evaporated to give C24-deoxyascomycin as a foamy white solid (0.73 g, 46%).

To a solution of C24-deoxyascomycin (0.33 g, 0.42 mmol) in THF (4 mL) at −70° C. was added K-Selectride (1.1 mL of 1.0 M soln in THF, 1.1 mmol) dropwise. The temperature remained at −70° C. to −40° C., and TLC at 4 h indicated no rxn. The clear/colorless soln was placed into the −20° C. freezer. It gradually turned yellow, then orange, over a 2 h period. The mixture was cautiously poured into a beaker of ice. Dilute HCl was added to adjust to neutral pH (the solution became colorless). The mixture was extracted with ethyl acetate (3×50 mL). The combined organic phase was successively washed with water and brine, then dried over $Na_2SO_4$. The volatiles were evaporated to give a yellow oil. The mixture was purified by Biotage FC (25 g SNAP, 7-60% Acetone/Hexanes). The appropriate fractions were combined and evaporated to give the desired product as a white solid (0.16 g, 48%).

Preparation of C22-oximes-C21-alkenes (other than allyl) From Tacrolimus

Example Procedure using hydroxylamine and propene: FK506 (2.0 g, 2.5 mmol) was dissolved in diethyl ether (40 mL), and the mixture was de-gassed with nitrogen for 10 min. Dichloro[1,3-bis(2,6-isopropylphenyl)-2-imidazolidinylidene](benzylidene) (tricyclohexylphosphine)ruthenium (II) "Furstner catalyst" (30 mg) and CuI (20 mg) were then added, followed by liquid propene (5 mL, condensed from gas) and the mixture was stirred for 16 h at rt. Isolute Si-Thiol resin (Biotage) was added, and the mixture was stirred for 1 hr, then allowed to stand. The supernatant was decanted, and the resin was washed with ether (20 mL) and hexane (20 mL). The combined supernatants were concentrated in vacuo to an oily residue. This material was purified by preparative HPLC to give the desired propenyl compound as a white solid.

The product from above (0.10 g, 0.12 mmol), hydroxylamine hydrochloride (0.017 g, 0.24 mmol), pyridine (1 mL), and ethanol (1 mL) were placed in a 4 mL vial and stirred overnight at rt. The ethanol was evaporated and the residue was poured into 1M HCl (aq). The product was extracted with dichloromethane, and the solvent was evaporated to give a clear glassy solid. This material was purified by Biotage flash chromatography (10 g SNAP, 40% acetone/ hexane). The appropriate fractions were collected, pooled and concentrated to give a glassy solid which was then dissolved in acetonitrile/water and lyophilized to give the desired product (a pair of isomers) as a white powder (10 mg, 10%).

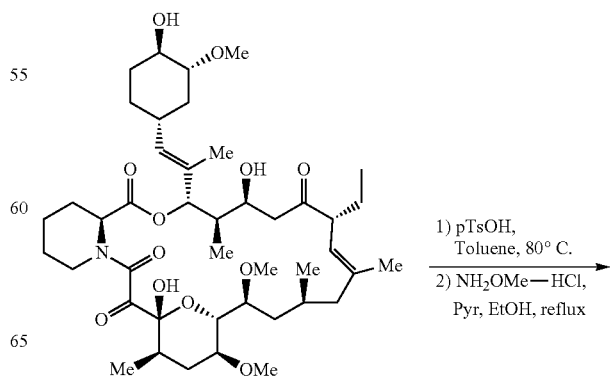

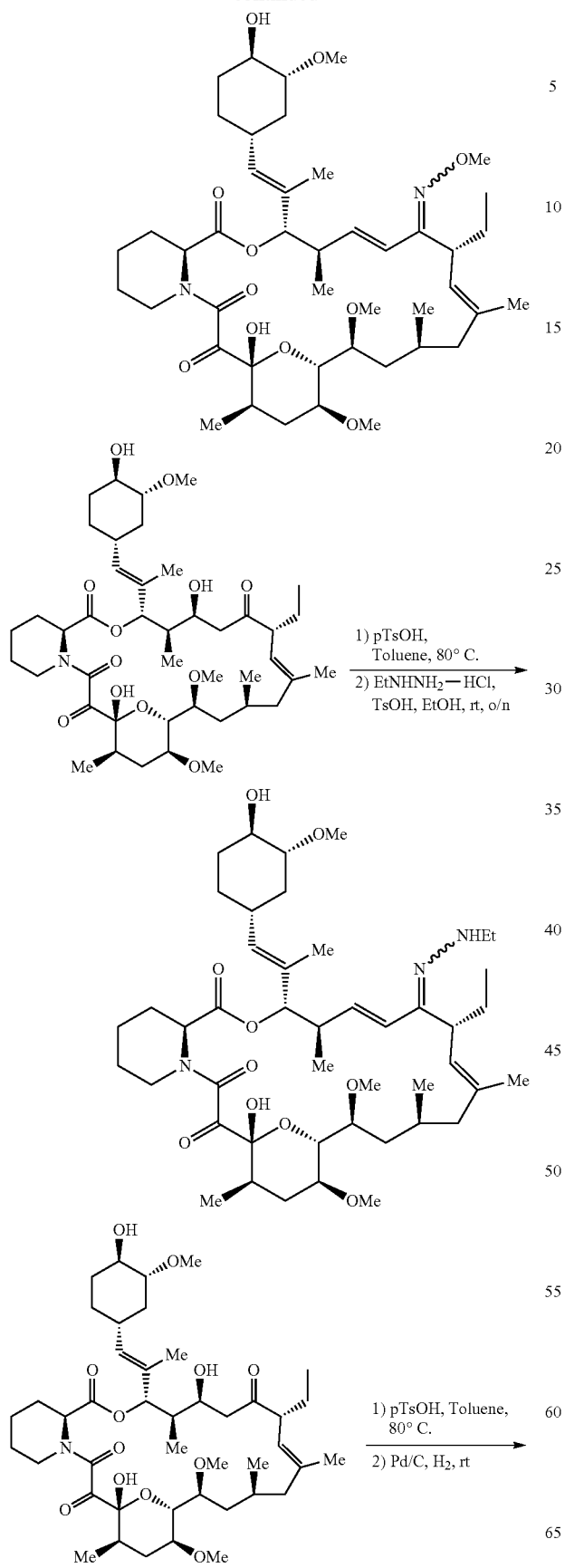
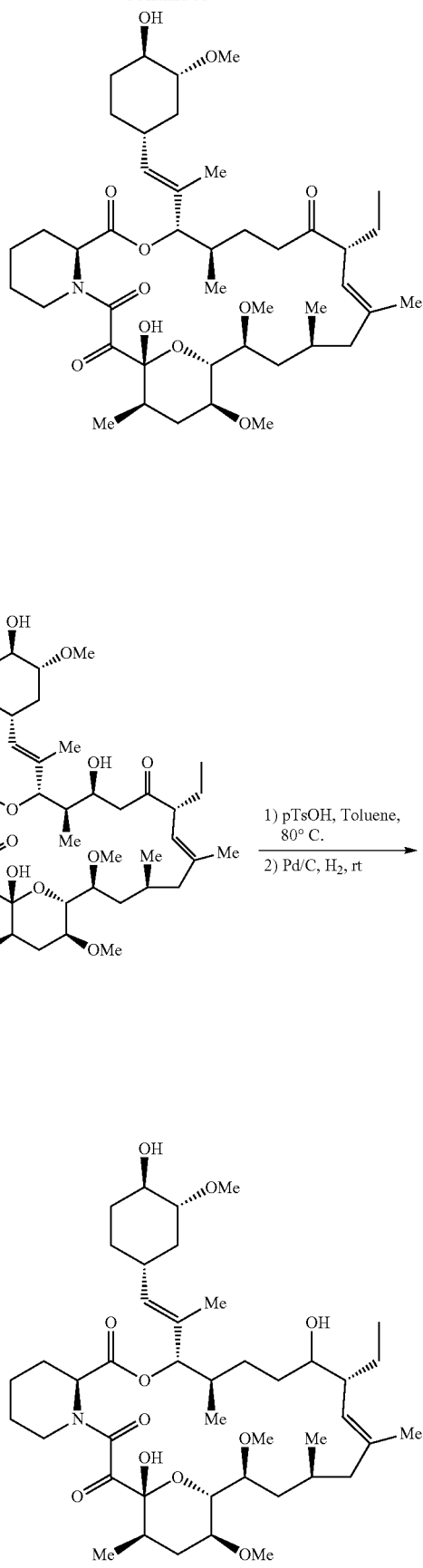

181
-continued
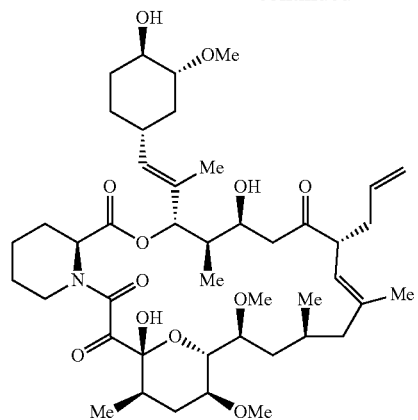
NH$_2$OH—HCl
Pyridine, EtOH
reflux, 2 h
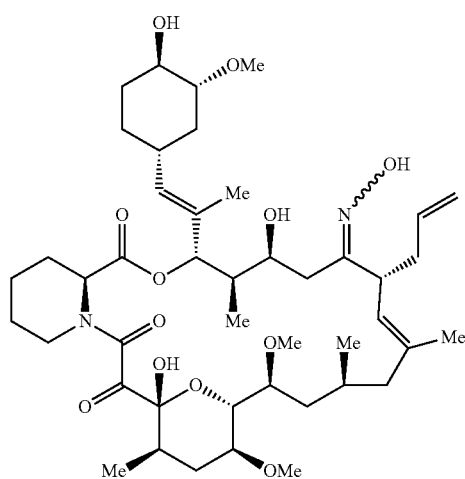
EtNHNH$_2$—HCl
TsOH, EtOH
rt, o/n
182
-continued
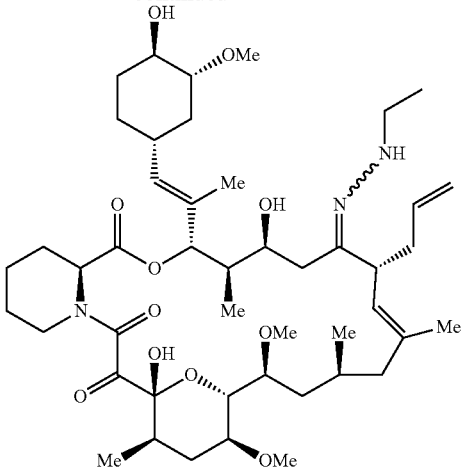
1) TBSCl, Imid., DCM
2) TMSCH$_2$Li, THF, -78° C.
3) 48% HF, ACN, rt
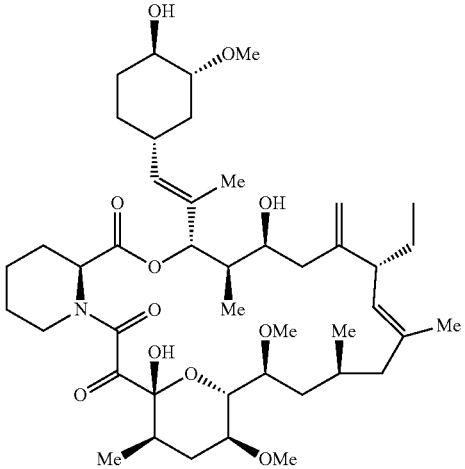
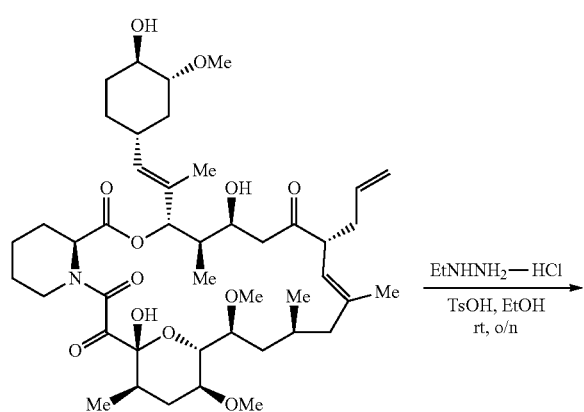
1) Me$_4$N(OAc)$_3$BH, HOAc, MeCN, 0° C.
2) 2,2-Dimethoxypropane, Acetone, PPTS 183
-continued
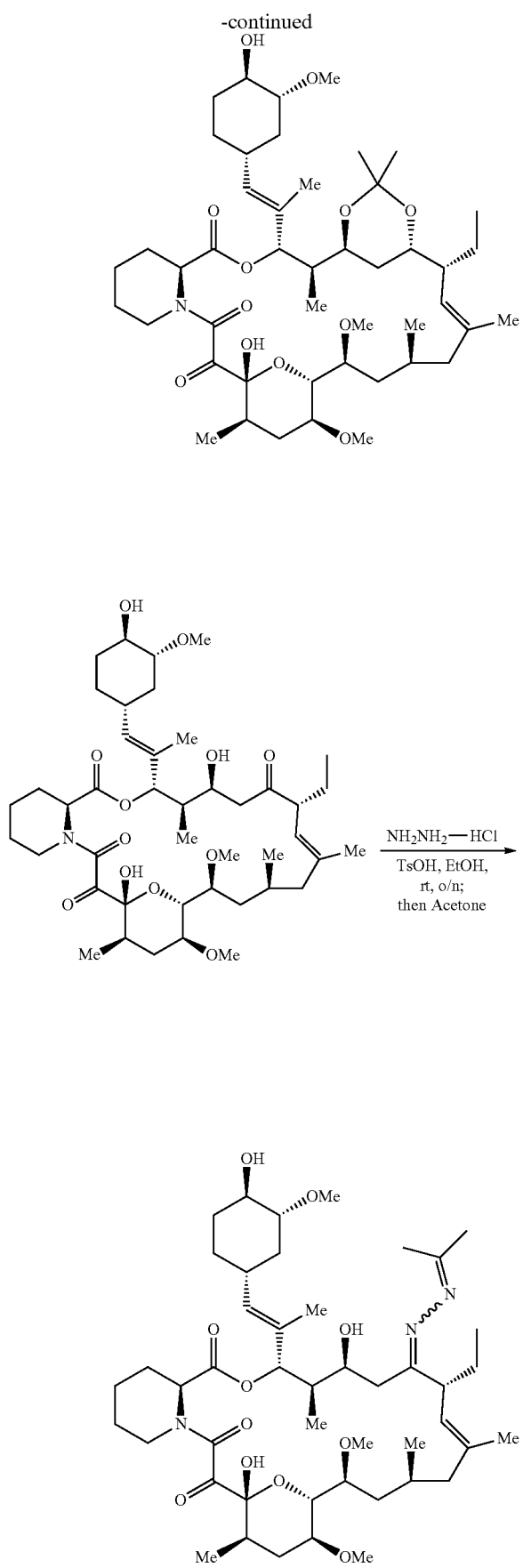
184
-continued
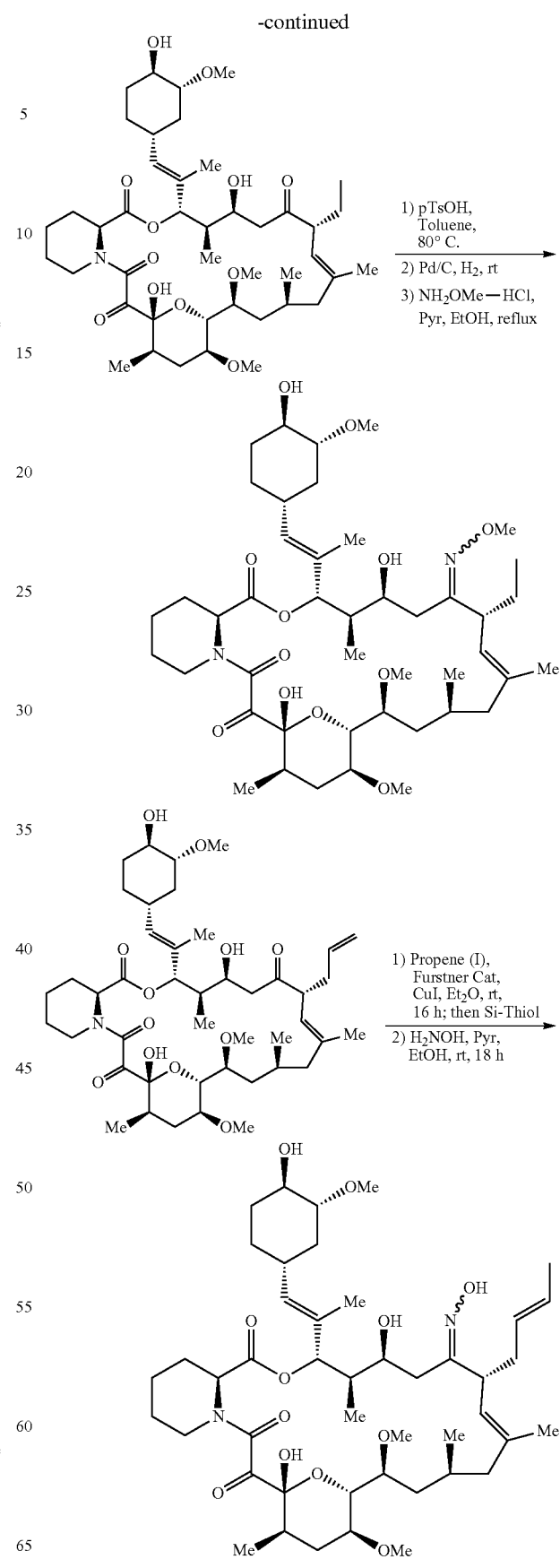

Activity: Activity against C. neo, Candida, Candida w/ FLu., Asp, and Asp/Caspo was determined using standardized in vitro susceptibility tests; see, Clinical and Laboratory Standards Institute (CLSI) and the European Committee for Antimicrobial Susceptibility Testing (EUCAST), and compounds 2-219 each demonstrate antifungal activity against one or more of these fungi; exemplary, excerpted data are shown below.

| Compound | Active C. neo | Active Candida w/ FLu. | Active Asp alone (MEC) | Active Asp Caspo |
|---|---|---|---|---|
| 2 | yes | no | yes | Yes |
| 3 | yes | yes | no | yes 4 ug/mL |
| 4 | yes | yes | no | yes 8 ug/mL |
| 5 | yes | yes | yes (8 ug/mL) | yes 1 ug/mL |

Compounds most active against C. neo include #2-6, 8, 11, 14-18, 20, 23-24, 26-28, 30-32, 35-44, 47, 50, 55, 58-80, 82, 86-91, 97-102, 116, 118-120, 123, 127-128, 133-135, 138-150 and 152-161.

Compounds most active against Asp include #2, 5, 11, 15-18, 23, 24, 26, 39, 52, 55, 79, 86, 87, 89, 97-101, 132-141, 144, 146-150, 152, 153, 155-158, 160, 161, 163, 166, 174, 178, and 179-181.

IL2 $IC_{50}$ values were also determined, with compounds 2-219 demonstrating $IC_{50}$ in the subnanomolar (e.g. #42, 51, 61, 75-76, 103, 126, 129, 132, 138, 140, 151, 163), nanomolar (e.g. #2, 3, 8, 18, 23-24, 31-32, 37, 39-40, 44, 52, 60, 62-66, 68-69, 71-72, 77-79, 81-91, 96-102, 104-125, 127, 130-131, 133-137, 139, 142-150, 152-154, 157-158, 160-162, 164-168, 170, 172-175, 178-179, 184) and micromolar (e.g. #53, 55-57, 67, 70, 73-74, 80, 112, 155, 177) ranges.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A composition comprising a compound of formula (I):

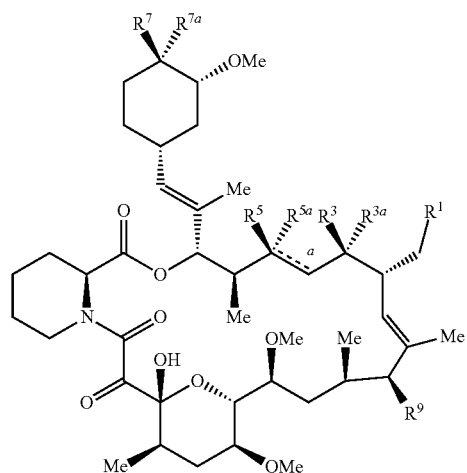

wherein:

"a" is a double bond that may be present provided that $R^{5a}$ is not present;

$R^1$ is selected from alkyl, alkenyl;

$R^3$ and $R^{3a}$ together form an imine, a substituted imine, a hydrazone, or a substituted hydrazone;

$R^5$ is —OH and $R^{5a}$ is —H;

$R^7$ is —OH and $R^{7a}$ is —H; and

R9 is —H, or a pharmaceutically acceptable salt thereof.

2. The composition of claim 1, wherein R1 is alkenyl.

3. A composition comprising a compound wherein the compound is

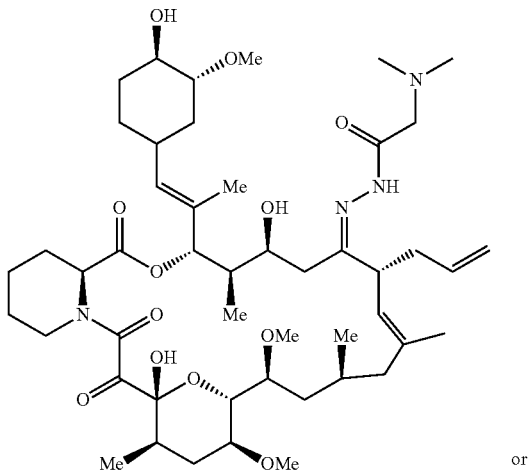

or

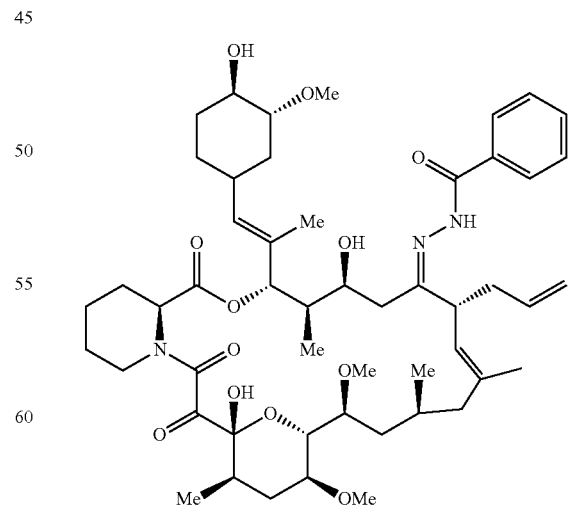

* * * * *